(12) United States Patent
Rajotte et al.

(10) Patent No.: US 6,784,153 B1
(45) Date of Patent: Aug. 31, 2004

(54) METHODS OF HOMING MOLECULES TO LUNG USING MEMBRANE DIPEPTIDASE

(75) Inventors: Daniel Rajotte, Del Mar, CA (US); Renata Pasqualini, Solana Beach, CA (US); Erkki Ruoslahti, Rancho Santa Fe, CA (US)

(73) Assignee: The Burnham Institute, San Diego, CA (US)

( * ) Notice: Subject to any disclaimer, the term of this patent is extended or adjusted under 35 U.S.C. 154(b) by 288 days.

(21) Appl. No.: 09/676,475

(22) Filed: Sep. 29, 2000

Related U.S. Application Data

(60) Division of application No. 09/258,754, filed on Feb. 26, 1999, now Pat. No. 6,174,687, which is a continuation-in-part of application No. 09/042,107, filed on Mar. 13, 1998, now Pat. No. 6,232,287.

(51) Int. Cl.$^7$ .................. A61K 38/00; A61K 31/215; C12Q 1/37

(52) U.S. Cl. ..................... 514/2; 514/507; 435/24

(58) Field of Search ................. 435/24; 514/2, 514/507; 530/327, 328

(56) References Cited

U.S. PATENT DOCUMENTS

| | | | |
|---|---|---|---|
| 4,406,902 A | 9/1983 | Ashton et al. | |
| 4,616,038 A | 10/1986 | Kahan et al. | |
| 5,061,730 A | 10/1991 | Uchida et al. | |
| 5,145,990 A | 9/1992 | Parsons et al. | |
| 5,622,699 A | 4/1997 | Ruoslahti et al. | |

FOREIGN PATENT DOCUMENTS

| | | | |
|---|---|---|---|
| WO | WO 97/10507 | | 3/1997 |
| WO | WO 97/26918 | | 7/1997 |
| WO | WO 98/10795 | | 3/1998 |
| WO | WO 0220722 | * | 3/2002 |

OTHER PUBLICATIONS

Adachi et al., "Importance of Glu–125 in the catalytic activity of human renal dipeptidase," *Biochim. Biophys. Acta* 1163:42–48 (1993).
Adachi et al., "Primary Structure of Human Microsomal Dipeptidase Deduced from Molecular Cloning," *J. Biol. Chem.* 265:3992–3995 (1990).
Adachi et al., "Primary structure of rat renal dipeptidase and expression of its mRNA in rat tissues and COS–1 cells," *Biochim. Biophys. Acta* 1132:311–314 (1992).
Alton and Geddes, "Prospects for respiratory gene therapy," *Brit. J. Hosp. Medicine* 58:47–49 (1997).
An et al., "Molecular cloning of sheep lung dipeptidase: a glycosyl phosphatylinositol–anchored ectoenzyme that converts leukotriene $D_4$ to leukotriene $E_4$," *Biochim. Biophys. Acta* 1226:337–340 (1994).

Arap et al., "Cancer Treatment by Targeted Drug Delivery to Tumor Vasculature in a Mouse Model," *Science* 279:377–380 (1998).
Campbell et al., "β–Lactamase Activity of Purified and Partially Characterized Human Renal Dipeptidase," *J. Biol. Chem.* 259:14586–14590 (1984).
Cheng et al., "Lung Endothelial Dipeptidyl Peptidase IV Promotes Adhesion and Metastasis of Rat Breast Cancer Cells via Tumor Cell Surface–associated Fibronectin," *J. Biol. Chem.* 273:24207–24215 (1998).
Elble et al., "Cloning and Characterization of Lung–Endothelial Cell Adhesion Molecule–1 Suggest It Is an Endothelial Chloride Channel," *J. Biol. Chem.* 272:27853–27861 (1997).
GenBank Accession No. S27204 (Dec. 6, 1996).
GenBank Accession No. D13139 (Feb. 3, 1999).
Habib et al., "Four Distinct Membrane–bound Dipeptidase RNAs Are Differentially Expressed and Show Discordant Regulation with Y–Glutamyl," *J. Biol. Chem.* 271:16273–16280 (1996).
Habib et al., "Leukotriene $D_4$ and cystinyl–bis–glycine metabolism in membrane–bound dipeptidase–deficient mice," *Proc. Natl. Acad. Sci., USA* 95:4859–4863 (1998).
Hashimoto et al., "Studies on New Dehydropeptidase Inhibitors," *J. Antibiotics* XLIII:281–285 (1990).
Heywood and Hooper, "Development and Application of a Fluorometric Assay for Mammalian Membrane Dipeptidase," *Analytical Biochemistry* 226:10–14 (1995).
Hirota et al., "Characterization of dehydropeptidase I in the rat lung," *Eur. J. Biochem.* 160:521–525 (1986).
Hooper et al., "Identification of membrane dipeptidase as a major glycosyl–phosphatidylinositol–anchored protein of the pancreatic zymogen granule membrane, and evidence for its release by phospholipase A," *Biochem. J.* 324:151–157 (1997).
Igarashi and Karniski, "Cloning of cDNAs encoding a rabbit renal brush border membrane protein immunologically related to band 3," *Biochem. J.* 280:71–78 (1991).
Inamura et al., "Differential Tissue Expression of Immunoreactive Dehydropeptidase I, a Peptidyl Leukotriene Metabolizing Enzyme," *Prostaglandins Leukotrienes and Essential Fatty Acids* 50:85–92 (1994).

(List continued on next page.)

Primary Examiner—Majorie A. Moran
(74) Attorney, Agent, or Firm—McDermott Will & Emery

(57) ABSTRACT

The present invention provides a method of identifying a membrane dipeptidase (MDP)-binding homing molecule that selectively homes to lung endothelium. The method includes the steps of contacting MDP with one or more molecules; and determining specific binding of a molecule to the MDP, where the presence of specific binding identifies the molecule as a MDP-binding homing molecule that selectively homes to lung endothelium. Such MDP-binding homing molecules can be linked to a moiety and, when administered to a subject as a conjugate, can selectively direct the moiety to lung endothelium in the subject.

11 Claims, 11 Drawing Sheets

OTHER PUBLICATIONS

Johnson et al., "Lung Endothelial Dipeptidyl Peptidase IV Is an Adhesion Molecule for Lung–metastatic Rat Breast and Prostate Carcinoma Cells," *J. Cell Biol.* 121: 1423–1432 (1993).

Keynan et al., "Identification by site–directed mutagensis of three essential histidine residues in membrane dipeptidase, a novel mammalian zinc peptidase," *Biochem. J.* 326:47–51 (1997).

Keynan et al., "Site–Directed Mutagenesis of Conserved Cysteine Residues in Porcine Membrane Dipeptidase," *Biochemistry* 35:12511–12517 (1996).

Keynan et al., in Hooper (Ed.) *Zinc Metalloproteases in Health and Disease* Taylor and Francis, London pp. 285–309 (1996).

Keynan et al., "Directed mutagenesis of pig renal membrane dipeptidase," *FEBS Letters.* 349:50–54 (1994).

Koivunen et al., "Isolation of a Highly Specific Ligand for the $\alpha_5\beta_1$ Integrin from a Phage Display Library," *J. Cell Biol.* 124:373–380 (1994).

Littlewood et al., "Ectoenzymes of the kidney microvillar membrane," *Biochem. J.* 257:361–367 (1989).

Norrby et al., "Urinary recovery of N–formimidoyl thienamycin (MK0787) as affected by coadministration of N–formimidoyl thienamycin dehydropeptidase inhibitors," *Antimicrob. Agents Chemother.* 23:300–307 (1983).

Parsons et al., "A New Class of Potent, Slowly Reversible Dehydropeptidase Inhibitors," *Biochemistry International* 23:1107–1115 (1991).

Pasqualini and Ruoslahti, "Organ targeting in vivo using phage display peptide libraries," *Nature* 380:364–366 (1996).

Polgren et al., "Identification of muscle homing sequences by using phage display libraries of peptides," *Tumor Biology* 18:77 (1977).

Rajotte et al., "Molecular Heterogeneity of the Vascular Endothelium Revealed by In Vivo Phage Display," *J. Clinical Invest.* 102:430–437 (1998).

Rosenfeld et al., "Adenovirus–Mediated Transfer of a Recombinant α1–Antitrypsin Gene to the Lung Epithelium in Vivo," *Science* 252:431–434 (1991).

Rosenfeld et al., "In Vivo Transfer of the Human Cystic Fibrosis Transmembrane Conductance Regulator Gene to the Airway Epithelium," *Cell* 68:143–155 (1992).

Satoh et al., "Purification and molecular cloning of mouse renal dipeptidase," *Biochim. Biophys. Acta* 1163:234–242 (1993).

Smith, "Pulmonary Metastasis," *Seminars Oncology Nurs.* 14:178–186 (1998).

Takase et al., "Studies on New Dehydropeptidase Inhibitors," *J. Antibiotics* XLIII:38–42 (1990).

Wood, "Cystic Fibrosis: 1997, " *Radiology* 204:1–10 (1997).

Yamaya et al., "Dipeptidase inhibitor and epithelial removal potentiate leukotriene $D_4$–induced human tracheal smooth muscle contraction," *Resp. Physiol.* 111:101–109 (1998).

Zhu et al., "Systemic Gene Expression After Intravenous DNA Delivery into Adult Mice," *Science* 261:209–211 (1993).

* cited by examiner

```
                -16          1                                                                          84
HUM   MWSGWWLWSLVAVCTADFFRDEAERIMRDSPVIDGHNDLPWQLLLDMFNNRLQDERANLTTLAGTHTNIPKLRAGFVGGQFWSVYTPCDTQNKDAVRRTLE
PIG   MWTSWWLWPLVAVCAADQFRDLAVRIMQDTPVIDGHNDLPWQLLNLFNNQLQDPGANLSSLAHTHTNIPKLLKAGFVGGQFWSAYVPCDTQNRDAVKRTLE
RAT   MLIWWFWSLLAICASDSFRNQAENIMRTTPVIDGHNDLPWQMLTLFNNQLRKSEANLSALAETHTNIPKLRAGFVGGQFWSAYMPCDTQNKDAVKRILE
MOU   MVIIWFWSLLAICASDSFRDQAVAIMRTTPVIDGHNDLPWQLLNLFNNQLLRPDADLNKLAQTHTNIPKLKAGFVGGQFWSAYMPCDTQNKDAVKRILE
RAB   MWTSWWLWPLVAVCTADSFLDQAVQILRVTPVIDGHNDLPWQLLNKFNNRLQDSRANLTVLADTHTNIPKLRAGFVGGQFWSAYTPCDTQNKDTVRRTLE

184
HUM   QMDVVHRMCRMYPETFLYVTSSAGIRQAFREGKVASLIGV[E]GGHSIDSSLGVLRALYQLGMRYLTLTHSCNTPWADNWLVDTGDSEPQSQGLSPFGQRVV
PIG   QIDVIQRMCQAYPETFACVTSSTGIRQAFREGKVASLVGVEGGHSIDSSLGVLRALYHLGMRYMTLTHSCNTPWADNWLVDTGDDKAQSQGLSHFGQSVV
RAT   QIDVIHRMCQLYPETFECVTNSSDILQAFRRGKVASLIGVEGGHLIDSSLGVLRTLYHLGMRYLTLTHNCNTPWADNWLVDKGDDEAESQGLSPFGKLVL
MOU   QMDVIHRMCQLYPETFMCVTNSSDILQAFRRGKVASLIGVEGGHLIDSSLGVLRTLYHLGMRYLTLTHNCNTPWADNWLVDRGDDEAESHGLSPFGKRLL
RAB   QMDVVHRMCQLYPETFLCCVTDSAGIQQAFREGKVASLIGVEGGHSIDSSLGVLRALYRLGMRYLTLTHNCNTPWADNWLVDRGDDEAQSGGLSVFGQRVV
```

Figure 9A

```
                                                                                            284                                                                                                   411
HUM  KELNRLGVLIDL AHVSVATMKATLQLSRAPVIFSH SSAYSVCASRRNVPDDVLRLVKQTDSLVMVNFYNNYISCTNKANLSQVADHLDHIKEVAGARAVG
PIG  KEMNRLGVMIDL AHVSVATMRAALKLSQAPVIFSHSSAYSVCAPVIFSHSHSSAYSVCPHRRNVPDDVLQLVKETGSLVMVNFYNDYVSCCSAKANLSQVADHLDHIKKVAGAAAVG
RAT  NEMNRLGVMIDL SHVSVATMKDALQLSKAPVIFSHSSAYSVCPHRRNVPDDVLQLVKSTNSLVMVNFYNQFVSCCSDSATLSQVADHLDHIKKVAGAGAVG
MOU  NEMTRLGVMIDL SHVSVATMKDALQISRAPVIFSHSSAYSLCPHRRNVPDDVLQLVMVFFSNFVSCSDSATLPQVADHLDHIKKVAGAGAVG
RAB  REMNRLGVMIDL AHVSVATMKAALQLSTAPVIFSHSSAFTVCAHKRNVPDDVLQLVKETGSLVMVNFYNDYVSCASEATLSQVADHLDYIKNVAGAAAVR

HUM  FGGDFDGVPRVPEGLEDVSKYPDLIAELLRRNWTEAEVKGALADNLLRVFEAVEQASNLTQAPEEEPIPLDQLGGSCRTHYGYSSGASSLHRWGLLLASLAPLVLCLSLL
PIG  FGGDYDGVSRVPSGLEDVSKYPDLVAELLRRQWTEAEVRGALADNLLRVFEAVEQASNHAQVPGEEPIPLGQLEASCRTNYGY-SAAPSLHLPPGSLLASLVPLLL-LSLP
RAT  LGGDYDGVTNLPVGLEDVSKYPDLIAELLRRNWTETEVRGLLAENLLRVFSAVELVSNIMQVPEEETIPVEKLDGSCRTFYGH-SRAPSIHLQIGALLASLASLVFSLHPL
MOU  LGGDYDGVTMLPVGLEDVSKYPDLIAELLRRNWTETEVRGLLADNLIRVFSEVELVSSNMQSPEEVPITLKELDGSCRTYYGY-SQAHSIHLQTGALVASLASLLFRLHLL
RAB  FGGDFDGVTRLPVGLEDVSKYPDLVAELLRRGWTEAEVRGALAENLLRVFREVEQVSNQAQVPEEEPISLEQLGGSCRTQYGY-SEAPSLHRRPGALLASLSLLLLSLGLL
```

Figure 9B

SEQUENCE LISTING

<160> NUMBER OF SEQ ID NOS: 452

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 1

Cys Gly Phe Glu Cys Val Arg Gln Cys Pro Glu Arg Cys
 1               5                  10

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 2

Cys Gly Phe Glu Leu Glu Thr Cys
 1               5

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 3

Cys Val Ala Leu Cys Arg Glu Ala Cys Gly Glu Gly Cys
 1               5                  10

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 4

Ser Trp Cys Glu Pro Gly Trp Cys Arg
 1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 5

Cys Ser Cys Phe Arg Asp Val Cys Cys
 1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 6

-continued

Cys Arg Asp Val Val Ser Val Ile Cys
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 7

Leu Ser Pro Pro Tyr Met Trp
1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 8

Gly Ile Gly Glu Val Glu Val Cys
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 9

Tyr Ser Gly Lys Trp Gly Lys
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 10

Glu Val Arg Ser Arg Leu Ser
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 11

Arg Val Gly Leu Val Ala Arg
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 12

Val Lys Ser Val Cys Arg Thr

```
<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 13

Cys Leu Ala Lys Glu Asn Val Val Cys
  1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 14

Cys Gly Glu Phe Lys Val Gly Cys
  1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 15

Cys Thr Leu Arg Asp Arg Asn Cys
  1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 16

Cys Ile Gly Glu Val Glu Val Cys
  1               5

<210> SEQ ID NO 17
<211> LENGTH: 23
<212> TYPE: PRT
<213> ORGANISM: Artificial Sequence
<220> FEATURE:
<221> NAME/KEY: SITE
<222> LOCATION: (1)..(10)
<223> OTHER INFORMATION: Xaa may be present or absent
<220> FEATURE:
<221> NAME/KEY: SITE
<222> LOCATION: (14)..(23)
<223> OTHER INFORMATION: Xaa may be present or absent.
<220> FEATURE:
<223> OTHER INFORMATION: Description of Artificial Sequence: Synthetic

<400> SEQUENCE: 17

Xaa Xaa Xaa Xaa Xaa Xaa Xaa Xaa Xaa Xaa Gly Phe Glu Xaa Xaa Xaa
  1               5                  10                  15

Xaa Xaa Xaa Xaa Xaa Xaa Xaa
             20
```

```
<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 18

Leu Cys Thr Ala Met Thr Glu
 1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 19

Gly Ile Ser Ala Leu Val Leu Ser
 1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 20

Cys Gly Lys Arg Tyr Arg Asn Cys
 1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 21

Ser Met Ser Ile Ala Arg Leu
 1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 22

Val Ser Phe Leu Glu Tyr Arg
 1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: UNSURE
<222> LOCATION: (1)..(2)
<223> OTHER INFORMATION: Unsure
<220> FEATURE:
<221> NAME/KEY: UNSURE
<222> LOCATION: (4)..(7)
<223> OTHER INFORMATION: Unsure
```

```
<220> FEATURE:
<221> NAME/KEY: UNSURE
<222> LOCATION: (8)
<223> OTHER INFORMATION: Unsure

<400> SEQUENCE: 23

Xaa Xaa Cys Xaa Xaa Xaa Xaa Cys Xaa
 1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: UNSURE
<222> LOCATION: (2)..(8)
<223> OTHER INFORMATION: Unsure

<400> SEQUENCE: 24

Cys Xaa Xaa Xaa Xaa Xaa Xaa Xaa Cys
 1               5

<210> SEQ ID NO 25
<211> LENGTH: 13
<212> TYPE: PRT
<213> ORGANISM: Artificial Sequence
<220> FEATURE:
<221> NAME/KEY: UNSURE
<222> LOCATION: (2)..(4)
<223> OTHER INFORMATION: Unsure
<220> FEATURE:
<221> NAME/KEY: UNSURE
<222> LOCATION: (6)..(8)
<223> OTHER INFORMATION: Unsure
<220> FEATURE:
<221> NAME/KEY: UNSURE
<222> LOCATION: (10)..(12)
<223> OTHER INFORMATION: Unsure
<220> FEATURE:
<223> OTHER INFORMATION: Description of Artificial Sequence: Synthetic

<400> SEQUENCE: 25

Cys Xaa Xaa Xaa Cys Xaa Xaa Xaa Cys Xaa Xaa Xaa Cys
 1               5                   10

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: UNSURE
<222> LOCATION: (2)..(7)
<223> OTHER INFORMATION: Unsure

<400> SEQUENCE: 26

Cys Xaa Xaa Xaa Xaa Xaa Xaa Cys
 1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 27
```

```
Leu Met Leu Pro Arg Ala Asp
  1               5
```

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 28

```
Leu Pro Arg Tyr Leu Leu Ser
  1               5
```

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: UNSURE
<222> LOCATION: (1)..(7)
<223> OTHER INFORMATION: individually selected amino acid

<400> SEQUENCE: 29

```
Xaa Xaa Xaa Xaa Xaa Xaa Xaa
  1               5
```

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: UNSURE
<222> LOCATION: (2)..(11)

<400> SEQUENCE: 30

```
Cys Xaa Xaa Xaa Xaa Xaa Xaa Xaa Xaa Xaa Xaa Cys
  1               5                  10
```

<210> SEQ ID NO 31
<211> LENGTH: 24
<212> TYPE: DNA
<213> ORGANISM: Artificial Sequence
<220> FEATURE:
<221> NAME/KEY: variation
<222> LOCATION: (4)..(21)
<223> OTHER INFORMATION: N is equal molar mixtures of A, C, G and T; K
      is equal molar mixtures of G and T.
<220> FEATURE:
<223> OTHER INFORMATION: Description of Artificial Sequence: Synthetic

<400> SEQUENCE: 31
tgtnnknnkn nknnknnknn ktgt                                    24

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 32

```
Cys Ile Lys Gly Asn Val Asn Cys
  1               5
```

```
<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 33

Cys Arg His Glu Ser Ser Ser Cys
  1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 34

Cys Leu Tyr Ile Asp Arg Arg Cys
  1               5

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 35

Cys Tyr Ser Leu Gly Ala Asp Cys
  1               5

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 36

Cys Asn Ser Asp Val Asp Leu Cys
  1               5

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 37

Cys Val Gly Asn Leu Ser Met Cys
  1               5

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 38

Cys Glu Lys Lys Leu Leu Tyr Cys
  1               5
```

```
<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 39

Cys Lys Gly Gln Arg Asp Phe Cys
  1               5

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 40

Cys Thr Phe Arg Asn Ala Ser Cys
  1               5

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 41

Cys Asn Met Gly Leu Thr Arg Cys
  1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 42

Cys His Glu Gly Tyr Leu Thr Cys
  1               5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 43

Cys Gly Thr Phe Gly Ala Arg Cys
  1               5

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 44

Cys Arg Ile Ser Ala His Pro Cys
  1               5

<210> SEQ ID NO 45
```

```
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 45

Cys Leu Arg Pro Tyr Leu Asn Cys
  1               5

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 46

Cys Ser Tyr Pro Lys Ile Leu Cys
  1               5

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 47

Cys Met Glu Leu Ser Lys Gln Cys
  1               5

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 48

Cys Ser Glu Pro Ser Gly Thr Cys
  1               5

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 49

Cys Gly Asn Glu Thr Leu Arg Cys
  1               5

<210> SEQ ID NO 50
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 50

Cys Thr Leu Ser Asn Arg Phe Cys
  1               5

<210> SEQ ID NO 51
<211> LENGTH: 8
```

```
<212> TYPE: PRT
<213> ORGANISM: Artificial Sequence
<220> FEATURE:
<223> OTHER INFORMATION: Description of Artificial Sequence: Synthetic

<400> SEQUENCE: 51

Cys Met Gly Ser Glu Tyr Trp Cys
 1               5

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 52

Cys Leu Phe Ser Asp Glu Asn Cys
 1               5

<210> SEQ ID NO 53
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 53

Cys Ala His Gln His Ile Gln Cys
 1               5

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 54

Cys Lys Gly Gln Gly Asp Trp Cys
 1               5

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 55

Cys Ala Gln Asn Met Leu Cys Cys
 1               5

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 56

Cys Trp Arg Gly Asp Arg Lys Ile Cys
 1               5

<210> SEQ ID NO 57
<211> LENGTH: 9
<212> TYPE: PRT
```

```
<213> ORGANISM: Artificial Sequence
<220> FEATURE:
<223> OTHER INFORMATION: Description of Artificial Sequence: Synthetic

<400> SEQUENCE: 57

Cys Ile Phe Arg Glu Ala Asn Val Cys
 1               5

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 58

Cys Arg Thr His Gly Tyr Gln Gly Cys
 1               5

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 59

Cys Glu Arg Val Val Gly Ser Ser Cys
 1               5

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 60

Cys Lys Thr Asn His Met Glu Ser Cys
 1               5

<210> SEQ ID NO 61
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 61

Cys Tyr Glu Glu Lys Ser Gln Ser Cys
 1               5

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 62

Cys Lys Asp Ser Ala Met Thr Ile Cys
 1               5

<210> SEQ ID NO 63
<211> LENGTH: 9
<212> TYPE: PRT
<213> ORGANISM: Artificial Sequence
```

```
<220> FEATURE:
<223> OTHER INFORMATION: Description of Artificial Sequence: Synthetic

<400> SEQUENCE: 63

Cys Thr Arg Ser Thr Asn Thr Gly Cys
 1               5

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 64

Cys Met Ser Trp Asp Ala Val Ser Cys
 1               5

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 65

Cys Lys Trp Ser Arg Leu His Ser Cys
 1               5

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 66

Cys Met Ser Pro Gln Arg Ser Asp Cys
 1               5

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 67

Cys Leu His Ser Pro Arg Ser Lys Cys
 1               5

<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 68

Cys Pro Gln Asp Ile Arg Arg Asn Cys
 1               5

<210> SEQ ID NO 69
<211> LENGTH: 9
<212> TYPE: PRT
<213> ORGANISM: Artificial Sequence
<220> FEATURE:
```

<223> OTHER INFORMATION: Description of Artificial Sequence: Synthetic

<400> SEQUENCE: 69

Cys Leu Tyr Thr Lys Glu Gln Arg Cys
 1               5

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 70

Cys Gln Thr Arg Asn Phe Ala Gln Cys
 1               5

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 71

Cys Thr Gly His Leu Ser Thr Asp Cys
 1               5

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 72

Cys Gln Asp Leu Asn Ile Met Gln Cys
 1               5

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 73

Thr Arg Arg Thr Asn Asn Pro Leu Thr
 1               5

<210> SEQ ID NO 74
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 74

Cys Gly Tyr Ile Asp Pro Asn Arg Ile Ser Gln Cys
 1               5                  10

<210> SEQ ID NO 75
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 75

Cys Thr Val Asn Glu Ala Tyr Lys Thr Arg Met Cys
 1               5                  10

<210> SEQ ID NO 76
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 76

Cys Arg Leu Arg Ser Tyr Gly Thr Leu Ser Leu Cys
 1               5                  10

<210> SEQ ID NO 77
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 77

Cys Ala Gly Thr Cys Ala Thr Gly Cys Asn Gly Val Cys
 1               5                  10

<210> SEQ ID NO 78
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 78

Cys Ala Asp Tyr Asp Leu Ala Leu Gly Leu Met Cys
 1               5                  10

<210> SEQ ID NO 79
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 79

Cys Pro Lys Ala Arg Pro Ala Pro Gln Tyr Lys Cys
 1               5                  10

<210> SEQ ID NO 80
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 80

Cys Ser Ser His Gln Gly Gly Phe Gln His Gly Cys
 1               5                  10

<210> SEQ ID NO 81
<211> LENGTH: 12
<212> TYPE: PRT
<213> ORGANISM: Artificial Sequence
<220> FEATURE:
<223> OTHER INFORMATION: Description of Artificial Sequence: Synthetic -continued

```
<400> SEQUENCE: 81

Cys Gln Glu Thr Arg Thr Glu Gly Arg Lys Lys Cys
  1               5                  10

<210> SEQ ID NO 82
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 82

Cys Arg Pro Trp His Asn Gln Ala His Thr Glu Cys
  1               5                  10

<210> SEQ ID NO 83
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 83

Cys Ser Phe Gly Thr His Asp Thr Glu Pro His Cys
  1               5                  10

<210> SEQ ID NO 84
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 84

Cys Ser Glu Ala Ala Ser Arg Met Ile Gly Val Cys
  1               5                  10

<210> SEQ ID NO 85
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 85

Cys Trp Glu Glu His Pro Ser Ile Lys Trp Trp Cys
  1               5                  10

<210> SEQ ID NO 86
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 86

Cys Trp Asp Ala Asp Gln Ile Phe Gly Ile Lys Cys
  1               5                  10

<210> SEQ ID NO 87
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 87
```

```
Cys Val Asp Ser Gln Ser Met Lys Gly Leu Val Cys
  1               5                  10
```

<210> SEQ ID NO 88
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 88

```
Cys Arg Leu Gln Thr Met Gly Gln Gly Gln Ser Cys
  1               5                  10
```

<210> SEQ ID NO 89
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 89

```
Cys Arg Pro Ala Gln Arg Asp Ala Gly Thr Ser Cys
  1               5                  10
```

<210> SEQ ID NO 90
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 90

```
Cys Gly Gly Arg Asp Arg Gly Thr Tyr Gly Pro Cys
  1               5                  10
```

<210> SEQ ID NO 91
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 91

```
Cys Gly Glu Val Ala Ser Asn Glu Arg Ile Gln Cys
  1               5                  10
```

<210> SEQ ID NO 92
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 92

```
Cys Asn Ser Lys Ser Ser Ala Glu Leu Glu Lys Cys
  1               5                  10
```

<210> SEQ ID NO 93
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 93

Cys Val Leu Asn Phe Lys Asn Gln Ala Arg Asp Cys
 1               5                  10

<210> SEQ ID NO 94
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 94

Cys Arg Gly Lys Pro Leu Ala Asn Phe Glu Asp Cys
 1               5                  10

<210> SEQ ID NO 95
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 95

Cys Glu Gly His Ser Met Arg Gly Tyr Gly Leu Cys
 1               5                  10

<210> SEQ ID NO 96
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 96

Cys Arg Asp Arg Gly Asp Arg Met Lys Ser Leu Cys
 1               5                  10

<210> SEQ ID NO 97
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 97

Cys Asp Asn Thr Cys Thr Tyr Gly Val Asp Asp Cys
 1               5                  10

<210> SEQ ID NO 98
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 98

Cys Ser Ala His Ser Gln Glu Met Asn Val Asn Cys
 1               5                  10

<210> SEQ ID NO 99
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 99

Cys Gly Ala Ala Cys Gly Val Gly Cys Arg Gly Arg Cys

```
                1               5                  10

<210> SEQ ID NO 100
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 100

Cys Leu Val Gly Cys Arg Leu Ser Cys Gly Gly Glu Cys
 1               5                  10

<210> SEQ ID NO 101
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 101

Cys Arg Ser Gly Cys Val Glu Gly Cys Gly Gly Arg Cys
 1               5                  10

<210> SEQ ID NO 102
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 102

Cys Ile Ala Arg Cys Gly Gly Ala Cys Gly Arg His Cys
 1               5                  10

<210> SEQ ID NO 103
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 103

Cys Gly Gly Glu Cys Gly Trp Glu Cys Glu Val Ser Cys
 1               5                  10

<210> SEQ ID NO 104
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 104

Cys Gly Val Gly Cys Pro Gly Leu Cys Gly Gly Ala Cys
 1               5                  10

<210> SEQ ID NO 105
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 105

Cys Lys Trp Leu Cys Leu Leu Leu Cys Ala Val Ala Cys
 1               5                  10
```

<210> SEQ ID NO 106
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 106

Cys Ser Glu Gly Cys Gly Pro Val Cys Trp Pro Glu Cys
 1               5                  10

<210> SEQ ID NO 107
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 107

Cys Gly Ala Ala Cys Gly Val Gly Cys Gly Gly Arg Cys
 1               5                  10

<210> SEQ ID NO 108
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 108

Cys Ser Gly Ser Cys Arg Arg Gly Cys Gly Ile Asp Cys
 1               5                  10

<210> SEQ ID NO 109
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 109

Cys Gly Ala Ser Cys Ala Leu Gly Cys Arg Ala Tyr Cys
 1               5                  10

<210> SEQ ID NO 110
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 110

Cys Asp Thr Ser Cys Glu Asn Asn Cys Gln Gly Pro Cys
 1               5                  10

<210> SEQ ID NO 111
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 111

Cys Ser Arg Gln Cys Arg Gly Ala Cys Gly Gln Pro Cys
 1               5                  10

```
<210> SEQ ID NO 112
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 112

Cys Tyr Trp Trp Cys Asp Gly Val Cys Ala Leu Gln Cys
 1               5                  10

<210> SEQ ID NO 113
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 113

Cys Ala Gly Gly Cys Ala Val Arg Cys Gly Gly Thr Cys
 1               5                  10

<210> SEQ ID NO 114
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 114

Cys Gly Gly Ala Cys Gly Gly Val Cys Thr Gly Gly Cys
 1               5                  10

<210> SEQ ID NO 115
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 115

Cys Gly Arg Pro Cys Val Gly Glu Cys Arg Met Gly Cys
 1               5                  10

<210> SEQ ID NO 116
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 116

Cys Leu Val Gly Cys Glu Val Gly Cys Ser Pro Ala Cys
 1               5                  10

<210> SEQ ID NO 117
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 117

Cys Pro Arg Thr Cys Gly Ala Ala Cys Ala Ser Pro Cys
 1               5                  10
```

<210> SEQ ID NO 118
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 118

Cys Arg Gly Asp Cys Gly Ile Gly Cys Arg Arg Leu Cys
 1               5                  10

<210> SEQ ID NO 119
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 119

Glu Ile Cys Gln Leu Gly Ser Cys Thr
 1               5

<210> SEQ ID NO 120
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 120

Trp Arg Cys Glu Gly Phe Asn Cys Gln
 1               5

<210> SEQ ID NO 121
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 121

Arg Lys Cys Leu Arg Pro Asp Cys Gly
 1               5

<210> SEQ ID NO 122
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 122

Leu Ala Cys Phe Val Thr Gly Cys Leu
 1               5

<210> SEQ ID NO 123
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 123

Gly Leu Cys Asn Gly Ala Thr Cys Met
 1               5

<210> SEQ ID NO 124

```
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 124

Asp Met Cys Trp Leu Ile Gly Cys Gly
 1               5

<210> SEQ ID NO 125
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 125

Ser Gly Cys Arg Thr Met Val Cys Val
 1               5

<210> SEQ ID NO 126
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 126

Gln Arg Cys Pro Arg Ser Phe Cys Leu
 1               5

<210> SEQ ID NO 127
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 127

Leu Ser Cys Ala Pro Val Ile Cys Gly
 1               5

<210> SEQ ID NO 128
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 128

Arg Glu Cys Thr Asn Glu Ile Cys Tyr
 1               5

<210> SEQ ID NO 129
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 129

Asn Glu Cys Leu Met Ile Ser Cys Arg
 1               5

<210> SEQ ID NO 130
<211> LENGTH: 9
```

```
<212> TYPE: PRT
<213> ORGANISM: Artificial Sequence
<220> FEATURE:
<223> OTHER INFORMATION: Description of Artificial Sequence: Synthetic

<400> SEQUENCE: 130

Ser Cys Val Phe Cys Asp Trp Leu Ser
 1               5

<210> SEQ ID NO 131
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 131

Trp Ala Cys Glu Glu Leu Ser Cys Phe
 1               5

<210> SEQ ID NO 132
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 132

Gln Asn Cys Pro Val Thr Arg Cys Val
 1               5

<210> SEQ ID NO 133
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 133

Cys Ala Thr Leu Thr Asn Asp Glu Cys
 1               5

<210> SEQ ID NO 134
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 134

Cys Asp Asn Arg Glu Met Ser Cys
 1               5

<210> SEQ ID NO 135
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 135

Cys Phe Met Asp His Ser Asn Cys
 1               5

<210> SEQ ID NO 136
<211> LENGTH: 8
<212> TYPE: PRT
```

```
<213> ORGANISM: Artificial Sequence
<220> FEATURE:
<223> OTHER INFORMATION: Description of Artificial Sequence: Synthetic

<400> SEQUENCE: 136

Cys Gly Glu Tyr Gly Arg Glu Cys
 1               5

<210> SEQ ID NO 137
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 137

Cys His Met Lys Arg Asp Arg Thr Cys
 1               5

<210> SEQ ID NO 138
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 138

Cys Lys Lys Arg Leu Leu Asn Val Cys
 1               5

<210> SEQ ID NO 139
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 139

Cys Leu Asp Tyr His Pro Lys Cys
 1               5

<210> SEQ ID NO 140
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 140

Cys Met Thr Gly Arg Val Thr Cys
 1               5

<210> SEQ ID NO 141
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 141

Cys Asn Lys Ile Val Arg Arg Cys
 1               5

<210> SEQ ID NO 142
<211> LENGTH: 8
<212> TYPE: PRT
<213> ORGANISM: Artificial Sequence
```

```
<220> FEATURE:
<223> OTHER INFORMATION: Description of Artificial Sequence: Synthetic

<400> SEQUENCE: 142

Cys Pro Asp Leu Leu Val Ala Cys
 1               5

<210> SEQ ID NO 143
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 143

Cys Ser Asp Thr Gln Ser Ile Gly Cys
 1               5

<210> SEQ ID NO 144
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 144

Cys Ser Lys Ala Tyr Asp Leu Ala Cys
 1               5

<210> SEQ ID NO 145
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 145

Cys Ser Lys Lys Gly Pro Ser Tyr Cys
 1               5

<210> SEQ ID NO 146
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 146

Cys Thr Leu Lys His Thr Ala Met Cys
 1               5

<210> SEQ ID NO 147
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 147

Cys Thr Gln His Ile Ala Asn Cys
 1               5

<210> SEQ ID NO 148
<211> LENGTH: 8
<212> TYPE: PRT
<213> ORGANISM: Artificial Sequence
<220> FEATURE:
```

<223> OTHER INFORMATION: Description of Artificial Sequence: Synthetic

<400> SEQUENCE: 148

Cys Thr Thr Glu Ile Asp Tyr Cys
 1               5

<210> SEQ ID NO 149
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 149

Cys Val Gly Arg Ser Gly Glu Leu Cys
 1               5

<210> SEQ ID NO 150
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 150

Tyr Ala Gly Phe Phe Leu Val
 1               5

<210> SEQ ID NO 151
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 151

Arg Ser Gly Ala Arg Ser Ser
 1               5

<210> SEQ ID NO 152
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 152

Cys Val Glu Ser Thr Val Ala
 1               5

<210> SEQ ID NO 153
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 153

Ser Arg Arg Gln Pro Leu Ser
 1               5

<210> SEQ ID NO 154
<211> LENGTH: 7
<212> TYPE: PRT
<213> ORGANISM: Artificial Sequence
<220> FEATURE:
<223> OTHER INFORMATION: Description of Artificial Sequence: Synthetic

```
<400> SEQUENCE: 154

Ser Lys Val Trp Leu Leu Leu
  1               5

<210> SEQ ID NO 155
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 155

Gln Val Arg Arg Val Pro Glu
  1               5

<210> SEQ ID NO 156
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 156

Tyr Ser Gly Lys Trp Gly Trp
  1               5

<210> SEQ ID NO 157
<211> LENGTH: 6
<212> TYPE: PRT
<213> ORGANISM: Artificial Sequence
<220> FEATURE:
<223> OTHER INFORMATION: Description of Artificial Sequence: Synthetic

<400> SEQUENCE: 157

Met Val Gln Ser Val Gly
  1               5

<210> SEQ ID NO 158
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 158

Leu Arg Ala Val Gly Arg Ala
  1               5

<210> SEQ ID NO 159
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 159

Met Ser Pro Gln Leu Ala Thr
  1               5

<210> SEQ ID NO 160
<211> LENGTH: 7
<212> TYPE: PRT
<213> ORGANISM: Artificial Sequence
<220> FEATURE:
<223> OTHER INFORMATION: Description of Artificial Sequence: Synthetic
```

```
<400> SEQUENCE: 160

Gly Ala Val Leu Pro Gly Glu
 1               5

<210> SEQ ID NO 161
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 161

Trp Ile Glu Glu Ala Glu Arg
 1               5

<210> SEQ ID NO 162
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 162

Leu Val Ser Glu Gln Leu Arg
 1               5

<210> SEQ ID NO 163
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 163

Arg Gly Asp Arg Pro Pro Tyr
 1               5

<210> SEQ ID NO 164
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 164

Val Arg Arg Gly Ser Pro Gln
 1               5

<210> SEQ ID NO 165
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 165

Arg Val Arg Gly Pro Glu Arg
 1               5

<210> SEQ ID NO 166
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 166
```

```
Gly Ile Ser Ala Val Leu Ser
  1               5

<210> SEQ ID NO 167
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 167

Gly Gly Arg Gly Ser Trp Glu
  1               5

<210> SEQ ID NO 168
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 168

Gly Val Ser Ala Ser Asp Trp
  1               5

<210> SEQ ID NO 169
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 169

Phe Arg Val Arg Gly Ser Pro
  1               5

<210> SEQ ID NO 170
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 170

Ser Arg Leu Ser Gly Gly Thr
  1               5

<210> SEQ ID NO 171
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 171

Trp Glu Leu Val Ala Arg Ser
  1               5

<210> SEQ ID NO 172
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 172
```

```
Met Arg Arg Asp Glu Gln Arg
  1               5

<210> SEQ ID NO 173
<211> LENGTH: 6
<212> TYPE: PRT
<213> ORGANISM: Artificial Sequence
<220> FEATURE:
<223> OTHER INFORMATION: Description of Artificial Sequence: Synthetic

<400> SEQUENCE: 173

Gly Cys Arg Cys Trp Ala
  1               5

<210> SEQ ID NO 174
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 174

Cys Tyr Ala Asp Cys Glu Gly Thr Cys Gly Met Val Cys
  1               5                  10

<210> SEQ ID NO 175
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 175

Cys Trp Asn Ile Cys Pro Gly Gly Cys Arg Ala Leu Cys
  1               5                  10

<210> SEQ ID NO 176
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 176

Gly Pro Gly Cys Glu Glu Glu Cys Gln Pro Ala Cys
  1               5                  10

<210> SEQ ID NO 177
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 177

Cys Lys Gly Thr Cys Val Leu Gly Cys Ser Glu Glu Cys
  1               5                  10

<210> SEQ ID NO 178
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 178

Cys Ser Thr Leu Cys Gly Leu Arg Cys Met Gly Thr Cys
```

<210> SEQ ID NO 179
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 179

Cys Met Pro Arg Cys Gly Val Asn Cys Lys Trp Ala Cys
 1               5                  10

<210> SEQ ID NO 180
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 180

Cys Val Gly Ala Cys Asp Leu Lys Cys Thr Gly Gly Cys
 1               5                  10

<210> SEQ ID NO 181
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 181

Cys Ser Ser Gly Cys Ser Lys Asn Cys Leu Glu Met Cys
 1               5                  10

<210> SEQ ID NO 182
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 182

Cys Gly Arg Pro Cys Arg Gly Gly Cys Ala Ala Ser Cys
 1               5                  10

<210> SEQ ID NO 183
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 183

Cys Gln Gly Gly Cys Gly Val Ser Cys Pro Ile Phe Cys
 1               5                  10

<210> SEQ ID NO 184
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 184

Cys Ala Val Arg Cys Asp Gly Ser Cys Val Pro Glu Cys
 1               5                  10

```
<210> SEQ ID NO 185
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 185

Cys Gly Phe Gly Cys Ser Gly Ser Cys Gln Met Gln Cys
 1               5                  10

<210> SEQ ID NO 186
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 186

Cys Arg Val Val Cys Ala Asp Gly Cys Arg Phe Ile Cys
 1               5                  10

<210> SEQ ID NO 187
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 187

Cys Thr Met Gly Cys Thr Ala Gly Cys Ala Phe Ala Cys
 1               5                  10

<210> SEQ ID NO 188
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 188

Cys Glu Gly Lys Cys Gly Leu Thr Cys Glu Cys Thr Cys
 1               5                  10

<210> SEQ ID NO 189
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 189

Cys Asn Gln Gly Cys Ser Gly Ser Cys Asp Val Met Cys
 1               5                  10

<210> SEQ ID NO 190
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 190

Cys Ala Ser Gly Cys Ser Glu Ser Cys Tyr Val Gly Cys
 1               5                  10
```

```
<210> SEQ ID NO 191
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 191

Cys Gly Gly Gly Cys Gln Trp Gly Cys Ala Gly Glu Cys
 1               5                  10

<210> SEQ ID NO 192
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 192

Cys Ser Val Arg Cys Lys Ser Val Cys Ile Gly Leu Cys
 1               5                  10

<210> SEQ ID NO 193
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 193

Cys Pro Ser Asn Cys Val Ala Leu Cys Thr Ser Gly Cys
 1               5                  10

<210> SEQ ID NO 194
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 194

Cys Val Glu Gly Cys Ser Ser Gly Cys Gly Pro Gly Cys
 1               5                  10

<210> SEQ ID NO 195
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 195

Cys Arg Val Val Cys Ala Asp Gly Cys Arg Leu Ile Cys
 1               5                  10

<210> SEQ ID NO 196
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 196

Gly Ser Thr Leu Cys Gly Leu Arg Cys Met Gly Thr Cys
 1               5                  10
```

```
<210> SEQ ID NO 197
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 197

Cys Phe Thr Phe Cys Glu Tyr His Cys Gln Leu Thr Cys
 1               5                  10

<210> SEQ ID NO 198
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 198

Cys Arg Arg Ile Trp Tyr Ala Val Cys
 1               5

<210> SEQ ID NO 199
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 199

Cys Ser Ala Tyr Thr Thr Ser Pro Cys
 1               5

<210> SEQ ID NO 200
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 200

Cys Thr Asp Lys Ser Trp Pro Cys
 1               5

<210> SEQ ID NO 201
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 201

Cys Thr Asp Asn Arg Val Gly Ser
 1               5

<210> SEQ ID NO 202
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 202

Cys Thr Ile Ala Asp Phe Pro Cys
 1               5

<210> SEQ ID NO 203
```

```
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 203

Cys Thr Ser Asp Ile Ser Trp Trp Asp Tyr Lys Cys
 1               5                  10

<210> SEQ ID NO 204
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 204

Cys Thr Val Asp Asn Glu Leu Cys
 1               5

<210> SEQ ID NO 205
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 205

Cys Val Gly Asp Cys Ile Gly Ser Cys Trp Met Phe Cys
 1               5                  10

<210> SEQ ID NO 206
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 206

Cys Val Lys Phe Thr Tyr Asp Cys
 1               5

<210> SEQ ID NO 207
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 207

Cys Val Ser Gly His Leu Asn Cys
 1               5

<210> SEQ ID NO 208
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 208

Cys Tyr Gly Glu Ser Gln Gln Met Cys
 1               5

<210> SEQ ID NO 209
<211> LENGTH: 9
```

```
<212> TYPE: PRT
<213> ORGANISM: Artificial Sequence
<220> FEATURE:
<223> OTHER INFORMATION: Description of Artificial Sequence: Synthetic

<400> SEQUENCE: 209

Cys Tyr Thr Gly Glu Thr Trp Thr Cys
  1               5

<210> SEQ ID NO 210
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 210

Cys Ala Val Ser Ile Pro Arg Cys
  1               5

<210> SEQ ID NO 211
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 211

Cys Asp Cys Arg Gly Asp Cys Phe Cys
  1               5

<210> SEQ ID NO 212
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 212

Cys Asp Ser Leu Cys Gly Gly Ala Cys Ala Ala Arg Cys
  1               5                  10

<210> SEQ ID NO 213
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 213

Cys Glu Arg Ser Gln Ser Lys Gly Val His His Cys
  1               5                  10

<210> SEQ ID NO 214
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 214

Cys Phe Lys Ser Thr Leu Leu Cys
  1               5

<210> SEQ ID NO 215
<211> LENGTH: 8
<212> TYPE: PRT
```

```
<213> ORGANISM: Artificial Sequence
<220> FEATURE:
<223> OTHER INFORMATION: Description of Artificial Sequence: Synthetic

<400> SEQUENCE: 215

Cys Phe Trp His Asn Arg Ala Cys
 1               5

<210> SEQ ID NO 216
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 216

Cys Gly Asp Val Cys Pro Ser Glu Cys Pro Gly Trp Cys
 1               5                  10

<210> SEQ ID NO 217
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 217

Cys Gly Leu Asp Cys Leu Gly Asp Cys Ser Gly Ala Cys
 1               5                  10

<210> SEQ ID NO 218
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 218

Cys Gly Pro Gly Tyr Gln Ala Gln Cys Ser Leu Arg Cys
 1               5                  10

<210> SEQ ID NO 219
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 219

Cys Gly Ser His Cys Gly Gln Leu Cys Lys Ser Leu Cys
 1               5                  10

<210> SEQ ID NO 220
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 220

Cys His Met Gly Cys Val Ser Pro Cys Ala Tyr Val Cys
 1               5                  10

<210> SEQ ID NO 221
<211> LENGTH: 9
<212> TYPE: PRT
<213> ORGANISM: Artificial Sequence
```

```
<220> FEATURE:
<223> OTHER INFORMATION: Description of Artificial Sequence: Synthetic

<400> SEQUENCE: 221

Cys Ile Leu Ser Tyr Asp Asn Pro Cys
 1               5

<210> SEQ ID NO 222
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 222

Cys Ile Ser Arg Pro Tyr Phe Cys
 1               5

<210> SEQ ID NO 223
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 223

Cys Lys Glu Arg Leu Glu Tyr Thr Arg Gly Val Cys
 1               5                  10

<210> SEQ ID NO 224
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 224

Cys Lys Glu Arg Pro Ser Asn Gly Leu Ser Ala Cys
 1               5                  10

<210> SEQ ID NO 225
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 225

Cys Lys Pro Phe Arg Thr Glu Cys
 1               5

<210> SEQ ID NO 226
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 226

Cys Lys Ser Gly Cys Gly Val Ala Cys Arg His Met Cys
 1               5                  10

<210> SEQ ID NO 227
<211> LENGTH: 9
<212> TYPE: PRT
<213> ORGANISM: Artificial Sequence
<220> FEATURE:
```

<223> OTHER INFORMATION: Description of Artificial Sequence: Synthetic

<400> SEQUENCE: 227

Cys Leu Lys Pro Gly Gly Gln Glu Cys
 1               5

<210> SEQ ID NO 228
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 228

Cys Met Asp Ser Gln Ser Ser Cys
 1               5

<210> SEQ ID NO 229
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 229

Cys Met Asn Ile Leu Ser Gly Cys
 1               5

<210> SEQ ID NO 230
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 230

Cys Asn Ile Pro Val Thr Thr Pro Ile Phe Gly Cys
 1               5                  10

<210> SEQ ID NO 231
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 231

Cys Asn Gln Arg Thr Asn Arg Glu Ser Gly Asn Cys
 1               5                  10

<210> SEQ ID NO 232
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 232

Cys Asn Arg Lys Asn Ser Asn Glu Gln Arg Ala Cys
 1               5                  10

<210> SEQ ID NO 233
<211> LENGTH: 8
<212> TYPE: PRT
<213> ORGANISM: Artificial Sequence
<220> FEATURE:
<223> OTHER INFORMATION: Description of Artificial Sequence: Synthetic

```
<400> SEQUENCE: 233

Cys Asn Arg Met Glu Met Pro Cys
  1               5

<210> SEQ ID NO 234
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 234

Cys Gln Ile Arg Pro Ile Asp Lys Cys
  1               5

<210> SEQ ID NO 235
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 235

Cys Ala Ile Asp Ile Gly Gly Ala Cys
  1               5

<210> SEQ ID NO 236
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 236

Cys Gly Arg Phe Asp Thr Ala Pro Gln Arg Gly Cys
  1               5                  10

<210> SEQ ID NO 237
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 237

Cys Lys Arg Ala Asn Arg Leu Ser Cys
  1               5

<210> SEQ ID NO 238
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 238

Cys Leu Leu Asn Tyr Thr Tyr Cys
  1               5

<210> SEQ ID NO 239
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
<400> SEQUENCE: 239

Cys Leu Asn Gly Leu Val Ser Met Cys
 1               5

<210> SEQ ID NO 240
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 240

Cys Met Ser Leu Gly Asn Asn Cys
 1               5

<210> SEQ ID NO 241
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 241

Cys Asn Arg Asn Arg Met Thr Pro Cys
 1               5

<210> SEQ ID NO 242
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 242

Cys Gln Ala Ser Ala Ser Asp His Cys
 1               5

<210> SEQ ID NO 243
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 243

Cys Gln Leu Ile Asn Ser Ser Pro Cys
 1               5

<210> SEQ ID NO 244
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 244

Cys Gln Arg Val Asn Ser Val Glu Asn Ala Ser Cys
 1               5                   10

<210> SEQ ID NO 245
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 245
```

Cys Arg Lys Glu His Tyr Pro Cys
 1               5

<210> SEQ ID NO 246
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 246

Cys Arg Arg His Met Glu Arg Cys
 1               5

<210> SEQ ID NO 247
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 247

Cys Ser Gly Arg Pro Phe Lys Tyr Cys
 1               5

<210> SEQ ID NO 248
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 248

Cys Thr His Leu Val Thr Leu Cys
 1               5

<210> SEQ ID NO 249
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 249

Cys Thr Ser Ser Pro Ala Tyr Asn Cys
 1               5

<210> SEQ ID NO 250
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 250

Cys Val Thr Ser Asn Leu Arg Val Cys
 1               5

<210> SEQ ID NO 251
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 251

Cys Trp Asp Ser Gly Ser His Ile Cys
1               5

<210> SEQ ID NO 252
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 252

Cys Glu Arg Ser His Gly Arg Leu Cys
1               5

<210> SEQ ID NO 253
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 253

Cys Gly Asn Leu Leu Thr Arg Arg Cys
1               5

<210> SEQ ID NO 254
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 254

Cys Ile Asn Cys Leu Ser Gln Cys
1               5

<210> SEQ ID NO 255
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 255

Cys Leu Arg His Asp Phe Tyr Val Cys
1               5

<210> SEQ ID NO 256
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 256

Cys Asn Ser Arg Ser Glu Asn Cys
1               5

<210> SEQ ID NO 257
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 257

Cys Arg Tyr Lys Gly Pro Ser Cys

```
                    1               5

<210> SEQ ID NO 258
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 258

Cys Ser His His Asp Thr Asn Cys
  1               5

<210> SEQ ID NO 259
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 259

Cys Ser Arg Trp Tyr Thr Thr Cys
  1               5

<210> SEQ ID NO 260
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 260

Cys Tyr Ala Gly Ser Pro Leu Cys
  1               5

<210> SEQ ID NO 261
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 261

Cys Gln Thr Thr Ser Trp Asn Cys
  1               5

<210> SEQ ID NO 262
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 262

Cys Gln Trp Ser Met Asn Val Cys
  1               5

<210> SEQ ID NO 263
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 263

Cys Arg Ala Arg Ile Arg Ala Glu Asp Ile Ser Cys
  1               5                  10
```

```
<210> SEQ ID NO 264
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 264

Cys Arg Arg Glu Tyr Ser Ala Cys
  1               5

<210> SEQ ID NO 265
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 265

Glu Val Gln Ser Ala Lys Trp
  1               5

<210> SEQ ID NO 266
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 266

Lys Arg Val Tyr Val Leu Gly
  1               5

<210> SEQ ID NO 267
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 267

Gly Arg Leu Ser Val Gln Val
  1               5

<210> SEQ ID NO 268
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 268

Trp Lys Pro Ala Ser Leu Ser
  1               5

<210> SEQ ID NO 269
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 269

Phe Ala Val Arg Val Val Gly
  1               5
```

```
<210> SEQ ID NO 270
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 270

Leu Val Arg Pro Leu Glu Gly
 1               5

<210> SEQ ID NO 271
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 271

Gly Phe Tyr Arg Met Leu Gly
 1               5

<210> SEQ ID NO 272
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 272

Glu Gly Arg Pro Met Val Tyr
 1               5

<210> SEQ ID NO 273
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 273

Gly Ser Arg Ser Leu Gly Ala
 1               5

<210> SEQ ID NO 274
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 274

Arg Val Trp Gln Gly Asp Val
 1               5

<210> SEQ ID NO 275
<211> LENGTH: 6
<212> TYPE: PRT
<213> ORGANISM: Artificial Sequence
<220> FEATURE:
<223> OTHER INFORMATION: Description of Artificial Sequence: Synthetic

<400> SEQUENCE: 275

Gly Asp Glu Leu Leu Ala
 1               5
```

```
<210> SEQ ID NO 276
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 276

Phe Val Trp Leu Val Gly Ser
 1               5

<210> SEQ ID NO 277
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 277

Gly Ser Glu Pro Met Phe Arg
 1               5

<210> SEQ ID NO 278
<211> LENGTH: 5
<212> TYPE: PRT
<213> ORGANISM: Artificial Sequence
<220> FEATURE:
<223> OTHER INFORMATION: Description of Artificial Sequence: Synthetic

<400> SEQUENCE: 278

Trp His Gln Pro Leu
 1               5

<210> SEQ ID NO 279
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 279

Arg Gly Arg Trp Leu Ala Leu
 1               5

<210> SEQ ID NO 280
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 280

Gln Val Glu Glu Phe Pro Cys
 1               5

<210> SEQ ID NO 281
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 281

Leu Trp Leu Ser Gly Asn Trp
 1               5

<210> SEQ ID NO 282
```

<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 282

Gly Pro Met Leu Ser Val Met
 1               5

<210> SEQ ID NO 283
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 283

Trp Thr Phe Leu Glu Arg Leu
 1               5

<210> SEQ ID NO 284
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 284

Val Leu Pro Gly Gly Gln Trp
 1               5

<210> SEQ ID NO 285
<211> LENGTH: 6
<212> TYPE: PRT
<213> ORGANISM: Artificial Sequence
<220> FEATURE:
<223> OTHER INFORMATION: Description of Artificial Sequence: Synthetic

<400> SEQUENCE: 285

Arg Glu Val Lys Glu Ser
 1               5

<210> SEQ ID NO 286
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 286

Arg Thr Pro Ala Ala Val Met
 1               5

<210> SEQ ID NO 287
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 287

Gly Glu Trp Leu Gly Glu Cys
 1               5

<210> SEQ ID NO 288
<211> LENGTH: 7

```
<212> TYPE: PRT
<213> ORGANISM: Artificial Sequence
<220> FEATURE:
<223> OTHER INFORMATION: Description of Artificial Sequence: Synthetic

<400> SEQUENCE: 288

Pro Asn Pro Leu Met Pro Leu
 1               5

<210> SEQ ID NO 289
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 289

Ser Leu Trp Tyr Leu Gly Ala
 1               5

<210> SEQ ID NO 290
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 290

Tyr Val Gly Gly Trp Glu Leu
 1               5

<210> SEQ ID NO 291
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 291

Ala Val Lys Asp Tyr Phe Arg
 1               5

<210> SEQ ID NO 292
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 292

Gly Val Arg Thr Ser Ile Trp
 1               5

<210> SEQ ID NO 293
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 293

Arg Pro Val Gly Met Arg Lys
 1               5

<210> SEQ ID NO 294
<211> LENGTH: 7
<212> TYPE: PRT
```

```
<213> ORGANISM: Artificial Sequence
<220> FEATURE:
<223> OTHER INFORMATION: Description of Artificial Sequence: Synthetic

<400> SEQUENCE: 294

Arg Val Arg Leu Val Asn Leu
 1               5

<210> SEQ ID NO 295
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 295

Phe Phe Ala Ala Val Arg Ser
 1               5

<210> SEQ ID NO 296
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 296

Lys Leu Val Asn Ser Ser Trp
 1               5

<210> SEQ ID NO 297
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 297

Leu Cys Glu Arg Val Trp Arg
 1               5

<210> SEQ ID NO 298
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 298

Phe Gly Ser Gln Ala Phe Val
 1               5

<210> SEQ ID NO 299
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 299

Trp Leu Glu Arg Pro Glu Tyr
 1               5

<210> SEQ ID NO 300
<211> LENGTH: 7
<212> TYPE: PRT
<213> ORGANISM: Artificial Sequence
```

```
<220> FEATURE:
<223> OTHER INFORMATION: Description of Artificial Sequence: Synthetic

<400> SEQUENCE: 300

Gly Gly Asp Val Met Trp Arg
 1               5

<210> SEQ ID NO 301
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 301

Val Arg Ala Arg Leu Met Ser
 1               5

<210> SEQ ID NO 302
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 302

Thr Leu Arg Glu Ser Gly Pro
 1               5

<210> SEQ ID NO 303
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 303

Trp Gly Cys Lys Leu Arg Phe Cys Ser
 1               5

<210> SEQ ID NO 304
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 304

Met Glu Cys Ile Lys Tyr Ser Cys Leu
 1               5

<210> SEQ ID NO 305
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 305

Gly Ile Cys Ala Thr Val Lys Cys Ser
 1               5

<210> SEQ ID NO 306
<211> LENGTH: 9
<212> TYPE: PRT
<213> ORGANISM: Artificial Sequence
<220> FEATURE:
```

```
<223> OTHER INFORMATION: Description of Artificial Sequence: Synthetic

<400> SEQUENCE: 306

Pro Arg Cys Gln Leu Trp Ala Cys Thr
 1               5

<210> SEQ ID NO 307
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 307

Thr Thr Cys Met Ser Gln Leu Cys Leu
 1               5

<210> SEQ ID NO 308
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 308

Ser His Cys Pro Met Ala Ser Leu Cys
 1               5

<210> SEQ ID NO 309
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 309

Gly Cys Val Arg Arg Leu Leu Cys Asn
 1               5

<210> SEQ ID NO 310
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 310

Thr Ser Cys Arg Leu Phe Ser Cys Ala
 1               5

<210> SEQ ID NO 311
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 311

Lys Tyr Cys Thr Pro Val Glu Cys Leu
 1               5

<210> SEQ ID NO 312
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
<400> SEQUENCE: 312

Arg Gly Cys Asn Gly Ser Arg Cys Ser
 1               5

<210> SEQ ID NO 313
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 313

Met Cys Pro Gln Arg Asn Cys Leu
 1               5

<210> SEQ ID NO 314
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 314

Pro Glu Cys Glu Gly Val Ser Cys Ile
 1               5

<210> SEQ ID NO 315
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 315

Ala Gly Cys Ser Val Thr Val Cys Gly
 1               5

<210> SEQ ID NO 316
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 316

Ile Pro Cys Tyr Trp Glu Ser Cys Arg
 1               5

<210> SEQ ID NO 317
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 317

Gly Ser Cys Ser Met Phe Pro Cys Ser
 1               5

<210> SEQ ID NO 318
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
<400> SEQUENCE: 318

Gln Asp Cys Val Lys Arg Pro Cys Val
 1               5

<210> SEQ ID NO 319
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 319

Ser Glu Cys Ala Tyr Arg Ala Cys Ser
 1               5

<210> SEQ ID NO 320
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 320

Trp Ser Cys Ala Arg Pro Leu Cys Gly
 1               5

<210> SEQ ID NO 321
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 321

Ser Leu Cys Gly Ser Asp Gly Cys Arg
 1               5

<210> SEQ ID NO 322
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 322

Arg Leu Cys Pro Ser Ser Pro Cys Thr
 1               5

<210> SEQ ID NO 323
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 323

Met Arg Cys Gly Phe Ser Gly Cys Thr
 1               5

<210> SEQ ID NO 324
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 324
```

Arg Tyr Cys Tyr Pro Asp Gly Cys Leu
1               5

<210> SEQ ID NO 325
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 325

Ser Thr Cys Gly Asn Trp Thr Cys Arg
1               5

<210> SEQ ID NO 326
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 326

Leu Pro Cys Thr Gly Ala Ser Cys Pro
1               5

<210> SEQ ID NO 327
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 327

Cys Ser Cys Thr Gly Gln Leu Cys Arg
1               5

<210> SEQ ID NO 328
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 328

Leu Glu Cys Arg Arg Trp Arg Cys Asp
1               5

<210> SEQ ID NO 329
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 329

Gly Leu Cys Gln Ile Asp Glu Cys Arg
1               5

<210> SEQ ID NO 330
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 330

-continued

```
Thr Ala Cys Lys Val Ala Ala Cys His
1               5

<210> SEQ ID NO 331
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 331

Asp Arg Cys Leu Asp Ile Trp Cys Leu
1               5

<210> SEQ ID NO 332
<211> LENGTH: 9
<212> TYPE: PRT
<213> ORGANISM: Artificial Sequence
<220> FEATURE:
<221> NAME/KEY: UNSURE
<222> LOCATION: (1)..(3)
<223> OTHER INFORMATION: Unsure
<220> FEATURE:
<223> OTHER INFORMATION: Description of Artificial Sequence: Synthetic

<400> SEQUENCE: 332

Xaa Xaa Xaa Gln Gly Ser Pro Cys Leu
1               5

<210> SEQ ID NO 333
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 333

Pro Leu Cys Met Ala Thr Arg Cys Ala
1               5

<210> SEQ ID NO 334
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 334

Arg Asp Cys Ser His Arg Ser Cys Glu
1               5

<210> SEQ ID NO 335
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 335

Asn Pro Cys Leu Arg Ala Ala Cys Ile
1               5

<210> SEQ ID NO 336
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
<400> SEQUENCE: 336

Pro Thr Cys Ala Tyr Gly Trp Cys Ala
  1               5

<210> SEQ ID NO 337
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 337

Leu Glu Cys Val Ala Asn Leu Cys Thr
  1               5

<210> SEQ ID NO 338
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 338

Arg Lys Cys Gly Glu Glu Val Cys Thr
  1               5

<210> SEQ ID NO 339
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 339

Glu Pro Cys Thr Trp Asn Ala Cys Leu
  1               5

<210> SEQ ID NO 340
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 340

Leu Val Cys Pro Gly Thr Ala Cys Val
  1               5

<210> SEQ ID NO 341
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 341

Leu Tyr Cys Leu Asp Ala Ser Cys Leu
  1               5

<210> SEQ ID NO 342
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
<400> SEQUENCE: 342

Glu Arg Cys Pro Met Ala Lys Cys Tyr
 1               5

<210> SEQ ID NO 343
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 343

Leu Val Cys Gln Gly Ser Pro Cys Leu
 1               5

<210> SEQ ID NO 344
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 344

Gln Gln Cys Gln Asp Pro Tyr Cys Leu
 1               5

<210> SEQ ID NO 345
<211> LENGTH: 9
<212> TYPE: PRT
<213> ORGANISM: Artificial Sequence
<220> FEATURE:
<221> NAME/KEY: UNSURE
<222> LOCATION: (2)
<223> OTHER INFORMATION: Unsure
<220> FEATURE:
<221> NAME/KEY: UNSURE
<222> LOCATION: (4)
<223> OTHER INFORMATION: Unsure
<220> FEATURE:
<223> OTHER INFORMATION: Description of Artificial Sequence: Synthetic

<400> SEQUENCE: 345

Asp Xaa Cys Xaa Asp Ile Trp Cys Leu
 1               5

<210> SEQ ID NO 346
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 346

Gln Pro Cys Arg Ser Met Val Cys Ala
 1               5

<210> SEQ ID NO 347
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 347

Lys Thr Cys Val Gly Val Arg Val
 1               5
```

<210> SEQ ID NO 348
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 348

Trp Ser Cys His Glu Phe Met Cys Arg
 1               5

<210> SEQ ID NO 349
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 349

Cys Ser Lys Leu Met Met Thr Cys
 1               5

<210> SEQ ID NO 350
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 350

Leu Thr Cys Trp Asp Trp Ser Cys Arg
 1               5

<210> SEQ ID NO 351
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 351

Ser Leu Cys Arg Leu Ser Thr Cys Ser
 1               5

<210> SEQ ID NO 352
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 352

Lys Thr Cys Ala Gly Ser Ser Cys Ile
 1               5

<210> SEQ ID NO 353
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 353

Val Ile Cys Thr Gly Arg Gln Cys Gly
 1               5

<210> SEQ ID NO 354

```
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 354

Asn Pro Cys Phe Gly Leu Leu Val
 1               5

<210> SEQ ID NO 355
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 355

Ser Leu Cys Thr Ala Phe Asn Cys His
 1               5

<210> SEQ ID NO 356
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 356

Arg Thr Cys Thr Pro Ser Arg Cys Met
 1               5

<210> SEQ ID NO 357
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 357

Gln Ser Cys Leu Trp Arg Ile Cys Ile
 1               5

<210> SEQ ID NO 358
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 358

Gln Tyr Cys Trp Ser Lys Gly Cys Arg
 1               5

<210> SEQ ID NO 359
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 359

Leu Gly Cys Phe Pro Ser Trp Cys Gly
 1               5

<210> SEQ ID NO 360
<211> LENGTH: 9
```

```
<212> TYPE: PRT
<213> ORGANISM: Artificial Sequence
<220> FEATURE:
<223> OTHER INFORMATION: Description of Artificial Sequence: Synthetic

<400> SEQUENCE: 360

Val Thr Cys Ser Ser Glu Trp Cys Leu
 1               5

<210> SEQ ID NO 361
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 361

Arg Leu Cys Ser Trp Gly Gly Cys Ala
 1               5

<210> SEQ ID NO 362
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 362

Ser Thr Cys Ile Ser Val His Cys Ser
 1               5

<210> SEQ ID NO 363
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 363

Glu Val Cys Leu Val Leu Ser Cys Gln
 1               5

<210> SEQ ID NO 364
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 364

Ile Ala Cys Asp Gly Tyr Leu Cys Gly
 1               5

<210> SEQ ID NO 365
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 365

Arg Asp Cys Val Lys Asn Leu Cys Arg
 1               5

<210> SEQ ID NO 366
<211> LENGTH: 9
<212> TYPE: PRT
```

```
<213> ORGANISM: Artificial Sequence
<220> FEATURE:
<221> NAME/KEY: UNSURE
<222> LOCATION: (1)
<223> OTHER INFORMATION: Unsure
<220> FEATURE:
<223> OTHER INFORMATION: Description of Artificial Sequence: Synthetic

<400> SEQUENCE: 366

Xaa Gly Cys Tyr Gln Lys Arg Cys Thr
 1               5

<210> SEQ ID NO 367
<211> LENGTH: 9
<212> TYPE: PRT
<213> ORGANISM: Artificial Sequence
<220> FEATURE:
<221> NAME/KEY: UNSURE
<222> LOCATION: (5)
<223> OTHER INFORMATION: Unsure
<220> FEATURE:
<223> OTHER INFORMATION: Description of Artificial Sequence: Synthetic

<400> SEQUENCE: 367

Leu Gly Cys Phe Xaa Ser Trp Cys Gly
 1               5

<210> SEQ ID NO 368
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 368

Ile Arg Cys Trp Gly Gly Arg Cys Ser
 1               5

<210> SEQ ID NO 369
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 369

Ile Pro Cys Ser Leu Leu Gly Cys Ala
 1               5

<210> SEQ ID NO 370
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 370

Ala Gly Cys Val Gln Ser Gln Cys Tyr
 1               5

<210> SEQ ID NO 371
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 371
```

-continued

```
Pro Arg Cys Trp Glu Arg Val Cys Ser
  1               5

<210> SEQ ID NO 372
<211> LENGTH: 9
<212> TYPE: PRT
<213> ORGANISM: Artificial Sequence
<220> FEATURE:
<221> NAME/KEY: UNSURE
<222> LOCATION: (9)
<220> FEATURE:
<223> OTHER INFORMATION: Description of Artificial Sequence: Synthetic

<400> SEQUENCE: 372

Lys Ala Cys Phe Gly Ala Asp Cys Xaa
  1               5

<210> SEQ ID NO 373
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 373

Thr Leu Cys Pro Leu Val Ala Cys Glu
  1               5

<210> SEQ ID NO 374
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 374

Ser Ala Cys Trp Leu Ser Asn Cys Ala
  1               5

<210> SEQ ID NO 375
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 375

Ser Glu Cys Tyr Thr Gly Ser Cys Pro
  1               5

<210> SEQ ID NO 376
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 376

Gly Leu Cys Gln Glu His Arg Cys Trp
  1               5

<210> SEQ ID NO 377
<211> LENGTH: 9
<212> TYPE: PRT
<213> ORGANISM: Artificial Sequence
<220> FEATURE:
<223> OTHER INFORMATION: Description of Artificial Sequence: Synthetic
```

<400> SEQUENCE: 377

Val Glu Cys Gly Phe Ser Ala Val Phe
 1               5

<210> SEQ ID NO 378
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 378

Glu Asp Cys Arg Glu Trp Gly Cys Arg
 1               5

<210> SEQ ID NO 379
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 379

His Trp Cys Arg Leu Leu Ala Cys Arg
 1               5

<210> SEQ ID NO 380
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 380

His Lys Gly Gln Val Tyr Ser
 1               5

<210> SEQ ID NO 381
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 381

Phe Ser Asp Val His Phe Trp
 1               5

<210> SEQ ID NO 382
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 382

Arg Gly Ile Phe Val Ser Ser
 1               5

<210> SEQ ID NO 383
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 383

```
Pro Lys Val Lys Leu Ser Glu
 1               5
```

<210> SEQ ID NO 384
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 384

```
Leu Arg Phe Trp Gln Glu Ser
 1               5
```

<210> SEQ ID NO 385
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 385

```
Ile Trp Thr Val Val Gly Gln
 1               5
```

<210> SEQ ID NO 386
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 386

```
Asp Lys Val Gly Leu Ser Val
 1               5
```

<210> SEQ ID NO 387
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 387

```
Ser Glu Thr Trp Arg Gln Phe
 1               5
```

<210> SEQ ID NO 388
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 388

```
Leu Asp Gly Met Ile Val Lys
 1               5
```

<210> SEQ ID NO 389
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 389

Arg Tyr Pro Leu Ala Gly Gly
1               5

<210> SEQ ID NO 390
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 390

Phe Thr Asp Gly Glu Asp Lys
1               5

<210> SEQ ID NO 391
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 391

Arg Ser Thr Glu His Met Ser
1               5

<210> SEQ ID NO 392
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 392

Ser Gly Arg Arg His Glu Leu
1               5

<210> SEQ ID NO 393
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 393

Ser Ser Ser Arg Val Arg Ser
1               5

<210> SEQ ID NO 394
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 394

Tyr His Arg Ser Val Gly Arg
1               5

<210> SEQ ID NO 395
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 395

Pro Leu Leu Arg Pro Pro His

<210> SEQ ID NO 396
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 396

Ser Asp Lys Leu Gly Phe Val
 1               5

<210> SEQ ID NO 397
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 397

Ala Gly Ser Arg Thr Asn Arg
 1               5

<210> SEQ ID NO 398
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 398

Ile Thr Gln Leu His Lys Thr
 1               5

<210> SEQ ID NO 399
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 399

Ala Arg Cys Leu Val Tyr Arg
 1               5

<210> SEQ ID NO 400
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 400

Gly Tyr Val Ala Val Met Thr
 1               5

<210> SEQ ID NO 401
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 401

Gly Leu Gln Val Lys Trp Val
 1               5

<210> SEQ ID NO 402
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 402

Ile Phe Thr Pro Gly Trp Leu
 1               5

<210> SEQ ID NO 403
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 403

Lys Gln Thr Ser Arg Phe Leu
 1               5

<210> SEQ ID NO 404
<211> LENGTH: 7
<212> TYPE: PRT
<213> ORGANISM: Artificial Sequence
<220> FEATURE:
<221> NAME/KEY: SITE
<222> LOCATION: (2)
<223> OTHER INFORMATION: Tyrosine or Phenylalanine
<220> FEATURE:
<223> OTHER INFORMATION: Description of Artificial Sequence: Synthetic

<400> SEQUENCE: 404

Arg Xaa Leu Leu Ala Gly Gly
 1               5

<210> SEQ ID NO 405
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 405

Ala Arg Arg Gly Trp Thr Leu
 1               5

<210> SEQ ID NO 406
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 406

Ser Arg Arg Phe Val Gly Gly
 1               5

<210> SEQ ID NO 407
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 407

Gln Leu Thr Gly Gly Cys Leu
1               5

<210> SEQ ID NO 408
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 408

Ala Leu Glu Arg Arg Ser Leu
1               5

<210> SEQ ID NO 409
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 409

Lys Ala Tyr Phe Arg Trp Arg
1               5

<210> SEQ ID NO 410
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 410

Arg Trp Leu Ala Trp Thr Val
1               5

<210> SEQ ID NO 411
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 411

Val Gly Ser Phe Ile Tyr Ser
1               5

<210> SEQ ID NO 412
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 412

Leu Ser Leu Leu Gly Ile Ala
1               5

<210> SEQ ID NO 413
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 413

-continued

```
Leu Ser Thr Val Leu Trp Phe
  1               5

<210> SEQ ID NO 414
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 414

Ser Leu Ala Met Arg Asp Ser
  1               5

<210> SEQ ID NO 415
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 415

Gly Arg Ser Ser Leu Ala Cys
  1               5

<210> SEQ ID NO 416
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 416

Ser Glu Leu Leu Gly Asp Ala
  1               5

<210> SEQ ID NO 417
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 417

Cys Gly Gly Ala Gly Ala Arg
  1               5

<210> SEQ ID NO 418
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 418

Trp Arg Gln Asn Met Pro Leu
  1               5

<210> SEQ ID NO 419
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 419

Asp Phe Leu Arg Cys Arg Val
```

1               5

<210> SEQ ID NO 420
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 420

Gln Ala Gly Leu Arg Cys His
    1               5

<210> SEQ ID NO 421
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 421

Arg Ala Leu Tyr Asp Ala Leu
    1               5

<210> SEQ ID NO 422
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 422

Trp Val Ser Val Leu Gly Phe
    1               5

<210> SEQ ID NO 423
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 423

Gly Met Ala Val Ser Ser Trp
    1               5

<210> SEQ ID NO 424
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 424

Ser Trp Phe Phe Leu Val Ala
    1               5

<210> SEQ ID NO 425
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 425

Trp Gln Ser Val Val Arg Val
    1               5

```
<210> SEQ ID NO 426
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 426

Cys Gly Asn Gly His Ser Cys
 1               5

<210> SEQ ID NO 427
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 427

Ala Glu Met Glu Gly Arg Asp
 1               5

<210> SEQ ID NO 428
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 428

Ser Leu Arg Pro Asp Asn Gly
 1               5

<210> SEQ ID NO 429
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 429

Pro Ala Met Gly Leu Ile Arg
 1               5

<210> SEQ ID NO 430
<211> LENGTH: 4
<212> TYPE: PRT
<213> ORGANISM: Artificial Sequence
<220> FEATURE:
<223> OTHER INFORMATION: Description of Artificial Sequence: Synthetic

<400> SEQUENCE: 430

Leu Ala Gly Gly
 1

<210> SEQ ID NO 431
<211> LENGTH: 23
<212> TYPE: PRT
<213> ORGANISM: Artificial Sequence
<220> FEATURE:
<221> NAME/KEY: SITE
<222> LOCATION: (1)
<223> OTHER INFORMATION: 1 to 10 independently selected amino acids
<220> FEATURE:
<221> NAME/KEY: SITE
<222> LOCATION: (14)..(23)
<223> OTHER INFORMATION: 1 to 10 independently selected amino acids
```

```
<220> FEATURE:
<223> OTHER INFORMATION: Description of Artificial Sequence: Synthetic

<400> SEQUENCE: 431

Xaa Xaa Xaa Xaa Xaa Xaa Xaa Xaa Xaa Xaa Leu Pro Arg Xaa Xaa Xaa
 1               5                   10                  15

Xaa Xaa Xaa Xaa Xaa Xaa Xaa
            20

<210> SEQ ID NO 432
<211> LENGTH: 24
<212> TYPE: PRT
<213> ORGANISM: Artificial Sequence
<220> FEATURE:
<221> NAME/KEY: SITE
<222> LOCATION: (1)..(10)
<223> OTHER INFORMATION: 1 to 10 independently selected amino acids
<220> FEATURE:
<221> NAME/KEY: SITE
<222> LOCATION: (15)..(25)
<223> OTHER INFORMATION: 0 to 10 independently selected amino acids
<220> FEATURE:
<223> OTHER INFORMATION: Description of Artificial Sequence: Synthetic

<400> SEQUENCE: 432

Xaa Xaa Xaa Xaa Xaa Xaa Xaa Xaa Xaa Xaa Leu Ala Gly Gly Xaa Xaa
 1               5                   10                  15

Xaa Xaa Xaa Xaa Xaa Xaa Xaa Xaa
            20

<210> SEQ ID NO 433
<211> LENGTH: 15
<212> TYPE: PRT
<213> ORGANISM: Artificial Sequence
<220> FEATURE:
<221> NAME/KEY: SITE
<222> LOCATION: (6)..(15)
<223> OTHER INFORMATION: 1 to 10 independently selected amino acids
<220> FEATURE:
<223> OTHER INFORMATION: Description of Artificial Sequence: Synthetic

<400> SEQUENCE: 433

Tyr Ser Gly Lys Trp Xaa Xaa Xaa Xaa Xaa Xaa Xaa Xaa Xaa Xaa
 1               5                   10                  15

<210> SEQ ID NO 434
<211> LENGTH: 23
<212> TYPE: PRT
<213> ORGANISM: Artificial Sequence
<220> FEATURE:
<221> NAME/KEY: SITE
<222> LOCATION: (1)..(10)
<223> OTHER INFORMATION: 1 to 10 independently selected amino acids
<220> FEATURE:
<221> NAME/KEY: SITE
<222> LOCATION: (14)..(23)
<223> OTHER INFORMATION: 1 to 10 independently selected amino acids
<220> FEATURE:
<223> OTHER INFORMATION: Description of Artificial Sequence: Synthetic

<400> SEQUENCE: 434

Xaa Xaa Xaa Xaa Xaa Xaa Xaa Xaa Xaa Xaa Arg Gly Ser Xaa Xaa Xaa
 1               5                   10                  15

Xaa Xaa Xaa Xaa Xaa Xaa Xaa
            20

<210> SEQ ID NO 435
<211> LENGTH: 12
```

```
<212> TYPE: PRT
<213> ORGANISM: Artificial Sequence
<220> FEATURE:
<223> OTHER INFORMATION: Description of Artificial Sequence: Synthetic

<400> SEQUENCE: 435

Cys Cys Phe Thr Asn Phe Asp Cys Tyr Leu Gly Cys
 1               5                  10

<210> SEQ ID NO 436
<211> LENGTH: 23
<212> TYPE: PRT
<213> ORGANISM: Artificial Sequence
<220> FEATURE:
<221> NAME/KEY: UNSURE
<222> LOCATION: (1)..(10)
<223> OTHER INFORMATION: 1 to 10 independently selected amino acids
<220> FEATURE:
<221> NAME/KEY: UNSURE
<222> LOCATION: (14)..(23)
<223> OTHER INFORMATION: 1 to 10 independently selected amino acids
<220> FEATURE:
<223> OTHER INFORMATION: Description of Artificial Sequence: Synthetic

<400> SEQUENCE: 436

Xaa Xaa Xaa Xaa Xaa Xaa Xaa Xaa Xaa Xaa Arg Asp Val Xaa Xaa Xaa
 1               5                  10                  15

Xaa Xaa Xaa Xaa Xaa Xaa Xaa
            20

<210> SEQ ID NO 437
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 437

Cys Val Asp Val Cys Cys Asp Gly Cys Pro Val Cys Cys
 1               5                  10

<210> SEQ ID NO 438
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 438

Arg Val Pro Leu Ser Gly Asp Val Glu His
 1               5                  10

<210> SEQ ID NO 439
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 439

Leu Arg Val Met Ser Phe Thr Ser Gly Gln
 1               5                  10

<210> SEQ ID NO 440
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 440

Arg Phe Ser Val Gly Ser Leu Phe Gly Ser
  1               5                  10

<210> SEQ ID NO 441
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 441

Cys Gly Ala Thr Cys Glu Met Gln Cys Pro Ser Gly Cys
  1               5                  10

<210> SEQ ID NO 442
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 442

Gly Arg Gly Glu Ser Pro
  1               5

<210> SEQ ID NO 443
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 443

Cys Ala Arg Ala Cys
  1               5

<210> SEQ ID NO 444
<211> LENGTH: 10
<212> TYPE: PRT
<213> ORGANISM: Rattus sp.

<400> SEQUENCE: 444

Tyr Pro Asp Leu Ile Ala Glu Leu Leu Arg
  1               5                  10

<210> SEQ ID NO 445
<211> LENGTH: 24
<212> TYPE: PRT
<213> ORGANISM: Rattus sp.

<400> SEQUENCE: 445

Thr Thr Pro Val Ile Asp Gly His Asn Asp Leu Pro Trp Gln Met Leu
  1               5                  10                  15

Thr Leu Phe Asn Asn Gln Leu Arg
             20
```

```
<210> SEQ ID NO 446
<211> LENGTH: 31
<212> TYPE: DNA
<213> ORGANISM: Artificial Sequence
<220> FEATURE:
<223> OTHER INFORMATION: Description of Artificial Sequence: Synthetic
      Nucleotide

<400> SEQUENCE: 446
ccgctggtac cgcagatccc tggggacctt g                              31

<210> SEQ ID NO 447
<211> LENGTH: 31
<212> TYPE: DNA
<213> ORGANISM: Artificial Sequence
<220> FEATURE:
<223> OTHER INFORMATION: Description of Artificial Sequence: Synthetic
      Nucleotide

<400> SEQUENCE: 447
tctttctaga gctcagagag cactggagga g                              31

<210> SEQ ID NO 448
<211> LENGTH: 411
<212> TYPE: PRT
<213> ORGANISM: Homo sapiens

<400> SEQUENCE: 448

Met Trp Ser Gly Trp Trp Leu Trp Ser Leu Val Ala Val Cys Thr Ala
 1               5                  10                  15

Asp Phe Phe Arg Asp Glu Ala Glu Arg Ile Met Arg Asp Ser Pro Val
                20                  25                  30

Ile Asp Gly His Asn Asp Leu Pro Trp Gln Leu Leu Asp Met Phe Asn
            35                  40                  45

Asn Arg Leu Gln Asp Glu Arg Ala Asn Leu Thr Thr Leu Ala Gly Thr
        50                  55                  60

His Thr Asn Ile Pro Lys Leu Arg Ala Gly Phe Val Gly Gly Gln Phe
 65                  70                  75                  80

Trp Ser Val Tyr Thr Pro Cys Asp Thr Gln Asn Lys Asp Ala Val Arg
                85                  90                  95

Arg Thr Leu Glu Gln Met Asp Val Val His Arg Met Cys Arg Met Tyr
               100                 105                 110

Pro Glu Thr Phe Leu Tyr Val Thr Ser Ser Ala Gly Ile Arg Gln Ala
            115                 120                 125

Phe Arg Glu Gly Lys Val Ala Ser Leu Ile Gly Val Glu Gly Gly His
        130                 135                 140

Ser Ile Asp Ser Ser Leu Gly Val Leu Arg Ala Leu Tyr Gln Leu Gly
145                 150                 155                 160

Met Arg Tyr Leu Thr Leu Thr His Ser Cys Asn Thr Pro Trp Ala Asp
                165                 170                 175

Asn Trp Leu Val Asp Thr Gly Asp Ser Glu Pro Gln Ser Gln Gly Leu
            180                 185                 190

Ser Pro Phe Gly Gln Arg Val Val Lys Glu Leu Asn Arg Leu Gly Val
        195                 200                 205

Leu Ile Asp Leu Ala His Val Ser Val Ala Thr Met Lys Ala Thr Leu
    210                 215                 220

Gln Leu Ser Arg Ala Pro Val Ile Phe Ser His Ser Ser Ala Tyr Ser
225                 230                 235                 240

Val Cys Ala Ser Arg Arg Asn Val Pro Asp Asp Val Leu Arg Leu Val
```

-continued

```
                245                 250                 255
Lys Gln Thr Asp Ser Leu Val Met Val Asn Phe Tyr Asn Asn Tyr Ile
            260                 265                 270
Ser Cys Thr Asn Lys Ala Asn Leu Ser Gln Val Ala Asp His Leu Asp
        275                 280                 285
His Ile Lys Glu Val Ala Gly Ala Arg Ala Val Gly Phe Gly Gly Asp
    290                 295                 300
Phe Asp Gly Val Pro Arg Val Pro Glu Gly Leu Glu Asp Val Ser Lys
305                 310                 315                 320
Tyr Pro Asp Leu Ile Ala Glu Leu Leu Arg Arg Asn Trp Thr Glu Ala
                325                 330                 335
Glu Val Lys Gly Ala Leu Ala Asp Asn Leu Leu Arg Val Phe Glu Ala
            340                 345                 350
Val Glu Gln Ala Ser Asn Leu Thr Gln Ala Pro Glu Glu Glu Pro Ile
        355                 360                 365
Pro Leu Asp Gln Leu Gly Gly Ser Cys Arg Thr His Tyr Gly Tyr Ser
    370                 375                 380
Ser Gly Ala Ser Ser Leu His Arg His Trp Gly Leu Leu Ala Ser
385                 390                 395                 400
Leu Ala Pro Leu Val Leu Cys Leu Ser Leu Leu
                405                 410

<210> SEQ ID NO 449
<211> LENGTH: 409
<212> TYPE: PRT
<213> ORGANISM: Sus scrofa

<400> SEQUENCE: 449

Met Trp Thr Ser Trp Trp Leu Trp Pro Leu Val Ala Val Cys Ala Ala
  1               5                  10                  15
Asp Gln Phe Arg Asp Leu Ala Val Arg Ile Met Gln Asp Thr Pro Val
                20                  25                  30
Ile Asp Gly His Asn Asp Leu Pro Trp Gln Leu Leu Asn Leu Phe Asn
            35                  40                  45
Asn Gln Leu Gln Asp Pro Gly Ala Asn Leu Ser Ser Leu Ala His Thr
        50                  55                  60
His Thr Asn Ile Pro Lys Leu Lys Ala Gly Phe Val Gly Gly Gln Phe
    65                  70                  75                  80
Trp Ser Ala Tyr Val Pro Cys Asp Thr Gln Asn Arg Asp Ala Val Lys
                85                  90                  95
Arg Thr Leu Glu Gln Ile Asp Val Ile Gln Arg Met Cys Gln Ala Tyr
                100                 105                 110
Pro Glu Thr Phe Ala Cys Val Thr Ser Ser Thr Gly Ile Arg Gln Ala
            115                 120                 125
Phe Arg Glu Gly Lys Val Ala Ser Leu Val Gly Val Glu Gly Gly His
        130                 135                 140
Ser Ile Asp Ser Ser Leu Gly Val Leu Arg Ala Leu Tyr His Leu Gly
145                 150                 155                 160
Met Arg Tyr Met Thr Leu Thr His Ser Cys Asn Thr Pro Trp Ala Asp
                165                 170                 175
Asn Trp Leu Val Asp Thr Gly Asp Asp Lys Ala Gln Ser Gln Gly Leu
            180                 185                 190
Ser His Phe Gly Gln Ser Val Val Lys Glu Met Asn Arg Leu Gly Val
        195                 200                 205
```

-continued

```
Met Ile Asp Leu Ala His Val Ser Val Ala Thr Met Arg Ala Ala Leu
    210                 215                 220
Lys Leu Ser Gln Ala Pro Val Ile Phe Ser His Ser Ser Ala Tyr Ser
225                 230                 235                 240
Leu Cys Pro His Arg Arg Asn Val Pro Asp Asp Val Leu Gln Leu Val
                245                 250                 255
Lys Glu Thr Gly Ser Leu Val Met Val Asn Phe Tyr Asn Asp Tyr Val
            260                 265                 270
Ser Cys Ser Ala Lys Ala Asn Leu Ser Gln Val Ala Asp His Leu Asp
        275                 280                 285
His Ile Lys Lys Val Ala Gly Ala Ala Val Gly Phe Gly Gly Asp
    290                 295                 300
Tyr Asp Gly Val Ser Arg Val Pro Ser Gly Leu Glu Asp Val Ser Lys
305                 310                 315                 320
Tyr Pro Asp Leu Val Ala Glu Leu Leu Arg Arg Gln Trp Thr Glu Ala
                325                 330                 335
Glu Val Arg Gly Ala Leu Ala Asp Asn Leu Leu Arg Val Phe Glu Ala
            340                 345                 350
Val Glu Gln Ala Ser Asn His Ala Gln Val Pro Gly Glu Glu Pro Ile
        355                 360                 365
Pro Leu Gly Gln Leu Glu Ala Ser Cys Arg Thr Asn Tyr Gly Tyr Ser
    370                 375                 380
Ala Ala Pro Ser Leu His Leu Pro Pro Gly Ser Leu Leu Ala Ser Leu
385                 390                 395                 400
Val Pro Leu Leu Leu Leu Ser Leu Pro
                405

<210> SEQ ID NO 450
<211> LENGTH: 410
<212> TYPE: PRT
<213> ORGANISM: Rattus sp.

<400> SEQUENCE: 450

Met Leu Ile Ile Trp Trp Phe Trp Ser Leu Leu Ala Ile Cys Ala Ser
  1               5                  10                  15
Asp Ser Phe Arg Asn Gln Ala Glu Asn Ile Met Arg Thr Thr Pro Val
                20                  25                  30
Ile Asp Gly His Asn Asp Leu Pro Trp Gln Met Leu Thr Leu Phe Asn
            35                  40                  45
Asn Gln Leu Arg Lys Ser Glu Ala Asn Leu Ser Ala Leu Ala Glu Thr
        50                  55                  60
His Thr Asn Ile Pro Lys Leu Arg Ala Gly Phe Val Gly Gly Gln Phe
  65                  70                  75                  80
Trp Ser Ala Tyr Met Pro Cys Asp Thr Gln Asn Lys Asp Ala Val Lys
                85                  90                  95
Arg Ile Leu Glu Gln Ile Asp Val Ile His Arg Met Cys Gln Leu Tyr
                100                 105                 110
Pro Glu Thr Phe Glu Cys Val Thr Asn Ser Ser Asp Ile Leu Gln Ala
            115                 120                 125
Phe Arg Arg Gly Lys Val Ala Ser Leu Ile Gly Val Glu Gly Gly His
        130                 135                 140
Leu Ile Asp Ser Ser Leu Gly Val Leu Arg Thr Leu Tyr His Leu Gly
145                 150                 155                 160
Met Arg Tyr Leu Thr Leu Thr His Asn Cys Asn Thr Pro Trp Ala Asp
                165                 170                 175
```

-continued

```
Asn Trp Leu Val Asp Lys Gly Asp Asp Glu Ala Glu Ser Gln Gly Leu
            180                 185                 190
Ser Pro Phe Gly Lys Leu Val Leu Asn Glu Met Asn Arg Leu Gly Val
        195                 200                 205
Met Ile Asp Leu Ser His Val Ser Val Ala Thr Met Lys Asp Ala Leu
    210                 215                 220
Gln Leu Ser Lys Ala Pro Val Ile Phe Ser His Ser Ser Ala Tyr Ser
225                 230                 235                 240
Val Cys Pro His Arg Arg Asn Val Pro Asp Asp Val Leu Gln Leu Val
                245                 250                 255
Lys Ser Thr Asn Ser Leu Val Met Val Asn Phe Tyr Asn Gln Phe Val
            260                 265                 270
Ser Cys Ser Asp Ser Ala Thr Leu Ser Gln Val Ala Asp His Leu Asp
        275                 280                 285
His Ile Lys Lys Val Ala Gly Ala Gly Ala Val Gly Leu Gly Gly Asp
    290                 295                 300
Tyr Asp Gly Val Thr Asn Leu Pro Val Gly Leu Glu Asp Val Ser Lys
305                 310                 315                 320
Tyr Pro Asp Leu Ile Ala Glu Leu Leu Arg Arg Asn Trp Thr Glu Thr
                325                 330                 335
Glu Val Arg Gly Leu Leu Ala Glu Asn Leu Leu Arg Val Phe Ser Ala
            340                 345                 350
Val Glu Leu Val Ser Asn Ile Met Gln Val Pro Glu Glu Thr Ile
        355                 360                 365
Pro Val Glu Lys Leu Asp Gly Ser Cys Arg Thr Phe Tyr Gly His Ser
    370                 375                 380
Arg Ala Pro Ser Ile His Leu Gln Ile Gly Ala Leu Leu Ala Ser Leu
385                 390                 395                 400
Ala Ser Leu Val Phe Ser Leu His Pro Leu
                405                 410

<210> SEQ ID NO 451
<211> LENGTH: 410
<212> TYPE: PRT
<213> ORGANISM: Mus musculus

<400> SEQUENCE: 451

Met Val Ile Ile Trp Trp Phe Trp Ser Leu Leu Ala Ile Cys Ala Ser
  1               5                  10                  15
Asp Ser Phe Arg Asp Gln Ala Val Ala Ile Met Arg Thr Thr Pro Val
            20                  25                  30
Ile Asp Gly His Asn Asp Leu Pro Trp Gln Leu Leu Asn Leu Phe Asn
        35                  40                  45
Asn Gln Leu Leu Arg Pro Asp Ala Asp Leu Asn Lys Leu Ala Gln Thr
    50                  55                  60
His Thr Asn Ile Pro Lys Leu Lys Ala Gly Phe Val Gly Gly Gln Phe
65                  70                  75                  80
Trp Ser Ala Tyr Met Pro Cys Asp Thr Gln Asn Lys Asp Ala Val Lys
                85                  90                  95
Arg Thr Leu Glu Gln Met Asp Val Ile His Arg Met Cys Gln Leu Tyr
            100                 105                 110
Pro Glu Thr Phe Met Cys Val Thr Asn Ser Ser Asp Ile Leu Gln Ala
        115                 120                 125
Phe Arg Arg Gly Lys Val Ala Ser Leu Ile Gly Val Glu Gly Gly His
```

-continued

```
            130                 135                 140
Leu Ile Asp Ser Ser Leu Gly Val Leu Arg Thr Leu Tyr His Leu Gly
145                 150                 155                 160

Met Arg Tyr Leu Thr Leu Thr His Asn Cys Asn Thr Pro Trp Ala Asp
                165                 170                 175

Asn Trp Leu Val Asp Arg Gly Asp Glu Ala Glu Ser His Gly Leu
            180                 185                 190

Ser Pro Phe Gly Lys Arg Leu Leu Asn Glu Met Thr Arg Leu Gly Val
            195                 200                 205

Met Ile Asp Leu Ser His Val Ser Val Ala Thr Met Lys Asp Ala Leu
210                 215                 220

Gln Ile Ser Arg Ala Pro Val Ile Phe Ser His Ser Ser Ala Tyr Ser
225                 230                 235                 240

Leu Cys Pro His Arg Arg Asn Val Pro Asp Asp Val Leu Gln Leu Val
                245                 250                 255

Lys Asn Thr Ser Ser Leu Val Met Val Asn Phe Phe Ser Asn Phe Val
                260                 265                 270

Ser Cys Ser Asp Ser Ala Thr Leu Pro Gln Val Ala Asp His Leu Asp
            275                 280                 285

His Ile Lys Lys Val Ala Gly Ala Gly Ala Val Gly Leu Gly Gly Asp
            290                 295                 300

Tyr Asp Gly Val Thr Met Leu Pro Val Gly Leu Glu Asp Val Ser Lys
305                 310                 315                 320

Tyr Pro Asp Leu Ile Ala Glu Leu Leu Arg Arg Asn Trp Thr Glu Thr
                325                 330                 335

Glu Val Arg Gly Leu Leu Ala Asp Asn Leu Ile Arg Val Phe Ser Glu
                340                 345                 350

Val Glu Leu Val Ser Ser Asn Met Gln Ser Pro Glu Glu Val Pro Ile
            355                 360                 365

Thr Leu Lys Glu Leu Asp Gly Ser Cys Arg Thr Tyr Tyr Gly Tyr Ser
            370                 375                 380

Gln Ala His Ser Ile His Leu Gln Thr Gly Ala Leu Val Ala Ser Leu
385                 390                 395                 400

Ala Ser Leu Leu Phe Arg Leu His Leu Leu
                405                 410

<210> SEQ ID NO 452
<211> LENGTH: 410
<212> TYPE: PRT
<213> ORGANISM: Oryctolagus cuniculus

<400> SEQUENCE: 452

Met Trp Thr Ser Trp Trp Leu Trp Pro Leu Val Ala Val Cys Thr Ala
1               5                   10                  15

Asp Ser Phe Leu Asp Gln Ala Val Gln Ile Leu Arg Val Thr Pro Val
            20                  25                  30

Ile Asp Gly His Asn Asp Leu Pro Trp Gln Leu Leu Asn Lys Phe Asn
        35                  40                  45

Asn Arg Leu Gln Asp Ser Arg Ala Asn Leu Thr Val Leu Ala Asp Thr
    50                  55                  60

His Thr Asn Ile Pro Lys Leu Arg Ala Gly Phe Val Gly Gly Gln Phe
65                  70                  75                  80

Trp Ser Ala Tyr Thr Pro Cys Asp Thr Gln Asn Lys Asp Thr Val Arg
                85                  90                  95
```

-continued

```
Arg Thr Leu Glu Gln Met Asp Val Val His Arg Met Cys Gln Leu Tyr
            100                 105                 110
Pro Glu Thr Phe Leu Cys Val Thr Asp Ser Ala Gly Ile Gln Gln Ala
        115                 120                 125
Phe Arg Glu Gly Lys Val Ala Ser Leu Ile Gly Val Glu Gly Gly His
        130                 135                 140
Ser Ile Asp Ser Ser Leu Gly Val Leu Arg Ala Leu Tyr Arg Leu Gly
145                 150                 155                 160
Met Arg Tyr Leu Thr Leu Thr His Asn Cys Asn Thr Pro Trp Ala Asp
                165                 170                 175
Asn Trp Leu Val Asp Arg Gly Asp Asp Glu Ala Gln Ser Gly Gly Leu
                180                 185                 190
Ser Val Phe Gly Gln Arg Val Val Arg Glu Met Asn Arg Leu Gly Val
            195                 200                 205
Met Ile Asp Leu Ala His Val Ser Val Ala Thr Met Lys Ala Ala Leu
    210                 215                 220
Gln Leu Ser Thr Ala Pro Val Ile Phe Ser His Ser Ser Ala Phe Thr
225                 230                 235                 240
Val Cys Ala His Lys Arg Asn Val Pro Asp Asp Val Leu Gln Leu Val
            245                 250                 255
Lys Glu Thr Gly Ser Leu Val Met Val Asn Phe Tyr Asn Asp Tyr Val
            260                 265                 270
Ser Cys Ala Ser Glu Ala Thr Leu Ser Gln Val Ala Asp His Leu Asp
        275                 280                 285
Tyr Ile Lys Asn Val Ala Gly Ala Ala Ala Val Arg Phe Gly Gly Asp
    290                 295                 300
Phe Asp Gly Val Thr Arg Leu Pro Val Gly Leu Glu Asp Val Ser Lys
305                 310                 315                 320
Tyr Pro Asp Leu Val Ala Glu Leu Leu Arg Arg Gly Trp Thr Glu Ala
                325                 330                 335
Glu Val Arg Gly Ala Leu Ala Glu Asn Leu Leu Arg Val Phe Arg Glu
            340                 345                 350
Val Glu Gln Val Ser Asn Gln Ala Gln Val Pro Glu Glu Glu Pro Ile
            355                 360                 365
Ser Leu Glu Gln Leu Gly Gly Ser Cys Arg Thr Gln Tyr Gly Tyr Ser
    370                 375                 380
Glu Ala Pro Ser Leu His Arg Arg Pro Gly Ala Leu Leu Ala Ser Leu
385                 390                 395                 400
Ser Leu Leu Leu Leu Ser Leu Gly Leu Leu
                405                 410
```

METHODS OF HOMING MOLECULES TO LUNG USING MEMBRANE DIPEPTIDASE

This application is a divisional of application Ser. No. 09/258,754, filed Feb. 26, 1999 now U.S. Pat. No. 6,174,687, which is a cip of Ser. No. 09/042,107 filed Mar. 13, 1998 now U.S. Pat. No. 6,232,287.

This invention was made with government support under grant numbers CA 74238 and CA 30199 awarded by the National Institutes of Health.

BACKGROUND OF THE INVENTION

1. Field of the Invention

The present invention relates generally to the fields of molecular medicine and drug delivery and, more specifically, to molecules that home to a specific organ or tissue.

2. Background Information

Although the effect of a particular pathology often is manifest throughout the body of the afflicted person, generally, the underlying pathology may affect only a single organ or tissue. It is rare, however, that a drug or other treatment will target only the diseased organ or tissue. More commonly, treatment results in undesirable side effects due, for example, to generalized toxic effects throughout the patient's body. It would be desirable to selectively target organs or tissues, for example, for treatment of diseases associated with the target organ or tissue. In particular, targeting of an organ or tissue can be useful for directing the expression of a gene to a certain organ or tissue because incorporation of a foreign gene into nontargeted cells can cause unwanted side effects such as malignant transformation.

Most therapeutic substances are delivered to the target organ or tissue through the circulation. The endothelium, which lines the internal surfaces of blood vessels, is the first cell type encountered by a circulating therapeutic substance in the target organ or tissue. These cells provide a target for selectively directing therapies to an organ or tissue.

Endothelium can have distinct morphologies and biochemical markers in different tissues. The blood vessels of the lymphatic system, for example, express various adhesion proteins that serve to guide lymphocyte homing. For example, endothelial cells present in lymph nodes express a cell surface marker that is a ligand for L-selectin and endothelial cells in Peyer's patch venules express a ligand for the $\alpha_4\beta_7$ integrin. These ligands are involved in specific lymphocyte homing to their respective lymphoid organs. Thus, linking a drug to L-selectin or to the $\alpha_4\beta_7$ integrin may provide a means for targeting the drug to diseased lymph nodes or Peyer's patches, respectively, provided that these molecules do not bind to similar ligands present in a significant number of other organs or tissues.

Although the homing molecules present in the blood vessels of non-lymphoid tissues have not been clearly defined, certain observations of lymphocyte circulation suggest that organ and tissue specific endothelial markers exist. Similarly, the homing or metastasis of particular types of tumor cells to specific organs or tissues further suggests that organ and tissue specific markers may exist. Thus, a need exists to identify molecules that can bind to such organ or tissue specific markers and, therefore, can home to the organ or tissue. The present invention satisfies this need and provides related advantages as well.

SUMMARY OF THE INVENTION

The present invention provides a method of identifying a membrane dipeptidase (MDP)-binding homing molecule, which is a molecule that selectively homes to lung endothelium. The method includes the steps of contacting MDP with one or more molecules; and determining specific binding of a molecule to the MDP, where the presence of specific binding identifies the molecule as a MDP-binding homing molecule that selectively homes to lung endothelium. In a method of the invention, the MDP can be, for example, in its natural state or substantially purified and, if desired, immobilized on a support. The membrane dipeptidase can be any mammalian MDP, for example, human MDP having SEQ ID NO: 448.

Further provided by the invention is a method of selectively directing a moiety to lung endothelium in a subject by administering to the subject a conjugate containing a moiety linked to a MDP-binding homing molecule that selectively homes to lung endothelium, whereby the moiety is selectively directed to lung endothelium in the subject. Such a method can be useful, for example, for drug targeting to lung. In a method of the invention, the MDP-binding homing molecule is identified by contacting membrane dipeptidase (MDP) with one or more molecules; and determining specific binding of a molecule to the MDP, where the presence of specific binding identifies the molecule as a MDP-binding homing molecule that selectively homes to lung endothelium. A variety of moieties can be selectively directed to lung endothelium according to a method of the invention. A moiety useful in the invention can be, for example, a gene therapy vector or drug.

In one embodiment, the invention provides a method for selectively directing a moiety to lung endothelium where the MDP-binding homing molecule is a peptide including the sequence $X_1$-G-F-E-$X_2$ (SEQ ID NO: 17), where $X_1$ and $X_2$ each is 1 to 10 independently selected amino acids. Such a MDP-binding homing peptide can include, for example, the sequence CGFECVRQCPERC (SEQ ID NO: 1) or CGFELETC (SEQ ID NO: 2).

In another embodiment, the invention provides a method for selectively directing a moiety to lung endothelium where the MDP-binding homing molecule contains the following Structure 1:

$$R^2CONH-\underset{\underset{COOR^1}{\overset{\|}{C}}}{\overset{R^3\diagdown\diagup H}{C}}$$

where $R^2$ and $R^3$ are hydrocarbon radicals in the range respectively of 3–10 and 1–15 carbon atoms; in either one of these $R^2$ or $R^3$ hydrocarbon chains 1–6 hydrogens may be replaced by halogens or a nonterminal methylene may be replaced by oxygen or sulfur, including oxidized forms of the latter; additionally, a terminal hydrogen in $R^3$ can also be replaced by hydroxyl or thiol, which may be acylated or carbamoylated; or the hydrogen can be replaced by amino, which may be derivatized as in an acylamino, ureido, amidino, quanidino, or alkyl or substituted amino group, including quaternary nitrogen grouping; or, there may be replacement by acid groups such as carboxylic, phosphonic or sulfonic acid groups or esters or amides thereof, or cyano; or combinations thereof, such as a terminal amino acid grouping; and $R^1$ is hydrogen or lower alkyl ($C_{1-6}$) or dialkylaminoalkyl, or a pharmaceutically acceptable cation. Such an MDP-binding homing molecule for reducing or preventing lung metastasis can be, for example, 7-(L-2-amino-2-carboxyethylthio)-2-(2,2-dimethylcyclopropane-carboxamido)-2-heptenoic acid, also known as cilastatin.

An MDP-binding homing molecule can be, for example, a compound having Structure 1 in which $R^2$ is branched alkyl or cycloalkyl with a limitation that the carbon adjacent to the carbonyl cannot be tertiary.

An MDP-binding homing molecule also can be, for example, a compound having Structure 1 in which $R^2$ is branched alkyl or cycloalkyl with a limitation that the carbon adjacent to the carbonyl cannot be tertiary, and in which $R^3$ is n-alkyl (1–9 carbons) or n-alkyl (1–9 carbons) having a terminal substituent which is a quaternary nitrogen, amine derivative or amino acid derived group. An MDP-binding homing molecule can be, for example, a compound having Structure 1 in which $R^2$ is 2,2-dimethylcyclopropyl or 2,2-dichlorocyclopropyl and in which $R^3$ is a hydrocarbon chain of 3 to 7 carbon atoms without a terminal substituent or having a terminal substituent which is trimethylammonium, amidino, guanidino or 2-amino-2-carboethylthio.

Exemplary MDP-binding homing molecules having Structure 1 useful in the invention include the following: Z-2-(2,2-dimethylcyclopropanecarboxamido)-8-trimethylammonium hydroxide-2-octenoic acid inner salt; Z-2-(2,2-dichlorocyclopropanecarboxamido)-8-trimethylammonium hydroxide-2-octenoic acid inner salt; Z-2-(2,2-dimethylcyclopropanecarboxamido)-8-guanidino-2-octenoic acid; Z-2-(2,2-dimethylcyclopropanecarboxamido)-8-guanidino-2-octenoic acid; Z-2-(2,2-dimethylcyclopropanecarboxamido)-8-ureido-2-octenoic acid; Z-8-(1-2-amino-2-carboxyethylthio)-2-(2,2-dimethylcyclopropanecarboxamido)-2-octenoic acid; Z-2-(2,2-dimethylcyclopropanecarboxamido)-2-octenoic acid (racemic and dextrorotatory forms); Z-2-(2,2-dichlorocyclopropanecarboxamido)-2-octenoic acid; 7-(L-2-amino-2-carboxyethylthio)-2-(2,2-dimethylcyclopropanecarboxamido)-2-heptenoic acid; and 6-(L-2-amino-2-carboxyethylthio)-2-(2,2-dimethylcyclopropanecarboxamido)-2-hexenoic acid.

The present invention also provides a method of reducing or preventing lung metastasis in a subject having cancer by administering to the subject a membrane dipeptidase (MDP)-binding homing molecule. In a preferred embodiment, an MDP-binding homing molecule is a lung homing peptide including the sequence $X_1$-G-F-E-$X_2$ (SEQ ID NO: 17), where $X_1$ and $X_2$ each is 1 to 10 independently selected amino acids, such as a peptide including the sequence CGFECVRQCPERC (SEQ ID NO: 1) or CGFELETC (SEQ ID NO: 2).

In another preferred embodiment, an MDP-binding homing molecule is a molecule containing Structure 1, described hereinabove. Such an MDP-binding homing molecule can be, for example, 7-(L-2-amino-2-carboxyethylthio)-2-(2,2-dimethylcyclopropanecarboxamido)-2-heptenoic acid, commonly known as cilastatin.

In one embodiment, an MDP-binding homing molecule useful in the invention is an MDP inhibitor. Such an MDP inhibitor can exhibit, for example, a Ki against MDP of 1000 nM or less. In other embodiments, an MDP inhibitor useful in reducing or preventing lung metastasis exhibits a Ki against MDP of 100 nM or less or a Ki against MDP of 1 nM or less.

The present invention also provides a method of reducing or preventing lung metastasis in a subject having cancer by administering to the subject a MDP negative regulatory agent. A MDP negative regulatory agent useful in the invention can be, for example, a soluble MDP polypeptide or an antibody that selectively reacts with MDP.

Further provided herein are methods of reducing or preventing cell homing to lung endothelium in a subject by administering to the subject a MDP negative regulatory agent. A MDP negative regulatory agent useful for reducing or preventing cell homing to lung endothelium can be, for example, a soluble MDP polypeptide or an antibody that selectively reacts with MDP.

The present invention also provides a method of identifying a molecule that reduces or prevents lung metastasis by contacting membrane dipeptidase (MDP) with one or more molecules; and determining MDP activity in the presence of the molecule as compared to a control value, where diminished MDP activity in the presence of the molecule identifies the molecule as a molecule that reduces or prevents lung metastasis. The membrane dipeptidase can be, for example, substantially purified. MDP activity can be determined, for example, by release of D-Phe from Gly-D-Phe.

In one embodiment, the invention provides a method of identifying a molecule that reduces or prevents lung metastasis by contacting MDP with one or more molecules; determining MDP activity in the presence of the molecule as compared to a control value; administering the molecule to a subject having cancer; and assaying lung metastasis in the subject as compared to a control level of metastasis, where diminished MDP activity in the presence of the molecule identifies the molecule as a molecule that reduces or prevents lung metastasis.

BRIEF DESCRIPTION OF THE DRAWINGS

FIG. 2B, CGFELETC, SEQ ID NO: 2, "GFE-2"); skin (FIG. 2C, CVALCREACGEGC, SEQ ID NO: 3) or pancreas (FIG. 2D, SWCEPGWCR, SEQ ID NO: 4) were individually amplified, injected into mice and recovered (Example I). The amount of phage displaying a selected peptide that was recovered per gram of lung, skin or pancreas or control kidney or brain was determined. The amount of unselected (control) phage recovered from lung, skin, pancreas, kidney or brain also was determined. Bars indicate standard error of the mean from triplicate platings.

In FIG. 3A, 100 µg or 500 µg of GST-CGFECVRQCPERC (SEQ ID NO: 1, "GFE-1") or 500 µg GST was coinjected into mice with $10^9$ transducing units of the individually amplified phage displaying the lung homing sequence CGFECVRQCPERC (SEQ ID NO: 1). The recovery of phage after 5 minutes of circulation from lung and kidney was determined, with bars indicating standard error of the mean from triplicate platings.

In FIG. 3B, $10^9$ transducing units of individually amplified phage displaying either the lung homing peptides CGFECVRQCPERC (SEQ ID NO: 1, "GFE-1") or CGFELETC (SEQ ID NO: 2, "GFE-2") or the skin homing peptide CVALCREACGEGC (SEQ ID NO: 3) were coinjected into mice with 500 µg of the cognate GST-fusion peptide. Control mice (not shown) were injected with the selected phage and 500 µg of GST. The percentage of inhibition of selected phage homing to lung or skin in the presence of the cognate GST-fusion peptide compared to GST is shown.

FIG. 6 shows binding of phage bearing peptide CGFECVRQCPERC (SEQ ID NO: 1; GFE-1) or CGFELETC (SEQ ID NO: 2; GFE-2) to COS-1 cells expressing membrane dipeptidase (MDP).

FIG. 9 shows an alignment of the predicted amino acid sequences of membrane dipeptidase from five species. The amino acid sequences of the human ("HUM;" SEQ ID NO: 448); pig ("PIG;" SEQ ID NO: 449); rat ("RAT;" SEQ ID NO: 450); and mouse ("MOU;" SEQ ID NO: 451) MDPs are aligned together with the sequence of rabbit MDP ("RAB;" SEQ ID NO: 452). Asterisks indicate N-linked glycosylation sites in human MDP. The boxed residues $Glu^{125}$ and $His^{219}$ are essential for activity (Adachi et al., *Biochim. Biophys. Acta* 1163:42–48 (1993); Keynan et al., *FEBS Letters* 349:50–54 (1994)). Underlined residues (–1 to –16) represent the signal peptide. The boxed residues at the C-terminus indicate the hydrophobic signal that is replaced by a glycosyl-phosphatidylinositol (GPI) anchor in the mature protein. The site of GPI anchor addition is indicated by an arrow.

DETAILED DESCRIPTION OF THE INVENTION

Figure 1:
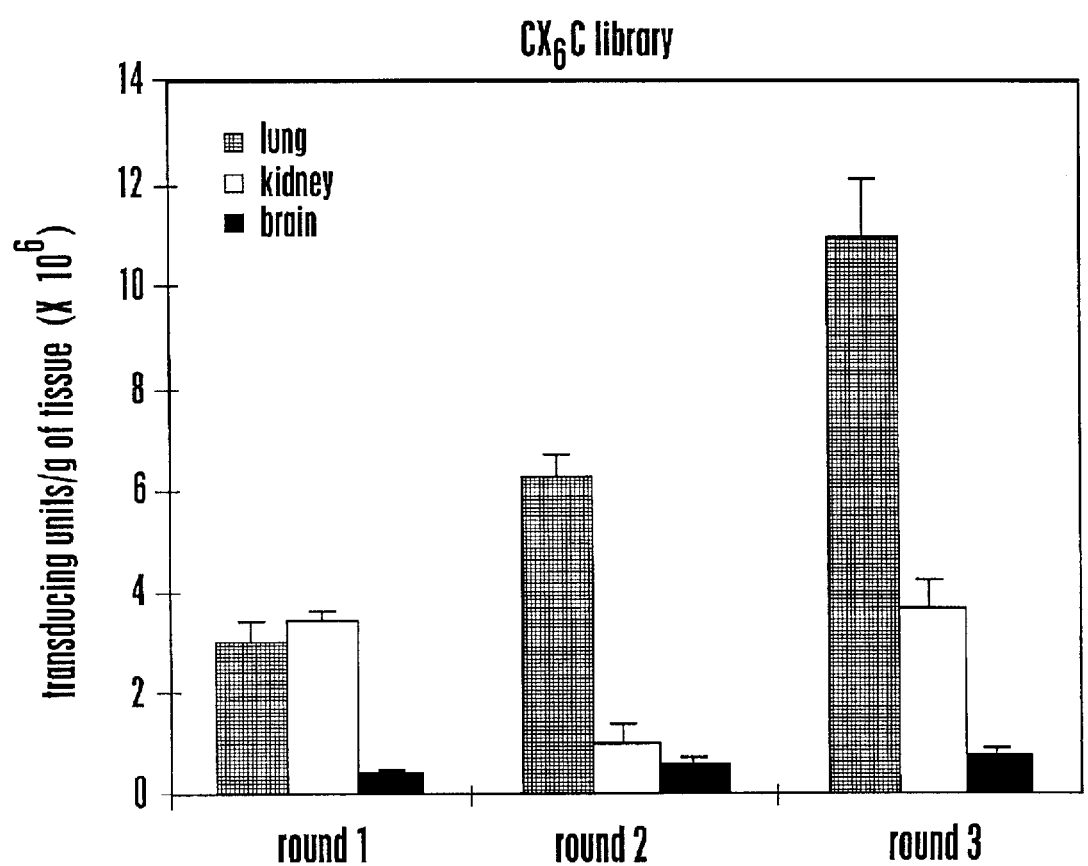
FIG. 1 shows the results of three rounds of in vivo panning of a $CX_6C$ (SEQ ID NO: 26) library for identifying molecules that home to lung. Phage recovered from the lung five minutes after injection of $10^{10}$ transducing units into the tail vein of mice were amplified and reinjected in two consecutive rounds. The number of phage recovered per gram of lung, kidney or brain is indicated for each round, with bars representing standard error of the mean from triplicate platings.
Figure 2A:
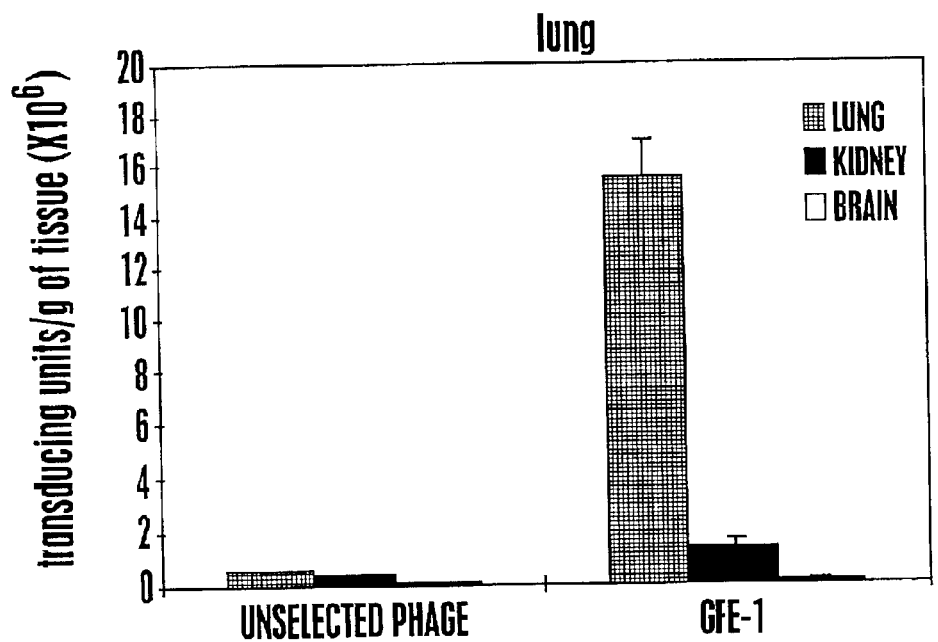
FIGS. 2A to 2D show the selectivity of phage displaying a lung (FIGS. 2A and B), skin (FIG. 2C) or pancreas (FIG. 2D) homing peptides. Selected phage expressing peptides that home to lung (FIG. 2A, CGFECVRQCPERC, SEQ ID NO: 1, "GFE-1"
Figure 2B:
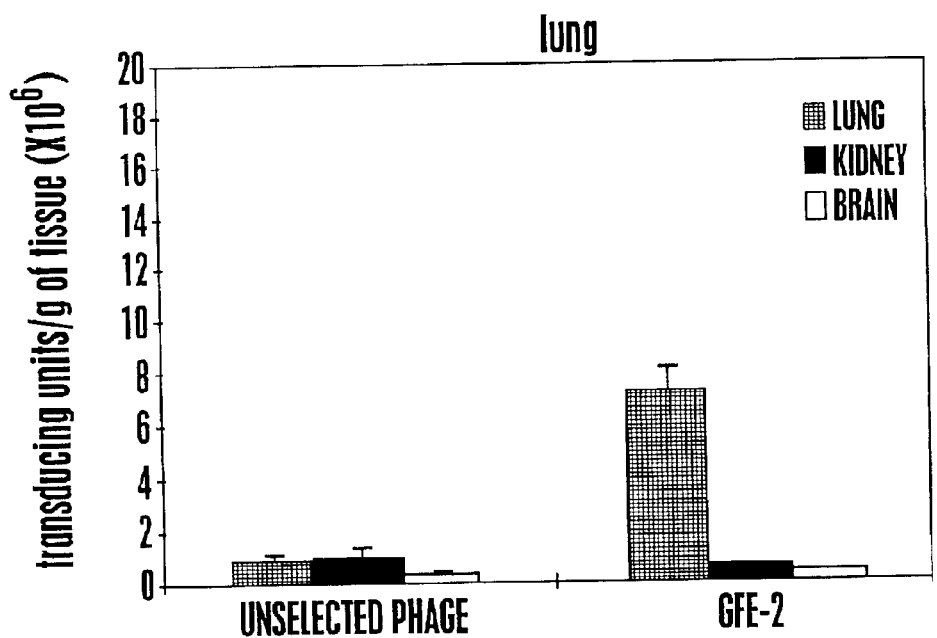
Figure 2C:
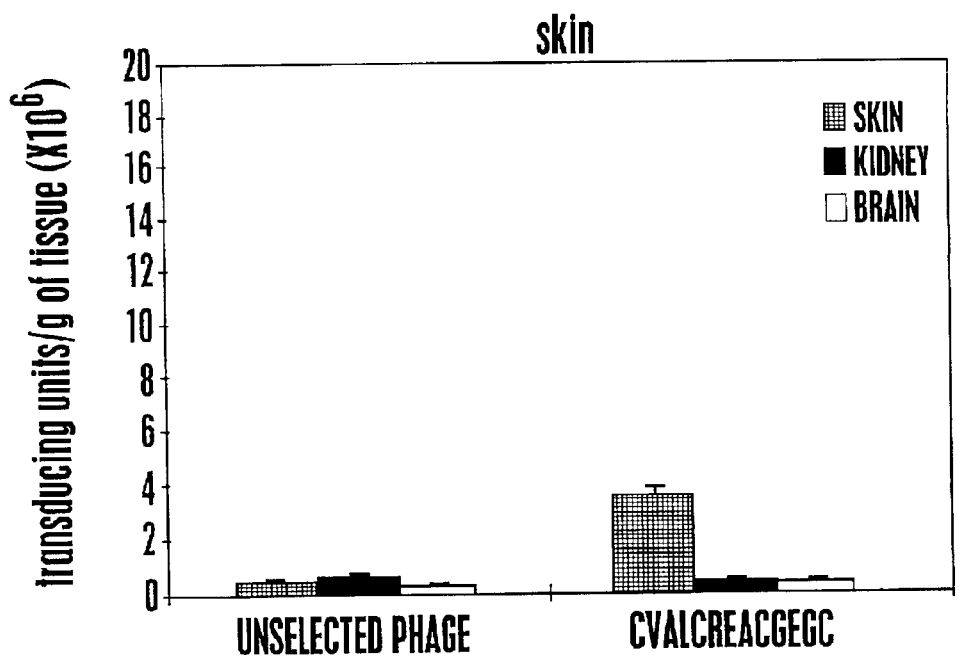
Figure 2D:
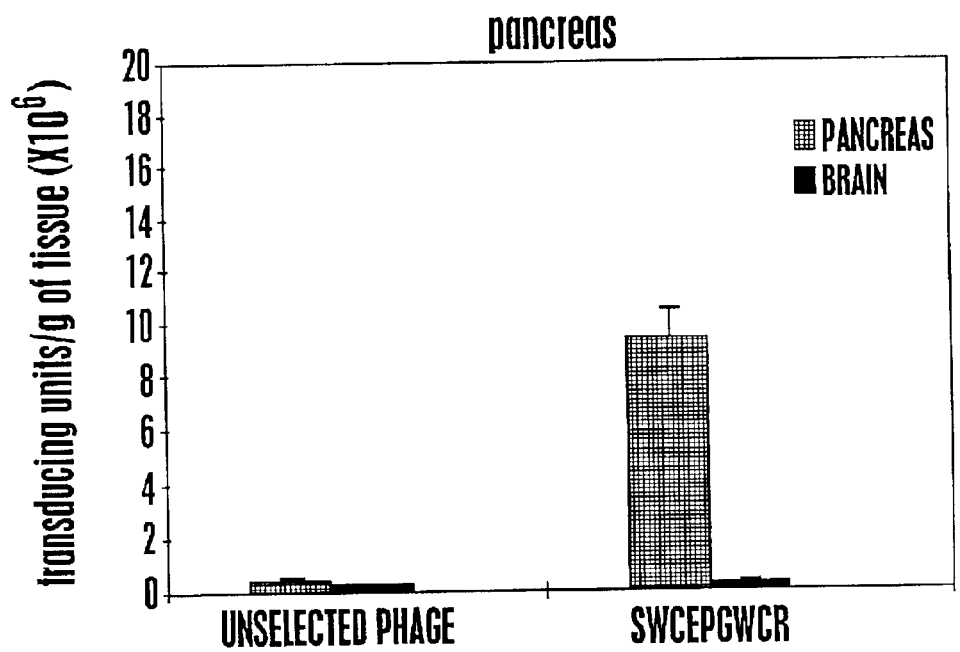

The present invention provides organ and tissue homing molecules and methods of using these molecules to target a moiety to a selected organ or tissue. The molecules of the invention, which were identified essentially by the method of in vivo panning (U.S. Pat. No. 5,622,699, issued Apr. 22, 1997, which is incorporated herein by reference), include peptides that home to various normal organs or tissues, including lung, skin, pancreas, retina, prostate, ovary, lymph node, adrenal gland, liver or gut, and to organs bearing tumors, including to lung bearing lung tumors and to pancreas bearing a pancreatic tumor. For example, the invention provides lung homing peptides, including the peptides CGFECVRQCPERC (SEQ ID NO: 1) and CGFELETC (SEQ ID NO: 2), each of which contains a tripeptide GFE motif, and the peptide GIGEVEVC (SEQ ID NO: 8). The invention also provides skin homing peptides such as the peptide CVALCREACGEGC (SEQ ID NO: 3); pancreas homing peptides such as the peptide SWCEPGWCR (SEQ ID NO: 4) and retina homing peptides such as the peptides CSCFRDVCC (SEQ ID NO: 5) and CRDVVSVIC (SEQ ID NO: 6), each of which contains a tripeptide RDV motif. Examples of peptides that home to prostate, ovary, lymph node, adrenal gland, liver and gut are also provided (see Tables 2 to 11). It should be recognized that motifs common to particular organ homing peptides can be identified by simple inspection of the peptides. For example, inspection of Table 9 reveals that the peptides AGCSVTVCG (SEQ ID NO: 315) and AGCVQSQCY (SEQ ID NO: 370) share an AGC motif; the peptides LECRRWRCD (SEQ ID NO: 328) and LECVANLCT (SEQ ID NO: 337) share an LEC motif; and the peptides SECAYRACS (SEQ ID NO: 319) and SECYTGSCP (SEQ ID NO: 375) share an SEC motif. In addition, several of these peptides were isolated more than one time (see asterisks in Table 9), indicating that such motifs are relevant to the ability of the peptides to selectively home. Peptides comprising the particular motifs disclosed herein, as well as other motifs identifiable by inspection of the disclosed peptides, are considered within the claimed invention, provided that the motif is not an RGD motif.

The homing molecules of the invention are useful for targeting a moiety to a particular organ or tissue. Thus, the invention provides conjugates, comprising an organ homing molecule linked to a moiety. Such moieties can be a therapeutic agent such as a virus; a viral gene therapy vector; a drug; a detectable or imaging agent such as a radionuclide; or a tag such as biotin. As disclosed herein, such organ homing molecules of the invention, particularly conjugates of the invention, can be used to detect or visualize a selected organ or tissue or to diagnose or treat a pathology in a selected organ or tissue. An organ homing molecule of the invention also can be used to isolate the target molecule that is expressed in the selected organ or tissue and binds the organ homing molecule. For convenience, a molecule of the invention that homes to a selected organ or tissue is referred to as an "organ homing molecule."

As used herein, the term "molecule" is used broadly to mean an organic compound having at least one reactive group that can be varied by substituting one or more different groups. An organic molecule can be a drug; a nucleic acid molecule, including RNA or DNA; a peptide; a variant or modified peptide or a peptide mimetic; a protein or a fragment thereof; an oligosaccharide; a lipid; a glycolipid; or a lipoprotein.

An organic molecule can be a naturally occurring molecule, which can be a product of nature in that the groups comprising the organic molecule and the bonds linking the groups are produced by biological processes. For example, a naturally occurring organic molecule can be an RNA molecule or a fragment thereof, which can be isolated from a cell or expressed from a recombinant nucleic acid molecule. Similarly, a peptide is considered a naturally occurring organic molecule, even if it is produced by chemical synthesis, since the amino acid groups and bonds linking the groups can be produced by normal biological processes and the peptide, itself, can be produced in a cell due, for example, to proteolytic degradation of a protein containing the peptide.

An organic molecule also can be a nonnaturally occurring molecule. Such molecules have chemical groups or bonds that are not normally produced by biological processes. For example, a nucleic acid sequence containing nonnaturally occurring nucleoside analogs or phosphorothioate bonds that link the nucleotides and protect against degradation by nucleases are examples of nonnaturally occurring molecules. A ribonucleotide containing a 2-methyl group, instead of the normal hydroxyl group, bonded to the 2'-carbon atom of ribose residues, is an example of a non-naturally occurring RNA molecule that is resistant to enzymatic and chemical degradation. Other examples of nonnaturally occurring organic molecules include RNA containing 2'-aminopyrimidines, such RNA being 1000× more stable in human serum and urine as compared to naturally occurring RNA (see Lin et al., *Nucl. Acids Res.*, 22:5229–5234 (1994); and Jellinek et al., *Biochemistry*, 34:11363–11372 (1995), each of which is incorporated herein by reference).

For convenience, the term "peptide" is used broadly herein to mean peptides, polypeptides, proteins and fragments of proteins. Other molecules useful in the invention include peptoids, peptidomimetics and the like. With respect to the organ or tissue homing peptides of the invention, peptidomimetics, which include chemically modified peptides, peptide-like molecules containing nonnaturally occurring amino acids, peptoids and the like, have the binding activity of an organ homing peptide upon which the peptidomimetic is derived (see, for example, "Burger's Medicinal Chemistry and Drug Discovery" 5th ed., vols. 1 to 3 (ed. M. E. Wolff; Wiley Interscience 1995), which is incorporated herein by reference). Peptidomimetics provide various advantages over a peptide, including that a peptidomimetic can be stable when administered to a subject, for example, during passage through the digestive tract and, therefore, useful for oral administration.

Methods for identifying a peptidomimetic are well known in the art and include, for example, the screening of databases that contain libraries of potential peptidomimetics. For example, the Cambridge Structural Database contains a collection of greater than 300,000 compounds that have known crystal structures (Allen et al., *Acta Crystallogr.* Section B, 35:2331 (1979)). This structural depository is continually updated as new crystal structures are determined and can be screened for compounds having suitable shapes, for example, the same shape as an organ or tissue homing molecule, as well as potential geometrical and chemical complementarity to a target molecule bound by an organ or tissue homing peptide. Where no crystal structure of a homing peptide or a target molecule, which binds an organ or tissue homing molecule, is available, a structure can be generated using, for example, the program CONCORD (Rusinko et al., *J. Chem. Inf. Comput. Sci.* 29:251 (1989)). Another database, the Available Chemicals Directory (Molecular Design Limited, Informations Systems; San Leandro Calif.), contains about 100,000 compounds that are commercially available and also can be searched to identify potential peptidomimetics of an organ or tissue homing molecule.

The term "nucleic acid molecule" also is used broadly to mean any polymer of two or more nucleotides, which are linked by a covalent bond such as a phosphodiester bond, a thioester bond, or any of various other bonds known in the art as useful and effective for linking nucleotides. Such nucleic acid molecules can be linear, circular or supercoiled, and can be single stranded or double stranded DNA or RNA or can be a DNA/RNA hybrid.

As used herein, the term "library" means a collection of molecules. A library can contain a few or a large number of different molecules, varying from about two to about $10^{15}$ molecules or more. The chemical structure of the molecules of a library can be related to each other or be diverse. If desired, the molecules constituting the library can be linked to a common or unique tag, which can facilitate recovery and/or identification of the molecule.

Methods for preparing libraries containing diverse populations of various types of molecules such as peptides, peptoids and peptidomimetics are well known in the art and various libraries are commercially available (see, for example, Ecker and Crooke, *Biotechnology* 13:351–360 (1995), and Blondelle et al., *Trends Anal. Chem.* 14:83–92 (1995), and the references cited therein, each of which is incorporated herein by reference; see, also, Goodman and Ro, *Peptidomimetics for Drug Design*, in "Burger's Medicinal Chemistry and Drug Discovery" Vol. 1 (ed. M. E. Wolff; John Wiley & Sons 1995), pages 803–861, and Gordon et al., *J. Med. Chem.* 37:1385–1401 (1994), each of which is incorporated herein by reference). Where a molecule is a peptide, protein or fragment thereof, the molecule can be produced in vitro directly or can be expressed from a nucleic acid, which can be produced in vitro. Methods of synthetic peptide and nucleic acid chemistry are well known in the art.

A library of peptide molecules also can be produced, for example, by constructing a cDNA expression library from mRNA collected from a cell, tissue, organ or organism of interest. Methods for producing such libraries are well known in the art (see, for example, Sambrook et al., *Molecular Cloning: A Laboratory Manual* (Cold Spring Harbor Laboratory Press 1989), which is incorporated herein by reference). Preferably, a peptide encoded by the cDNA is expressed on the surface of a cell or a virus containing the cDNA. For example, cDNA can be cloned into a phage vector such as fuse 5 (Example I), wherein, upon expression, the encoded peptide is expressed as a fusion protein on the surface of the phage.

In addition, a library of molecules can be a library of nucleic acid molecules, which can be DNA, RNA or analogs thereof. For example, a cDNA library can be constructed from mRNA collected from a cell, tissue, organ or organism of interest, or by collecting genomic DNA, which can be treated to produce appropriately sized fragments using restriction endonucleases or methods that randomly fragment genomic DNA. A library comprising RNA molecules also can be constructed by collecting RNA from cells or by synthesizing the RNA molecules chemically. Diverse libraries of nucleic acid molecules can be made using solid phase synthesis, which facilitates the production of randomized regions in the molecules. If desired, the randomization can be biased to produce a library of nucleic acid molecules containing particular percentages of one or more nucleotides at a position in the molecule (U.S. Pat. No. : 5,270,163, issued Dec. 14, 1993, which is incorporated herein by reference).

If desired, the nucleic acid molecules can be nucleic acid analogs that are less susceptible to degradation by nucleases. For example, RNA molecules containing 2'-O-methylpurine substitutions on the ribose residues and short phosphorothioate caps at the 3'- and 5'-ends exhibit enhanced resistance to nucleases (Green et al., *Chem. Biol.*, 2:683–695 (1995), which is incorporated herein by reference). Similarly, RNA containing 2'-amino-2'-deoxypyrimidines or 2'-fluro-2'-deoxypyrimidines is less susceptible to nuclease activity (Pagratis et al., *Nature Biotechnol.*, 15:68–73 (1997), which is incorporated herein by reference). Furthermore, L-RNA, which is a stereoisomer of naturally occurring D-RNA, is resistant to nuclease activity (Nolte et al., *Nature Biotechnol.*, 14:1116–1119 (1996); Klobmann et al., *Nature Biotechnol.*, 14:1112–1115 (1996); each of which is incorporated herein by reference). Such RNA molecules and methods of producing them are well known and routine (see Eaton and Piekern, *Ann. Rev. Biochem.*, 64:837–863 (1995), which is incorporated herein by reference). DNA molecules containing phosphorothioate linked oligodeoxynucleotides are nuclease resistant (Reed et al., *Cancer Res.* 50:6565–6570 (1990), which is incorporated herein by reference). Phosphorothioate-3' hydroxypropylamine modification of the phosphodiester bond also reduces the susceptibility of a DNA molecule to nuclease degradation (see Tam et al., *Nucl. Acids Res.*, 22:977–986 (1994), which is incorporated herein by reference). If desired, the diversity of a DNA library can be enhanced by replacing thymidine with 5-(1-pentynyl)-2'-deoxoridine (Latham et al., *Nucl. Acids Res.* 22:2817–2822 (1994), which is incorporated herein by reference). Such modified nucleic acid molecules can be useful for the manufacture of a library or for the purpose of being a tag, which is described later below.

As disclosed herein, in vivo panning for the purpose of identifying an organ or tissue homing molecule comprises administering a library to a subject, collecting an organ or tissue sample and identifying an organ or tissue homing molecule using various methods well known in the art. Generally, the presence of an organ or tissue homing molecule in a collected organ or tissue is identified based on one or more characteristics common to the molecules present in the library, then the structure of a particular organ or tissue homing molecule can be determined.

A highly sensitive detection method such as mass spectrometry (MS), either alone or in combination with a method such as gas chromatography (GC), can be used to identify homing molecules that are closely related even when present in small amounts in a selected organ or tissue. For example, GC in combination with MS was used to identify two major and four minor lidocaine metabolites following lidocaine injection into rats and the analysis of urine (Coutts et al., *J. Chromotogr.* 421:267–280 (1987), which is incorporated herein by reference). Similarly, where a library comprises diverse molecules based generally on the structure of an organic molecule such as a drug, an organ or tissue homing molecule can be identified by determining the presence of a parent peak for the particular molecule.

If desired, the selected organ or tissue can be processed using a method such as HPLC, which can be used to obtain an enriched fraction of molecules having a defined range of molecular weights or polarity or the like from a complex mixture. The enriched fraction of molecules then can be further analyzed for the purposes of identifying organ or tissue homing molecules. For example, HPLC coupled with GC and MS were used to identify seven metabolites of a vitamin D analogue after injection of dihydrotachysterol 3 into a rat and fractionation of an isolated perfused kidney (Porteous et al., *Biomed. Environ. Mass Spectrum* 16:87–92 (1988), which is incorporated herein by reference). Conditions for HPLC will depend on the structure of the particular molecule and can be optimized by those skilled in the art based on knowledge of the molecule.

The organ homing molecules present in a collected sample of organ or tissue can be recovered from the sample by incubation in a solution having a defined salt concentration and temperature. Selective extraction also can be used to obtain different fractions of organic molecules by sequentially incubating a collected sample in one or more solutions. Such solutions can have a different salt concentration or can effect extraction of an organic homing molecule at a particular temperature. The resulting eluates from the collected sample can be collected separately or can be pooled into one or more fractions and the organ homing molecules can be detected and identified. Similarly, methods for bulk removal of potentially interfering cellular materials such as DNA, RNA, proteins, lipids or carbohydrates are well known in the art. Such methods can be used to enrich for the particular organ homing molecule from potentially contaminating materials in the collected sample and to increase the sensitivity of detecting the molecule.

Ease of identification of an organ or tissue homing molecule, particularly an untagged molecule, depends upon various factors, including the presence of potentially contaminating background cellular material. For example, where the homing molecule is an untagged peptide, a larger number must home to the organ or tissue in order to identify the specific peptides over the background of cellular protein. In contrast, a much smaller amount of an untagged homing molecule such as a drug is identifiable because such molecules normally are generally absent from or present in very small numbers in the body. In this situation, a highly sensitive method such as MS can be used to identify an organ homing molecule. The skilled artisan will recognize that the method of identifying a molecule will depend, in part, on the structure of the particular molecule.

As disclosed herein, a sufficient number of molecules selectively home to a selected organ or tissue during in vivo panning such that the molecules readily can be identified. For example, peptides that were identified two or more times in a particular collected organ (see Table 1). For example, of forty clones sequenced from various selected organs, the gut homing peptide YSGKWGK (SEQ ID NO: 9) was present in 22% of the clones; the ovary homing peptides EVRSRLS (SEQ ID NO: 10) and RVGLVAR (SEQ ID NO: 11) each was present in 22% of the clones; and the liver homing peptide VKSVCRT (SEQ ID NO: 12) was present in 11% of the clones (see Table 1). Similarly, the lung homing peptides CLAKENVVC (SEQ ID NO: 13) and CGFECVRQCPERC (SEQ ID NO: 1); the skin homing peptide CVAL-CREACGEGC (SEQ ID NO: 3); and the retina homing peptide CGEFKVGC (SEQ ID NO: 14) each was independently isolated several times during in vivo panning of the respective organs, as were other organ homing peptides (see Tables 2 to 11; peptides marked with asterisk). These results demonstrate that a substantial fraction of the identified organ homing molecules have the same structure or, in many cases, share conserved motifs.

Following various in vivo panning screens, hundreds of thousands to millions of phage expressing homing peptides were recovered from the respective organ or tissue. Generally, the phage collected from a round of in vivo panning were plated on agar, about 250 to 300 clones were selected, grown in 5 ml cultures, then pooled and readministered for a subsequent round of in vivo panning ("regular method"). However, in some experiments, 1000 clones were selected, grown in 2 ml cultures, then pooled and administered for a subsequent round of screening; or the entire agar plate was scraped and all of the phage were cultured together and administered for a subsequent round of screening. The peptide inserts of various isolated phage were determined such that, of the millions of phage that homed, only a small number of sequences were identified. These results indicate that specific types of homing molecules can be present in relatively large proportions in an organ or tissue following in vivo homing, thereby increasing the ease with which the molecules can be identified.

Where an organ or tissue homing molecule is a nucleic acid molecule, various assay methods can be used to substantially isolate or identify the molecule. For example, PCR can be particularly useful for identifying the presence of the homing molecule because, in principle, PCR can detect the presence of a single nucleic acid molecule (see, for example, Erlich, *PCR Technology: Principles and Applications for DNA Amplification* (Stockton Press (1989), which is incorporated herein by reference). PCR also has been used to amplify nucleic acid molecules that bind to a predetermined target in vitro and, when the nucleic acids were rendered resistant to nucleases and administered to a subject, they modulated biological processes such as lymphocyte trafficking in vivo (see, for example, Hicke et al., *J. Clin. Invest.* 98:2688–2692 (1996), which is incorporated herein by reference). These findings indicate that nucleic acid molecules are sufficiently stable when administered into the circulation of a subject such that in vivo panning can be used to identify nucleic acid molecules that selectively home to an organ or tissue in vivo.

The molecules of a library can be tagged, which can facilitate recovery or identification of the organ homing molecules. As used herein, the term "tag" means a physical, chemical or biological moiety such as a plastic or metallic microbead, an oligonucleotide or a bacteriophage, respectively, that is linked to a molecule of the library. Methods for tagging a molecule are well known in the art (Hermanson, *Bioconjugate Techniques*, (Academic Press 1996), which is incorporated herein by reference). The link between a molecule and a tag can be a covalent or a non-covalent bond and, if desired, the link can be selectively cleavable from the molecule.

As used herein, the term "shared tag" means a physical, chemical or biological moiety that is common to each molecule in a library. A shared tag can be used to identify the presence of a molecule of the library in a sample or to substantially isolate the molecules from a sample following in vivo panning. For example, a library that comprises a population of diverse molecules such as nucleic acids can be linked to a shared tag. If the shared tag is biotin, for example, a nucleic acid homing molecule can be substantially isolated from a selected organ or tissue by binding, for example, to a streptavidin affinity column. The presence of the organ or tissue homing nucleic acid molecule also can be detected by binding with a labeled streptavidin. A peptide such as the hemagglutinin antigen also can be a shared tag, which, when linked to each molecule in a library, allows the use of an antibody specific for the hemagglutinin antigen to substantially isolate homing molecules from a selected organ or tissue. Furthermore, a molecule or a support containing a molecule can be linked to a hapten such as 4-ethoxy-methylene-2-phenyl-2-oxazoline-5-one (phOx), which can be bound by an anti-phOx antibody linked to a magnetic bead as a means to recover the homing molecule. Methods for purifying phOx labeled conjugates are known in the art and the materials for performing these procedures are commercially available (Invitrogen, La Jolla Calif.; Promega Corp., Madison Wis.).

A shared tag also can be a nucleic acid sequence that can be used to identify the presence of molecules of the library in a sample or to substantially isolate molecules of a library from a sample. For example, each of the molecules of a library can be linked to the same selected nucleotide sequence, which constitutes the shared tag. An affinity column containing a nucleotide sequence that is complementary to the shared tag then can be used to isolate the homing molecules from an organ or tissue sample by hybridizing to the shared tag linked to the molecules. A nucleotide sequence complementary to a portion of the shared tag also can be used as a PCR primer such that the presence of molecules containing the shared tag can be identified in a sample by PCR.

A tag also can be a specific or a unique tag. As used herein, the term "specific tag" means a physical, chemical or biological tag that is linked to a molecule in a library and that is unique for the particular molecule. A specific tag is particularly useful if it is readily identifiable. A nucleotide sequence that is unique for a particular molecule of a library is an example of a specific tag, for example, a unique oligonucleotide tag linked to each peptide of a library or peptides (see, for example, Brenner and Lerner, *Proc. Natl. Acad. Sci., USA* 89:5381–5383 (1992), which is incorporated herein by reference). Upon homing to an organ or tissue, the homing peptide can be identified by determining the sequence of the unique oligonucleotide tag using, for example, PCR (see, for example, Erlich, *PCR Technology: Principles and Applications for DNA Amplification* (Stockton Press 1989), which is incorporated herein by reference). Similarly, the nucleic acid sequence encoding a peptide displayed on a phage is another example of a specific nucleic acid tag, since sequencing of the nucleic acid identifies the amino acid sequence of the expressed peptide (see Example I). Such unique oligonucleotide sequence tags, when linked to other libraries of molecules, can be used to identify the sequence of the homing molecule linked thereto.

A shared tag and specific tag, in combination, can be particularly useful for isolating and identifying an organ or tissue homing molecule when the homing molecule is present in minute quantities. For example, each molecule of a library can be linked to an oligonucleotide tag which contains two portions; an internal unique nucleotide sequence tag and shared flanking 5' and 3' nucleotide tags that serve as primer binding sites for use in PCR. Each molecule, therefore, contains an oligonucleotide tag having a unique portion to identify the homing molecule and a shared portion to provide PCR primer binding sites. Such a tagged molecule, upon homing to a selected organ or tissue, can be identified by performing PCR using primers that hybridize to the shared flanking 5' and 3' nucleotide tags, then performing DNA sequencing to determine the nucleotide sequence of the internal unique sequence tag. The PCR product can be sequenced directly using one of the PCR primers or the PCR product can be cloned into a vector and the DNA sequence determined by routine methods well known in the art.

Various other combinations of shared and unique tags can be used. For example, each of the molecules in a library can be linked to a specific nucleotide sequence tag (see, for example, Brenner and Lerner, supra, 1992), which also contains a shared 3' nucleotide sequence that can be a primer binding site for use in PCR, and can be further linked to a shared tag such as biotin. Upon homing to an organ or tissue, the particular homing molecule can be substantially isolated from an organ or tissue sample based on the biotin tag. The isolated molecules can then be identified, for example, by PCR based DNA sequencing of the specific tag using the shared 3' nucleotide sequence of the nucleotide tag as a primer binding site.

A tag also can serve as a support. As used herein, the term "support" means a tag having a defined surface to which a molecule can be attached. In general, a tag useful as a support is a shared tag. For example, a support can be a biological tag such as a virus or virus-like particle such as a bacteriophage ("phage"); a bacterium such as $E.$ $coli$; or a eukaryotic cell such as a yeast, insect or mammalian cell; or can be a physical tag such as a liposome or a microbead, which can be composed of a plastic, agarose, gelatin or other biological or artificial material. If desired, a shared tag useful as a support can have linked thereto a specific tag.

As exemplified herein, a peptide suspected of being able to home to a selected normal organ or tissue such as lung, skin, pancreas, retina, prostate, ovary, lymph node, adrenal gland, liver or gut, or to an organ or tissue containing a tumor, for example, a lung containing lung tumors or a pancreas containing a pancreatic tumor, was expressed as the N-terminus of a fusion protein, wherein the C-terminus consisted of a phage coat protein (see Example I). Upon expression of the fusion protein, the C-terminal coat protein linked the fusion protein to the surface of a phage such that the N-terminal peptide was in a position to interact with a target molecule in the organ or tissue. Thus, a molecule having a shared tag was formed by the linking of a peptide to a phage, wherein the phage provided a biological support, the peptide molecule was linked as a fusion protein, the phage-encoded portion of the fusion protein acted as a spacer molecule, and the nucleic acid encoding the peptide provided a specific tag alloying identification of organ and tissue homing peptides.

Where a molecule is linked to a support, the tagged molecule comprises the molecule attached to the surface of the support, such that the part of the molecule suspected of being able to interact with a target molecule in a cell in the subject is positioned so as to be able to participate in the interaction. For example, where the homing molecule is suspected of being a ligand for a growth factor receptor, the binding portion of the molecule attached to a support is positioned so it can interact with the growth factor receptor on a cell in an organ or tissue. If desired, an appropriate spacer can be positioned between the molecule and the support such that the ability of the potential organ or tissue homing molecule to interact with the target molecule is not hindered. A spacer molecule also can contain a reactive group, which provides a convenient and efficient means of linking a molecule to a support and, if desired, can contain a tag, which can facilitate recovery or identification of the molecule (see Hermanson, supra, 1996).

In general, a support should have a diameter less than about 10 $\mu$m to about 50 $\mu$m in its shortest dimension, such that the support can pass relatively unhindered through the capillary beds present in the subject so as to not occlude circulation. In addition, a support can be biologically inert, so that it does not perturb the normal expression of cell surface molecules or normal physiology of the subject. In addition, a support can be excretable or biodegradable, particularly where the subject used for in vivo panning is not sacrificed to collect a sample of a selected organ or tissue.

As used herein, the term "in vivo panning," when used in reference to the identification of an organ or tissue homing molecule, means a method of screening a library by administering the library to a subject and identifying a molecule that selectively homes to an organ or tissue in the subject (U.S. Pat. No. 5,622,699, supra, 1997). The term "administering to a subject", when used in referring to a library of molecules or a portion of such a library, is used in its broadest sense to mean that the library is delivered to a selected organ or tissue in the subject, which, generally, is a vertebrate, particularly a mammal such as a human. Libraries of molecules can be administered by any route or means of administration, such as intravenously, intramuscularly, orally, optically, ocularly, intraperitoneally, nasally, vaginally, rectally, into the uterus, into a chamber of the eye, into the central or peripheral nervous system, by inhalation, by topical administration, or by injection into any normal organ or tissue or into a pathological region such as a tumor or an organ or tissue involved in a pathology, particularly into the circulatory system of the organ or tissue.

A library can be administered to a subject, for example, by injecting the library into the circulation of the subject such that the molecules pass through the selected organ or tissue; after an appropriate period of time, circulation is terminated, for example, by perfusion through the heart or by removing a sample of the organ or tissue (Example I; U.S. Pat. No. 5,622,699, supra, 1997; see, also, Pasqualini and Ruoslahti, $Nature$ 380:364–366 (1996), which is incorporated herein by reference). Alternatively, a cannula can be inserted into a blood vessel in the subject, such that the library is administered by perfusion for an appropriate period of time, after which the library can be removed from the circulation through the cannula or the subject can be sacrificed or anesthetized to collect an organ or tissue sample. A library also can be shunted through one or a few organs or tissues including a selected organ or tissue, by cannulation of the appropriate blood vessels in the subject. It is recognized that a library also can be administered to an isolated perfused organ or tissue. Such panning in an isolated perfused organ or tissue can be useful to identify molecules that bind to the organ or tissue.

The use of in vivo panning to identify organ or tissue homing molecules is exemplified herein by screening a phage peptide display library in mice and identifying peptides that selectively homed to lung, pancreas, skin and others, and in rats, for peptides that homed to retina (Examples I and II). However, phage libraries that display other protein molecules, including, for example, an antibody or an antigen binding fragment of an antibody such an Fv, Fd or Fab fragment; a hormone receptor such as a growth factor receptor; or a cell adhesion receptor such as an integrin or a selectin also can be used to practice the invention. Variants of such molecules can be constructed using well known methods such as random, site directed or codon based mutagenesis (see Huse, U.S. Pat. No. 5,264,563, issued Nov. 23, 1993, which is incorporated herein by reference) and, if desired, peptides can be chemically modified, for example, by introducing a disulfide bridge, following expression of the phage but prior to administration to the subject. Thus, many different types of phage display libraries can be screened by in vivo panning.

Phage display technology provides a means for expressing a diverse population of random or selectively randomized peptides. Various methods of phage display and methods for producing diverse populations of peptides are well known in the art. For example, Ladner et al. (U.S. Pat. No. 5,223,409, issued Jun. 29, 1993, which is incorporated herein by reference) describe methods for preparing diverse populations of binding domains on the surface of a phage. In particular, Ladner et al. describe phage vectors useful for producing a phage display library, as well as methods for selecting potential binding domains and producing randomly or selectively mutated binding domains.

Similarly, Smith and Scott (*Meth. Enzymol.* 217:228–257 (1993); see, also, Scott and Smith, *Science* 249: 386–390 (1990), each of which is incorporated herein by reference) describe methods of producing phage peptide display libraries, including vectors and methods of diversifying the population of peptides that are expressed (see, also, Huse, WO 91/07141 and WO 91/07149, each of which is incorporated herein by reference; see, also, Example I). Phage display technology can be particularly powerful when used, for example, with a codon based mutagenesis method, which can be used to produce random peptides or randomly or desirably biased peptides (Huse, U.S. Pat. No. 5,264,563, supra, 1993). These or other well known methods can be used to produce a phage display library, which can be subjected to the in vivo panning method of the invention in order to identify a peptide that homes to a selected organ or tissue.

In addition to screening a phage display library, in vivo panning can be used to screen various other types of libraries. For example, nucleic acid molecules that bind to a cell surface receptor have been described (see O'Connell et al., *Proc. Natl. Acad. Sci., USA* 93:5683–5887 (1996); Tuerk and Gold, *Science* 249:505–510 (1990); Gold et al., supra (1995), each of which is incorporated herein by reference). These in vitro results indicate that a library of nucleic acid molecules also can be examined by in vivo panning to identify nucleic acid molecules that home to a selected organ or tissue. Additional libraries suitable for screening include, for example, oligosaccharide libraries (York et al., *Carb. Res.* 285:99–128, (1996); Liang et al., *Science* 274:1520–15221 (1996); and Ding et al., *Adv. Expt. Med. Biol.* 376:261–269, (1995), each of which is incorporated by reference); lipoprotein libraries (de Kruif et al., *FEBS Lett.* 399:232–236, (1996), which is incorporated herein by reference); glycoprotein or glycolipid libraries (Karaoglu et al., *J. Cell Biol.* 130:567–577 (1995), which is incorporated herein by is reference); or chemical libraries containing, for example, drugs or other pharmaceutical agents (Gordon et al., *J. Med. Chem.* 37:1385–1401 (1994); Ecker and Crook, *Bio/Technology* 13:351–360 (1995); each of which is incorporated by reference). Such libraries, if desired, can be tagged, which can facilitate recovery of the molecule from an organ or tissue or its identification as previously described.

In vivo panning provides a method for directly identifying molecules that can selectively home to an organ or tissue. As used herein, the term "home" or "selectively home" means that a particular molecule binds relatively specifically to a target molecule present in the organ or tissue, particularly in the vasculature present in the organ or tissue, following administration to a subject. In general, selective homing is characterized, in part, by detecting at least a two-fold (2×) greater selective binding of the molecule to an organ or tissue as compared to a control organ or tissue.

Selective homing of a molecule to a selected organ or tissue can be due to selective recognition by the molecule of a particular cell target molecule such as a cell surface protein present on a cell in the organ or tissue. Selectivity of homing is dependent on the particular target molecule being expressed on only one or a few different cell types, such that the molecule homes to only one or a few organs or tissues. In this regard, most different cell types, particularly cell types that are unique to an organ or tissue, can express unique target molecules. Thus, in organs such as liver, spleen or lymph node, where blood circulates through sinusoids formed by the cells specific for the organ, in vivo panning can be useful for identifying molecules that home to the particular organ or tissue.

It should be recognized that, in some instances, a molecule can localize nonspecifically to an organ or tissue. For example, in vivo panning of a phage display library can result in high background in organs such as liver and spleen, which contain a marked component of the reticuloendothelial system (RES). Thus, nonspecific binding of molecules due to uptake by the RES of such an organ or tissue can make identifying an organ or tissue homing molecule more difficult. However, as disclosed herein, potential nonspecific binding can be circumvented, for example, by perfusion through the heart prior to collecting the selected organ or tissue (Example I).

In addition, selective homing readily can be distinguished from nonspecific binding by detecting differences in the abilities of different individual phage to home to an organ or tissue. For example, selective homing can be identified by combining a putative homing molecule such as a peptide expressed on a phage with an excess of non-infective phage or with about a five-fold excess of phage expressing unselected peptides, injecting the mixture into a subject and collecting a sample of the organ or tissue. In the latter case, for example, provided the portion of injected phage in which an organ or tissue homing peptide is sufficiently low so as to be nonsaturating for the target molecule, a determination that greater than about 20% of the phage in the organ or tissue contain the putative homing molecule is demonstrative evidence that the peptide expressed by the phage is a selective organ or tissue homing molecule. In addition, nonspecific localization can be distinguished from selective homing by performing competition experiments using, for example, phage expressing a putative organ or tissue homing peptide in combination with an excess amount of the "free" peptide (see Example II).

Various methods can be used to prevent nonspecific localization of a molecule to organs or tissues, such as those containing a component of the RES. For example, as disclosed herein, perfusion of a solution through the heart shortly after initiating phage circulation decreased the background binding and allowed identification of peptides that selectively home to lung and liver, both of which contain a component of the RES (see Example II). Furthermore, coadministration of nonreplicating control phage with a phage display library reduced nonspecific phage trapping in organs such as liver and spleen, which also contain a component of the RES. This approach allowed identification of molecules that selectively home to liver (Example II). Thus, a library of molecules attached to a support can be coadministered with an excess of the support to a subject to inhibit nonspecific binding in an organ or tissue.

Nonspecific uptake by a component of the RES also can be prevented by administering a blocking agent that inhibits uptake by the RES. For example, polystyrene latex particles or dextran sulfate can be administered to the subject prior to the administration of the library (see Kalin et al., *Nucl. Med. Biol.* 20:171–174 (1993); Illum et al., *J. Pharm. Sci.* 75:16–22 (1986); Takeya et al., *J. Gen. Microbiol.* 100:373–379 (1977), each of which is incorporated herein by reference). Such pre-administration of dextran sulfate 500 or polystyrene microspheres has been used to block nonspecific uptake of a test substance by Kupffer cells, which are the RES component of the liver (Illum et al., supra, 1986). Similarly, nonspecific uptake of agents by the RES has been blocked using carbon particles or silica (Takeya et al., supra, 1977) or a gelatine colloid (Kalin et al., supra, 1993). Thus, many methods useful for inhibiting nonspecific uptake by the RES are known in the art and routinely used.

Methods of decreasing nonspecific phage trapping include using phage that display a low background binding to a particular organ or tissue. For example, Merrill et al. (Proc. Natl. Acad. Sci., USA 93:3188–3192 (1996), which is incorporated herein by reference) selected lambda-type phage that are not taken up by the RES and, as a result, remain in the circulation for a prolonged period of time. A comparable filamentous phage variant, for example, can be selected using similar methods.

Selective homing can be demonstrated by determining if a homing molecule for a selected organ or tissue is relatively specific. For example, the amount of homing molecule in a selected organ or tissue can be compared to a control or different organ or tissue. Selective homing also can be demonstrated by showing that molecules that home to an organ or tissue, as identified by one round of in vivo panning, are enriched for in a subsequent round of in vivo panning. For example, phage expressing the peptides CGFECVRQCPERC (SEQ ID NO: 1) and CGFELETC (SEQ ID NO: 2) were enriched for in the second and third rounds of in vivo panning from lung and exhibited a 35-fold and 9-fold enrichment, respectively, as compared to unselected phage (see Example II.B). Furthermore, no selective homing to kidney or brain was detected.

As used herein, the term "selected organ or tissue" is used in its broadest sense to mean a normal organ or tissue or an organ or tissue having a pathology, for example, lung containing lung tumors, to which a molecule can selectively home. Thus, the term "organ or tissue" is used broadly to mean any tissue or organ including a normal or pathological cell type such as a cancer cell, in which case the selected organ or tissue can be a primary tumor or a metastatic lesion.

In general, a selected organ or tissue contains a cell, which can be a cell of the vasculature, that expresses a particular target molecule such as a cell surface protein to which a homing molecule can bind. By performing at least two rounds of in vivo panning, the selectivity of homing of the molecule for the selected organ or tissue can be determined. As discussed below, however, in some cases a homing molecule can home to more than one selected organ or tissue, in which case the molecule is considered to be able to selectively home to a family of selected organs or tissues. Generally, however, molecules that home to more than one or a few different organs or tissue are not particularly useful since an advantage of the homing molecules of the invention is that they allow targeting of a particular organ or tissue.

The term "control organ or tissue" is used to mean an organ or tissue other than the selected organ or tissue. A control organ or tissue is characterized by the inability of the organ or tissue homing molecule to home to the control organ or tissue and, therefore, is useful for identifying selective binding of a molecule to a selected organ or tissue (Example II). Where an organ or tissue homing molecule is identified based on its ability to home to a pathologic lesion in an organ or tissue, the control organ or tissue can be a corresponding portion of the selected organ or tissue that does not exhibit the pathologic lesion.

A control organ or tissue can be collected, for example, to identify nonspecific binding of the molecule or to determine the selectivity of homing of the molecule. In addition, nonspecific binding can be identified by administering, for example, a control molecule, which is known not to home to an organ or tissue but is chemically similar to a putative homing molecule. Alternatively, where the administered molecules are linked to a support, administration of the support, alone, can be used to identify nonspecific binding. For example, a phage that does not contain a peptide fusion protein can be administered to a subject and the selected organ or tissue can be examined to determine the level of nonspecific binding of the phage support.

The steps of administering the library to the subject, collecting a selected organ or tissue and identifying the molecules that home to the organ or tissue, comprise a single round of in vivo panning. Although not required, one or more additional rounds of in vivo panning generally are performed. Where an additional round of in vivo panning is performed, the molecules recovered from the selected organ or tissue in the previous round are administered to a subject, which can be the same subject used in the previous round, where only a part of the organ or tissue was collected.

By performing a second round of in vivo panning, the relative binding selectivity of the molecules recovered from the first round can be determined by administering the identified molecules to a subject, collecting the selected organ or tissue, and determining whether more phage displaying a particular molecule are recovered from the organ or tissue following the second round of screening as compared to those recovered following the first round. Although not required, a control organ or tissue also can be collected and the molecules recovered from the selected organ or tissue can be compared with those recovered from the control organ or tissue. Ideally, few if any molecules are recovered from a control organ or tissue following a second or subsequent round of in vivo panning. Generally, however, a proportion of the molecules also will be present in a control organ or tissue. In this case, the ratio of molecules in the selected organ or tissue as compared to the control organ or tissue (selected:control) can be determined. Additional rounds of in vivo panning can be used to determine whether a particular molecule homes only to the selected organ or tissue or can recognize a target expressed in one or more other organs or tissues that is identical or is sufficiently similar to the target in the originally selected organ or tissue.

In general, a library of molecules, which contains a diverse population of random or selectively randomized molecules of interest, is prepared, then administered to a subject. Some time after administration, the selected organ or tissue is collected and the molecules present in the selected organ or tissue are identified (see Example I). If desired, one or more control organs or tissues or a part of a control organ or tissue are sampled as well. For example, mice injected with a phage peptide display library, after about 1 to 5 minutes, were anesthetized, then snap frozen or perfused through the heart to terminate circulation of the phage. Lung, pancreas or other organs or tissues and one or more control organs were collected and the phage present in the selected and control organs were collected. The peptides that selectively homed to the respective organs or tissues were identified (Example II and Tables 1 to 11).

As exemplified herein, experimental animals were sacrificed to collect the selected or control organ or tissue. It should be recognized, however, that only a part of an organ or tissue need be collected to recover a molecule that homes to that organ or tissue. Similarly, only part of an organ or tissue need be collected as a control. Thus, for example, following administration of a library of molecules to a subject, a part of the selected organ or tissue can be collected by biopsy, the homing molecules can be collected and, if desired, amplified and readministered to the same subject for a second round of in vivo panning. Where the molecule that is to be administered a second time to the same subject is tagged or linked, for example, to a support, the tag or support should be biologically inert and biodegradable or excretable, so as not to interfere with subsequent rounds of screening.

In vitro screening of phage libraries previously was used to identify peptides that bind to antibodies or to cell surface receptors (Smith and Scott, supra, 1993). For example, in vitro screening of phage peptide display libraries identified novel peptides that specifically bound to integrin adhesion receptors (Koivunen et al., *J. Cell Biol.* 124:373–380 (1994a), which is incorporated herein by reference) and to the human urokinase receptor (Goodson et al., *Proc. Natl. Acad. Sci., USA* 91:7129–7133 (1994), which is incorporated herein by reference). Similarly, in vitro screening of nucleic acid molecules identified molecules that specifically bind to antibodies, cell surface receptors or organic molecules (Gold et al., supra, 1993, 1995, 1997). For example, RNA molecules that specifically bind to HIV-1 reverse transcriptase were identified using purified HIV-1 reverse transcriptase as the target molecule (Green et al., *J. Mol. Biol.*, 247:60–68 (1995), which is incorporated herein by reference). These in vitro methods were performed using defined, well-characterized target molecules in an artificial system. However, such in vitro studies provide no insight as to whether a molecule that binds in vitro also can bind to the target in vivo. For example, endothelial cells grown in culture tend to lose their tissue-specific differences (Pauli and Lee, *Lab. Invest.* 58:379–387 (1988), which is incorporated herein by reference). Thus, a molecule that binds to a target on a cell in vitro may not bind in vivo because the target may not be present on the cell. Furthermore, such in vitro methods are limited in that they require prior knowledge of the target molecule and yield little if any information regarding in vivo utility. For example, Goodson et al. (supra, 1994) utilized cultured cells to express a recombinant urokinase receptor to obtain binding peptides. However, the urokinase receptor is expressed in cells of many different organs and tissues and, therefore, a molecule that binds to it can interact with many organs or tissues and would not be considered an organ or tissue homing molecule within the present invention.

In contrast to in vitro panning methods, in vivo panning requires no prior knowledge or the availability of a known target molecule to identify a molecule that binds to a target molecule that is expressed in vivo. Also, since "nontargeted" organs or tissues are present during the screening, the probability of isolating organ or tissue homing molecules that lack selectivity of homing is greatly reduced. Furthermore, in obtaining organ or tissue homing molecules by in vivo panning, any molecules that may be particularly susceptible to degradation in the circulation in vivo due, for example, to a metabolic activity, will be selected against and will not be recovered. Thus, in vivo panning provides significant advantages over previous methods by identifying molecules that selectively home in vivo and, if desired, the target molecule present on a selected organ or tissue.

The identification of the organ homing molecules that selectively home to various normal tissues and to pathologic lesions in a particular organ or tissue, as exemplified herein, indicates that particular endothelial cell target molecules expressed the selected organ or tissue reflects the physiologic or pathologic state of the organ or tissue. Such organ homing molecules that selectively home to an organ or tissue based on a particular physiologic or pathologic condition occurring in the organ or tissue can be identified using the in vivo panning method and the selectivity of the homing molecules for the pathologic or physiologic condition of the organ or tissue can be confirmed by immunohistological analysis (Example III). For example, molecules that home to pancreas afflicted with pancreatitis can be identified by in vivo panning of a subject having pancreatitis and selectively of the homing molecule can be confirmed by using immunohistochemistry to compare homing of the molecule in normal pancreas with homing in a pancreas afflicted with pancreatitis.

Homing molecules selective for a normal organ or tissue or an organ or tissue exhibiting a pathological state can be useful for detecting the presence or absence of the pathology. For example, following administration of a prostate homing molecule conjugated to an imaging moiety to a subject, the prostate can be visualized. If the image is abnormal, for example, if the size of the prostate is other than that expected for a size and age matched subject, the imaging result can indicate an abnormal physiologic condition or pathologic condition afflicting the prostate. For example, a conjugate comprising an imaging agent and a prostate homing molecule that homes to normal, but not to abnormal prostate, can be administered to a subject. The identification, for example, of a region of the prostate that does not bind the homing molecule can indicate the occurrence of abnormal blood flow in the prostate and can be diagnostic of a pathologic condition such as the presence of a prostate tumor. A conjugate comprising a molecule that homes to prostate tumor tissue, but not to normal prostate, can be used to image a prostate tumor directly.

A homing molecule selective for an organ or tissue can be used to deliver a therapeutic agent to the organ or tissue. Such selective targeting of the agent can increase the effective amount of the agent delivered to the target organ or tissue, while reducing the likelihood the agent will have an adverse effect on other organs or tissues. For example, a lung homing molecule can be used to deliver, to the lung of a cystic fibrosis patient, a gene encoding the cystic fibrosis transmembrane receptor (CFTR), which is defective in cystic fibrosis. Thus, the organ homing molecules of the invention are particularly useful for in vivo gene therapy, since they provide a means to direct a gene to a desired target organ, thereby increasing the likelihood that the target cells will receive the gene and decreasing the likelihood that normal, nontarget, cells will be adversely affected. A lung homing molecule also can be used to direct a therapeutic agent to the lung, thus sparing nontarget organs or tissues from the toxic effects of the agent. For example, in alveolar bacterial pneumonia, a lung homing molecule can be useful for directing an antibiotic to the afflicted region of the lung, thus increasing the effective amount of the drug at the desired site.

Due to the conserved nature of cellular receptors and of ligands that bind a particular receptor, the skilled artisan would recognize that an organ or tissue homing molecule identified using in vivo panning in a mouse or rat also can bind to the corresponding target molecule in the selected organ or tissue of a human or other mammalian species.

Such a homing molecule identified using an experimental animal readily can be examined for the ability to bind to the corresponding organ or tissue in a human subject by demonstrating, for example, that the molecule also can bind selectively in vitro to a sample of the selected organ or tissue obtained from a human subject. Alternatively, primary cells or established cell lines derived from a human organ or tissue can be used to test for the in vitro binding of the homing molecule. Similarly, primary cells or established cell lines that reflect a particular human organ or tissue pathology can be used to test the binding of homing molecules selective for the pathology. Animal models such as primate models of human pathologies are known and also can be used to test for the homing of the molecules using in vivo panning. Thus, routine methods can be used to confirm that an organ or tissue homing molecule identified using in vivo panning in an experimental animal also can bind an organ or tissue-specific target molecule in a human subject. Furthermore, in vitro contacting of a homing molecule with a sample suspected of containing a selected organ, tissue or pathology can identify the presence of the selected organ, tissue or pathology in the sample. Having identified the target molecule by in vivo panning, the artisan would know that it is the true target for an organ homing molecule and, therefore, would know that the target molecule could be used in vitro to identify additional organ homing molecules that likely would be specific for the target molecule in vivo. Such potential organ homing molecules then could be examined by in vivo panning to confirm organ homing ability.

In vivo panning was used to identify peptides expressed by phage that selectively homed to lung, skin, pancreas, retina, prostate, ovary, lymph node, adrenal gland, liver or gut, and to lung containing lung tumors or pancreas containing a pancreatic tumor (Examples II and IV; see, also, Tables 2 to 11). Due to the large size of the phage (300 nm) and the short time the phage were allowed to circulate, it is unlikely that a substantial number of phage would have exited the circulatory system. Indeed, immunohistochemical studies of various organ and tissue homing molecules demonstrated that the molecules primarily home to and bind endothelial cell surface markers of the vasculature. Thus, the invention provides molecules such as peptides that selectively home to the vasculature of a selected organ or tissue.

Phage peptide display libraries were constructed essentially as described by Smith and Scott (supra, 1993; see, also, Koivunen et al., *Biotechnology* 13:265–270 (1995); Koivunen et al., *Meth. Enzymol.* 245:346–369 (1994b), each of which is incorporated herein by reference). In some libraries, at least one codon encoding cysteine also was included in each oligonucleotide so that cyclic peptides could be formed through disulfide linkages (Example I). Upon performing in vivo panning, peptides that selectively home to lung, pancreas, skin, retina, prostate, ovary, lymph node, adrenal gland, liver or gut or to lung containing lung tumors or to pancreas containing a pancreatic tumor were obtained. Thus, the invention provides various organ homing molecules that selectively home to particular organs or tissue.

Remarkably, some organ homing peptides independently were recovered up to four or more times during a round of the in vivo panning procedure (see, for example, Table 1). In addition, various peptides that homed to particular organs or tissues shared conserved amino acid sequence motifs. For example, some lung homing peptides shared a GFE motif; some retina homing peptides shared a RDV motif; and some adrenal gland homing peptides shared a LPR motif (see Tables 2, 6 and 11, respectively). Since it is known, for example, that the tripeptide RGD motif is sufficient for integrin binding (Ruoslahti, *Ann. Rev. Cell Devel. Biol.* 12:697 (1996); Koivunen et al., supra, 1995; WO 95/14714), the results disclosed herein indicate that many ligand/receptor interactions can derive their specificity from recognition motifs as small as tripeptides.

TABLE 1

SUMMARY OF IN VIVO TARGETING OF VARIOUS ORGANS

| ORGAN/MOTIF (SEQ ID NO:) | % OF MOTIF AMONG ALL CLONES | LUNG/BRAIN RATIO |
|---|---|---|
| GUT | | |
| YSGKWGK (9) | 22 | 30 |
| GISALVLS (19) | 11 | nd |
| SRRQPLS (153) | 11 | 2 |
| MSPQLAT (159) | 11 | nd |
| MRRDEQR (172) | | |
| QVRRVPE (155) | | |
| VRRGSPQ (164) | | |
| GGRGSWE (167) | | |
| FRVRGSP (169) | | |
| RVRGPER (165) | | |
| LIVER | | |
| VKSVCRT (12) | 11 | nd |
| WRQNMPL (418) | 6 | nd |
| SRRFVGG (406) | 6 | nd |
| ALERRSL (408) | | |
| ARRGWTL (405) | | |
| PROSTATE | | |
| SMSIARL (21) | 6 | 34 |
| VSFLEYR (22) | 6 | 17 |
| RGRWLAL (279) | 6 | nd |
| ADRENAL GLAND | | |
| LMLPRAD (27) | 11 | 50 |
| LPRYLLS (28) | | |
| R(Y/F)LLAGG (404) | | |
| RYPLAGG (389) | | |
| OVARY | | |
| EVRSRLS (10) | 22 | 3 |
| FFAAVRS (295) | | |
| VRARLMS (301) | | |
| RVGLVAR (11) | 22 | 5 |
| RVRLVNL (294) | | |
| PANCREAS | | |
| SWCEPGWCR (4) | | 20 |
| SKIN | 9 | |
| CVALCREACGEGC (3) | 6 | 7 |
| CSSGCSKNCLEMC (181) | | 2 |
| LUNG | | |
| CTLRDRNC (15) | 10 | 8 |
| CGKRYRNC (20) | 5 | 5 |
| CLRPYLNC (45) | 10 | 6 |
| CGFELETC (2) | 5 | 9 |
| CIGEVEVC (16) | 5 | 6 |
| CKWSRLHSC (65) | 11 | 3 |
| CWRGDRKIC (56) | 8 | 2 |
| CERVVGSSC (59) | 9 | 4 |
| CLAKENVVC (13) | 13 | 2 |
| CTVNEAYKTRMC (75) | 22 | 3 |
| CRLRSYGTLSLC (76) | 5 | 0.4 |
| CRPWHNQAHTEC (82) | 14 | 5 |
| CGFECVRQCPERC (1) | 40 | 60 |

None of the sequences of the disclosed organ homing peptides exhibited significant similarity with known ligands for endothelial cell receptors. While many of the organ homing peptides may be contained within larger peptides or proteins, it is not known whether they are able to impart a homing function onto the larger molecule. Based on the previous finding that RGD mediates integrin binding when present within larger peptides and proteins, one skilled in the art would recognize, however, that such homing peptides and motifs could impart a homing function when located within a larger peptide or protein. However, such naturally occurring endogenous peptides and proteins are not considered to be organ or tissue homing molecules within the invention.

The organ or tissue homing peptide molecules exemplified herein range in size from about 7 to 13 amino acids in length. However, based, for example, on the ability of the RGD integrin binding motif to mediate integrin binding by itself or when present in a large protein, it will be recognized that the organ homing molecules of the invention also can be expected to maintain their homing capability in the context of a significantly longer polypeptide sequence. Thus, an organ homing peptide of the invention can be at least three amino acids, generally at least six amino acids or seven amino acids or more, and can be significantly larger, for example, about 20 to 50 amino acids or 100 amino acids or more.

The invention provides lung homing peptides such as CGFECVRQCPERC (SEQ ID NO: 1) and CGFELETC (SEQ ID NO: 2), which share a GFE motif; CTLRDRNC (SEQ ID NO: 15); and CIGEVEVC (SEQ ID NO: 16; see Table 1), which contains an EVE motif that is similar to the ELE motif present in CGFELETC (SEQ ID NO: 2). The exemplified lung homing peptides were identified by injection of a $CX_3CX_3CX_3C$, (SEQ ID NO: 25), $CX_7C$ (SEQ ID NO: 24) or $CX_6C$ (SEQ ID NO: 26) cyclic library into mice (Example II). The lung homing peptides CGFECVRQCPERC (SEQ ID NO: 1) and CGFELETC (SEQ ID NO: 2) exhibited a 60-fold and 9-fold enrichment, respectively, as compared to unselected phage, with few phage detected in kidney or brain (Example II; see, also, FIGS. 1 and 2 and Table 1). In addition, the lung homing peptides CTLRDRNC (SEQ ID NO: 15) and CIGEVEVC (SEQ ID NO: 16) exhibited a 8-fold and 6-fold enrichment, respectively, over unselected phage (Table 1). Coinjection of a glutathione-S-transferase-(GST-)CGFECVRQCPERC (SEQ ID NO: 1) fusion peptide with phage expressing the cognate CGFECVRQCPERC (SEQ ID NO: 1) peptide inhibited homing by 70%, and coinjection of GST-CGFELETC (SEQ ID NO: 2) with phage expressing (SEQ ID NO: 2) inhibited lung homing by 30% (FIG. 3). Immunohistochemical staining of lung following administration of phage displaying a lung homing peptide to mice revealed staining within the alveolar capillaries. No apparent preference for homing of the phage to any particular region of the lung was observed; however, no staining was observed in bronchioles luminal walls or some larger blood vessels (Example III), or in many other tissues analyzed. These results indicate that in vivo panning can be used to identify and analyze endothelial cell specificities within lung, thus providing a means to differentially target lung.

The invention also provides skin homing peptides such as CVALCREACGEGC (SEQ ID NO: 3; Table 5), which were identified by injection of a $CX_3CX_3CX_3C$ (SEQ ID NO: 25) cyclic library into mice (Example II). The skin homing peptide sequence CVALCREACGEGC (SEQ ID NO: 3) exhibited a 7-fold selectivity for skin over unselected phage and over background in brain and kidney (FIG. 2; see, also, Table 1). Coinjection of GST-CVALCREACGEGC (SEQ ID NO: 3) with phage expressing CVALCREACGEGC (SEQ ID NO: 3) inhibited homing to skin by 55%, whereas coinjection with GST, alone, had no effect on homing (see FIG. 3B). Immunohistochemical staining of skin following administration of phage displaying a skin homing peptide revealed that staining was localized to the hypodermis; no staining was observed in the dermis (Example III).

The invention further provides pancreas homing peptides such as SWCEPGWCR (SEQ ID NO: 4; Table 3). The exemplified pancreas homing molecules were identified by injection of a $CX_7C$ (SEQ ID NO: 24) or $X_2CX_4CX$ (SEQ ID NO: 23) cyclic library into mice (Example II). The pancreas homing peptide SWCEPGWCR (SEQ ID NO: 4) exhibited a 20-fold selectivity for pancreas over unselected phage and over brain (Table 1; FIG. 2). However, coinjection of GST-SWCEPGWCR (SEQ ID NO: 4) did not inhibit SWCEPGWCR (SEQ ID NO: 4) pancreas homing, presumably due to a conformational effect of GST on the pancreas homing peptide. Immunohistochemical staining of pancreas following administration of phage displaying a pancreas homing peptide revealed that staining was localized to the capillaries as well as larger blood vessels of the exocrine pancreas; no significant staining was observed in the endocrine vasculature (Example III). This result demonstrates that histologically and physiologically distinguishable regions within a particular organ can express unique target molecules, which provide a target for an organ homing molecule of the invention. Accordingly, the organ homing molecules of the invention provide a means to differentially targeted specific regions of a selected organ or tissue.

Retina homing peptides such as CSCFRDVCC (SEQ ID NO: 5) and CRDVVSVIC (SEQ ID NO: 6) also are provided (see Table 6). The exemplified retina homing molecules were identified by injection of a $CX_7C$ (SEQ ID NO: 24) cyclic library into rats (Example II). The retina homing peptides CSCFRDVCC (SEQ ID NO: 5) and CRDVVSVIC (SEQ ID NO: 6), when injected individually with a control fdAMPLAY88 phage, exhibited a 3-fold and 2-fold enrichment, respectively, in retina (Example II). However, immunohistochemical staining revealed an absence of retina staining, presumably due to a relatively modest accumulation of the retina homing phage in the target tissue.

The invention also provides prostate homing peptides such as SMSIARL (SEQ ID NO: 21) and VSFLEYR (SEQ ID NO: 22), which were identified by injection of an $X_7$ (SEQ ID NO: 29) library into mice (Table 7). The peptides were isolated by the regular method. The prostate homing peptides SMSIARL (SEQ ID NO: 21) and VSFLEYR (SEQ ID NO: 22) exhibited a 34-fold and 17-fold enrichment, respectively, in homing to prostate as compared to brain (Table 1).

Also provided are ovary homing peptides such as RVGLVAR (SEQ ID NO: 11) and EVRSRLS (SEQ ID NO: 10), which were identified by injection of an $X_7$ (SEQ ID NO: 29) library into mice (Table 8). The peptides were isolated by the regular method. The ovary homing peptides RVGLVAR (SEQ ID NO: 11) and EVRSRLS (SEQ ID NO: 10) each comprised 22% of 40 clones sequenced and exhibited a 5-fold and a 3-fold enrichment, respectively, in ovary as compared to brain (Table 1).

The invention also provides adrenal gland homing peptides such as LMLPRAD (SEQ ID NO: 27) and LPRYLLS (SEQ ID NO: 28), which share a LPR motif (see Table 11), or the peptides R(Y/F)LLAGG (SEQ ID NO: 404) and RYPLAGG (SEQ ID NO: 389), which share the motif LAGG (SEQ ID NO: 430; see Table 10). The exemplified adrenal gland homing peptides were identified by injection of an $X_7$ (SEQ ID NO: 29) library into mice. The peptides were isolated by the regular method. The adrenal gland homing peptide LMLPRAD (SEQ ID NO: 27) exhibited a 50-fold enrichment in adrenal gland as compared to brain (Table 1).

Also provided are liver homing peptides. Such peptides were identified by injection of an $X_7$ (SEQ ID NO: 29) library into mice. The peptides were isolated by the regular method (see Example II, Table 1, and Table 11, below).

In addition, lymph node homing peptides, such as AGCSVTVCG (SEQ ID NO: 315) are provided (Table 9, below). Such peptides were identified by injection of an $X_2CX_4CX$ (SEQ ID NO: 23) library into mice. The peptides were isolated by the regular method.

The invention also provides gut homing peptides such as YSGKWGK (SEQ ID NO: 9) and YSGKWGW (SEQ ID NO: 156), which were identified by injection of an $X_7$ (SEQ ID NO: 29) library into mice (Tables 1 and 4) and differ only in the last amino acid position. The peptides were isolated by the regular method. The gut homing peptide YSGKWGK (SEQ ID NO: 9) was present in 22% of 40 clones sequenced and was enriched 30-fold in gut as compared to brain (Table 1). In addition, gut homing peptides such as QVRRVPE (SEQ ID NO: 155) and VRRGSPQ (SEQ ID NO: 164), which share a VRR motif, were identified, as were the peptides VRRGSPQ (SEQ ID NO: 164), GGRGSWE (SEQ ID NO: 167) and FRVRGSP (SEQ ID NO: 169), which share an RGS motif.

The organ homing molecules of the invention are particularly useful as conjugates, which comprise the organ homing molecule linked to a moiety. Thus, a lung, skin, pancreas, retina, prostate, ovary, lymph node, adrenal gland, liver or gut homing molecule of the invention can be linked to a moiety, such conjugates being useful for directing the moiety to the particular selected organ.

As used herein, the term "moiety" is used broadly to mean a physical, chemical, or biological material that is linked to an organ or tissue homing molecule. Generally, a moiety linked to an organ homing molecule imparts a biologically useful function to the homing molecule. A moiety can consist of any natural or nonnatural material for example, peptide or polypeptide sequences, organic or inorganic molecules or compositions, nucleic acid molecules, carbohydrates, lipids or combinations thereof.

A moiety can be a physical, chemical or biological material such as a virus, viral gene therapy vector, cell, liposome, microcapsule, micropump or other chambered microdevice, which can be used, for example, as a drug delivery system. Generally, such microdevices should be biologically inert and, if desired, biodegradable or excretable. Various moieties, including microcapsules, which can contain an agent, and methods for linking a moiety or chambered microdevice to an organic molecule of the invention are well known in the art and commercially available (see, for example, "Remington's Pharmaceutical Sciences" 18th ed. (Mack Publishing Co. 1990), chapters 89–91; Harlow and Lane, *Antibodies: A laboratory manual* (Cold Spring Harbor Laboratory Press 1988), each of which is incorporated herein by reference; see, also, Hermanson, supra, 1996). Additional examples of moieties are known to those skilled in the art and are intended to be included within the meaning of the term so long as they possess a biologically useful function when linked to the homing molecules of the invention.

Linking of a moiety to an organ homing molecule for the purpose of directing the moiety to the selected organ or tissue was demonstrated by the linking of a brain homing peptide to a red blood cell (RBC), wherein the peptide directed homing of the RBC to the brain (U.S. Pat. No. 5,622,699, supra, 1997). These results indicate that an organ or tissue homing molecule of the invention can be linked to another moiety in order to direct the moiety to a selected organ or tissue. For example, a liver homing molecule ml or a lung homing molecule can be linked to a nucleic acid encoding the CFTR gene and upon administration to a subject, expression of CFTR is targeted to the liver or to the lung, respectively. Similarly, a lung homing molecule can be linked to a protease inhibitor such that, upon administration of the conjugate comprising the lung homing molecule and the protease inhibitor to a subject, the protease inhibitor is targeted to the lung. Such a conjugate can be useful, for example, for treating a subject suffering from emphysema, which is characterized by excessive protease production in the lungs and autodigestion of the organ.

An organ and tissue homing molecule of the invention can be useful for directing to a selected organ or tissue a therapeutic agent, diagnostic agent or imaging agent, a tag or insoluble support, a liposome or a microcapsule comprising, for example, a permeable or semipermeable membrane, wherein an agent such as a drug to be delivered to a selected organ or tissue is contained within the liposome or microcapsule. These and other moieties known in the art can be used in a conjugate of the invention, and in method of the invention, as disclosed herein.

In one embodiment, a moiety can be a detectable agent such as a radionuclide or an imaging agent, which allows detection or visualization of the selected organ or tissue. Thus, the invention provides a conjugate comprising a lung, skin, pancreas, retina, prostate, ovary, lymph node, adrenal gland, liver or gut homing molecule, linked to a detectable agent. The type of detectable agent selected will depend upon the application. For example, for an in vivo diagnostic imaging study of the lung in a subject, a lung homing molecule can be linked to an agent that, upon administration to the subject, is detectable external to the subject. For detection of such internal organs or tissues, for example, the prostate, a gamma ray emitting radionuclide such as indium-113, indium-115 or technetium-99 can be linked to a prostate homing molecule and, following administration to a subject, can be visualized using a solid scintillation detector. Alternatively, for organs or tissues at or near the external surface of a subject, for example, retina, a fluorescein-labeled retina homing molecule can be used such that the endothelial structure of the retina can be visualized using an opthalamoscope and the appropriate optical system.

Molecules that selectively home to a pathological lesion in an organ or tissue similarly can be linked to an appropriate detectable agent such that the size and distribution of the lesion can be visualized. For example, where an organ or tissue homing molecule homes to a normal organ or tissue, but not to a pathological lesion in the organ or tissue, the presence of the pathological lesion can be detected by identifying an abnormal or atypical image of the organ or tissue, for example, the absence of the detectable agent in the region of the lesion.

A detectable agent also can be an agent that facilitates detection in vitro. For example, a conjugate comprising a homing molecule linked to an enzyme, which produces a visible signal when an appropriate substrate is present, can detect the presence of an organ or tissue to which the homing molecule is directed. Such a conjugate, which can comprise, for example, alkaline phosphatase or luciferase or the like, can be useful in a method such as immunohistochemistry. Such a conjugate also can be used to detect the presence of a target molecule, to which the organ homing molecule binds, in a sample, for example, during purification of the target molecule.

In another embodiment, a moiety can be a therapeutic agent. Thus, the invention provides a conjugate comprising a lung, skin, pancreas, retina, prostate, ovary, lymph node, adrenal gland, liver or gut homing molecule linked to a therapeutic agent.

A therapeutic agent can be any biologically useful agent that, when linked to an organ homing molecule of the invention, exerts its function at the site of the selected organ or tissue. For example, a therapeutic agent can be a small organic molecule that, upon binding to a target cell due to the linked organ homing molecule, is internalized by the cell where it can effect its function. A therapeutic agent can be a nucleic acid molecule that encodes a protein involved in stimulating or inhibiting cell survival, cell proliferation or cell death, as desired, in the selected organ or tissue. For example, a nucleic acid molecule encoding a protein such as Bcl-2, which inhibits apoptosis, can be used to promote cell survival, whereas a nucleic acid molecule encoding a protein such as Bax, which stimulates apoptosis, can be used to promote cell death of a target cell.

A particularly useful therapeutic agent that stimulates cell death is ricin, which, when linked to an organ homing molecule of the invention, can be useful for treating a hyperproliferative disorder, for example, cancer. A conjugate comprising an organ homing molecule of the invention and an antibiotic, such as ampicillin or an antiviral agent such as ribavirin, for example, can be useful for treating a bacterial or viral infection in a selected organ or tissue.

A therapeutic agent also can inhibit or promote the production or activity of a biological molecule, the expression or deficiency of which is associated with the pathology. Thus, a protease inhibitor can be a therapeutic agent that, when linked to an organ homing molecule, can inhibit protease activity at the selected organ or tissue, for example, the pancreas. A gene or functional equivalent thereof such as a cDNA, which can replenish or restore production of a protein in a selected organ or tissue, also can be a therapeutic agent useful for ameliorating the severity of a pathology. A therapeutic agent also can be an antisense nucleic acid molecule, the expression of which inhibits production of a deleterious protein, or can be a nucleic acid molecule encoding a dominant negative protein or a fragment thereof, which can inhibit the activity of a deleterious protein.

In another embodiment, the invention provides a conjugate comprising a lung, skin, pancreas, retina, prostate, ovary, lymph node, adrenal gland, liver or gut homing molecule linked to a tag. A tag can be, for example, an insoluble support such as a chromatography matrix, or a molecule such as biotin, hemagglutinin antigen, polyhistidine, T7 or other molecules known in the art. Such a conjugate comprising a tag can be useful to isolate a target molecule, to which the organ homing molecule binds.

When administered to a subject, a conjugate comprising an organ homing molecule and a moiety is administered as a pharmaceutical composition containing, for example, the conjugate and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil or injectable organic esters.

A pharmaceutically acceptable carrier can contain physiologically acceptable compounds that act, for example, to stabilize or to increase the absorption of the complex. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the composition. The pharmaceutical composition also can contain an agent such as a cancer therapeutic agent or other therapeutic agent as desired.

One skilled in the art would know that a pharmaceutical composition containing an organ homing molecule can be administered to a subject by various routes including, for example, orally or parenterally, such as intravenously. The composition can be administered by injection or by intubation. The pharmaceutical composition also can be an organ homing molecule linked to a moiety such as a liposome or other polymer matrix, which can have incorporated therein, for example, a drug that promotes or inhibits cell death (Gregoriadis, *Liposome Technology*, Vol. 1 (CRC Press, Boca Raton, Fla. 1984), which is incorporated herein by reference). Liposomes, for example, which consist of phospholipids or other lipids, are nontoxic, physiologically acceptable and metabolizable carriers that are relatively simple to make and administer.

In performing a diagnostic or therapeutic method as disclosed herein, an effective amount of a conjugate comprising an organ homing molecule must be administered to the subject. An "effective amount" is the amount of the conjugate that produces a desired effect. An effective amount will depend, for example, on the moiety linked to the organ homing molecule and on the intended use. For example, a lesser amount of a radiolabeled homing molecule can be required for imaging as compared to the amount of the radiolabeled molecule administered for therapeutic purposes, where cell killing is desired. An effective amount of a particular conjugate for a specific purpose can be determined using methods well known to those in the art.

The route of administration of an organ molecule will depend, in part, on the chemical structure of the organ homing molecule. Peptides, for example, are not particularly useful when administered orally because they can be degraded in the digestive tract. However, methods for chemically modifying peptides to render them less susceptible to degradation by endogenous proteases or more absorbable through the alimentary tract are well known (see, for example, Blondelle et al., supra, 1995; Ecker and Crooke, supra, 1995; Goodman and Ro, supra, 1995). Such methods can be performed on peptides that home to a selected organ or tissue. In addition, methods for preparing libraries of peptide analogs such as peptides containing D-amino acids; peptidomimetics consisting of organic molecules that mimic the structure of a peptide; or peptoids such as vinylogous peptides, have been previously described above and can be used to identify homing molecules suitable for oral administration to a subject.

The invention provides methods of identifying a selected organ or tissue by administering to a subject a conjugate comprising a lung, skin, pancreas, retina, prostate, ovary, lymph node, adrenal gland, liver or gut and a detectable agent. A conjugate comprising an organ homing molecule of the invention linked to a detectable moiety conjugate can be administered to a subject and used to identify or visualize a selected organ or tissue. The ability to visualize an organ, particularly an internal organ, provides a means diagnose a pathology of the selected organ or tissue. For example, a prostate homing molecule linked to indium-113 can be administered to a subject in order to image the prostate. Such a method can be particularly valuable because methods for imaging the prostate are limited. The presence of a prostate pathology can be revealed by detecting that a region of the prostate does not contain the conjugate, thus indicating an abnormality in circulation to the region, or by detecting that the prostate is abnormally enlarged or lacking its normal boundaries. For organs or tissues such as retina, which can be visualized directly using an ophthalmoscope, a conjugate comprising a retina homing molecule linked to fluorescein can be administered to a subject and used to examine the vascular integrity and circulation in the retina. The absence of a normal or typical pattern of retinal image can indicate the presence of a retinal pathology in the region. For example, an abnormal retinal pattern can reflect vascular changes indicative of a hyperproliferative or degenerative pathology.

In principle, an organ homing molecule of the invention can have an inherent biological property, such that administration of the molecule provides direct biological effect. For example, an organ homing molecule can be sufficiently similar to a naturally occurring ligand for the target molecule that the organ homing molecule mimics the activity of the natural ligand. Such an organ homing molecule can be useful as a therapeutic agent having the activity of the natural ligand. For example, where the organ homing molecule mimics the activity of a growth factor that binds a receptor expressed by the selected organ or tissue, such as a skin homing molecule that mimics the activity of epidermal growth factor, administration of the organ homing molecule can result in cell proliferation in the organ or tissue. Such inherent biological activity of an organ homing molecule of the invention can be identified by contacting the cells of the selected organ or tissue with the homing molecule and examining the cells for evidence of a biological effect, for example, cell proliferation or, where the inherent activity is a toxic effect, cell death.

In addition, an organ homing molecule of the invention can have an inherent activity of binding a particular target molecule such that a corresponding ligand cannot bind the receptor. It is known, for example, that various types of cancer cells metastasize to specific organs or tissues, indicating that the cancer cells express a ligand that binds a target molecule in the organ to which it metastasizes. Thus, administration of a lung homing molecule, for example, to a subject having a tumor that metastasizes to lung, can provide a means to prevent the potentially metastatic cancer cell from becoming established in the lung. In general, however, the organ homing molecules of the invention are particularly useful for targeting a moiety to a selected organ or tissue, particularly to lung, skin, pancreas, retina, prostate, ovary, lymph node, adrenal gland, liver or gut. Thus, the invention provides methods of treating a pathology in a selected organ or tissue by administering to a subject having the pathology a conjugate comprising an organ homing molecule of the invention linked to a therapeutic agent.

Specific disorders of the lung, for example, can be treated by administering to a subject a conjugate comprising a lung homing molecule linked to a therapeutic agent. Since a lung homing molecule of the invention can localize to the capillaries and alveoli of the lung, disorders associated with these regions are especially amenable to treatment with a conjugate comprising the lung homing molecule. For example, bacterial pneumonia often originates in the alveoli and capillaries of the lung (Rubin and Farber, *Pathology* 2nd ed., (Lippincott Co., 1994)). Thus, a lung homing molecule conjugated to a suitable antibiotic can be administered to a subject to treat the pneumonia. Similarly, cystic fibrosis causes pathological lesions in the lung due to a defect in the CFTR. Thus, administration of a lung homing molecule conjugated to a nucleic acid molecule encoding the CFTR provides a means for directing the nucleic acid molecule to the lung as an in vivo gene therapy treatment method.

The invention also provides methods of treating a pathology of the skin by administering to a subject having the pathology a conjugate comprising a skin homing molecule and a therapeutic agent. For example, a burn victim can be administered a conjugate comprising a skin homing molecule linked to epithelial growth factor or platelet derived growth factor such that the growth factor is localized to the skin where it can accelerate regeneration or repair of the epithelium and underlying dermis. Furthermore, a method of the invention can be useful for treating skin pathologies caused by bacterial infections, particularly infections that spread through the hypodermis and dermis or that are localized in these regions, by administering to a subject a conjugate comprising a skin homing molecule linked to an antibiotic.

The invention also provides methods of treating a pathology of the pancreas by administering to a subject having the pathology a conjugate comprising a pancreas homing molecule linked to a therapeutic agent. In particular, since a pancreas homing molecule of the invention can localize to the exocrine pancreas, a pathology associated with the exocrine pancreas can be treated and, in some cases, may not adversely affect the endocrine pancreas. A method of the invention can be particularly useful to treat acute pancreatitis, which is an inflammatory condition of the exocrine pancreas caused by secreted proteases damaging the organ. A conjugate comprising a pancreas homing molecule linked to a protease inhibitor can be used to inhibit the protease mediated destruction of the tissue, thus reducing the severity of the pathology. Appropriate protease inhibitors useful in such a conjugate are those that inhibit enzymes associated with pancreatitis, including, for example, inhibitors of trypsin, chymotrypsin, elastase, carboxypeptidase and pancreatic lipase. A method of the invention also can be used to treat a subject having a pancreatic cancer, for example, ductal adenocarcinoma, by administering to the subject a conjugate comprising a therapeutic agent linked to a molecule that homes to pancreas.

The methods of the invention also can be used to treat a pathology of the eye, particularly the retina, by administering to a subject having the pathology a conjugate comprising a retina homing molecule linked to a therapeutic agent. For example, proliferative retinopathy is associated with neovascularization of the retina in response to retinal ischemia due, for example, to diabetes. Thus, administration of a conjugate comprising a retina homing molecule linked to a gene that stimulates apoptosis, for example, Bax, can be used to treat the proliferative retinopathy. Similarly, methods of the invention can be used to diagnose or treat prostate, ovary, lymph node, adrenal gland, liver, or gut pathology using the appropriate organ or tissue homing molecules disclosed herein either alone, or linked to a desired moiety.

An organ or tissue homing molecule is useful, for example, for targeting a therapeutic or detectable agent to the selected organ or tissue. In addition, an organ or tissue homing molecule can be used to identify the presence of a target molecule in a sample. As used herein, the term "sample" is used in its broadest sense to mean a cell, tissue, organ or portion thereof that is isolated from the body. A sample can be, for example, a histologic section or a specimen obtained by biopsy or cells that are placed in or adapted to tissue culture. If desired, a sample can be processed, for example, by homogenization, which can be an initial step for isolating the target molecule to which an organ or tissue homing molecule binds.

An organ homing molecule obtained as disclosed herein can be useful for identifying the presence of a target molecule, particularly a cell surface protein, that is recognized by the homing molecule, or for substantially isolating the target molecule. Thus, the invention provides methods of identifying target molecules that selectively bind a lung homing molecule, a skin homing molecule, a pancreas homing molecule, a retina homing molecule, a prostate homing molecule, an ovary homing molecule, a lymph node homing molecule, an adrenal gland homing molecule, a liver homing molecule or a gut homing molecule. Such a method comprises contacting a sample of the selected organ or tissue, for example, prostate, with a prostate homing molecule, and detecting selective binding of a component of a sample, wherein such binding identifies the presence of a target molecule.

An organ or tissue homing molecule such as a prostate homing peptide can be linked to a tag, for example, a solid support such as a chromatography matrix. The immobilized organ homing molecule then can be used for affinity chromatography by passing an appropriately processed sample of prostate tissue over a column containing the matrix under conditions that allow specific binding of the prostate homing molecule to the particular target molecule (see, for example, Deutshcer, Meth. Enzymol., Guide to Protein Purification (Academic Press, Inc., ed. M. P. Deutscher, 1990), Vol. 182, which is incorporated herein by reference; see, for example, pages 357–379). Unbound and nonspecifically bound material can be removed and the target molecule, which forms a complex with the prostate homing molecule, can be eluted from the column and collected in a substantially isolated form. The substantially isolated prostate target molecule then can be characterized using well known methods. An organ or tissue homing molecule also can be linked to a detectable agent such as a radionuclide, a fluorescent molecule, an enzyme or a labeled biotin tag and can be used, for example, to screen a sample in order to detect the presence of the target molecule or to follow the target molecule during its isolation.

As an alternative to using an organ or tissue sample to identify a target molecule of the selected organ or tissue, extracts of cultured cells derived from the selected organ or tissue, or extracts of cultured endothelial cells can be used as the starting material. Selection of cells containing the target molecule can be determined by using binding and cell attachment assays (see Barry et al., Nature Med. 2:299–305 1996), which is incorporated herein by reference). Those cells containing the target molecule can be used to prepare extracts for the isolation and identification of a target molecule, as described above.

Upon identifying an appropriate cell line expressing the target molecule, the target molecule can be labeled by growing the cells in medium containing radiolabeled amino acids. The radiolabeled amino acids are incorporated into the target molecule, thus facilitating its identification during purification. Labeled cells then can be extracted with octylglucoside and the extract can be fractionated by affinity chromatography using a pancreas homing molecule coupled to a matrix such as Sepharose. Extracts prepared, for example, from human umbilical vein endothelial cells can be used as a control. The purified target molecule then can be microsequenced and antibodies can be prepared. If desired, oligonucleotide probes can be prepared and used to isolate cDNA clones encoding the target receptor. Alternatively, an anti-receptor antibody can be used to isolate a cDNA clone from an expression library (see Argraves et al., J. Cell Biol. 105:1183–1190 (1987), which is incorporated herein by reference).

In addition to biochemically isolating a target molecule, a nucleic acid encoding the target molecule can be isolated by using, for example, a pancreas homing molecule as a chemical probe to screen a pancreatic cDNA expression library for clones that express the target molecule. For example, bacteria expressing a pancreatic cDNA library can be attached to a membrane, lysed, and screened with a pancreas homing molecule conjugated, for example, to an enzyme that produces a calorimetric or fluorescent signal. Bacterial clones expressing a target molecule are identified and the cDNA encoding the target molecule can be isolated. Additionally, a mammalian cell expression cloning system such as the COS cell system can be used to identify a target molecule. For example, a cDNA library can be prepared using mRNA from primary pancreas cells which can be cloned into an expression vector. Cells expressing a cDNA encoding the target molecule then can be selected using the pancreas homing peptide as a probe, for example, by panning of cell clones against pancreas homing peptide attached to a plate. Alternatively, phage can be used to display the pancreas homing peptide and can be attached to magnetic beads coated, for example, with anti-M13 antibodies (Pharmacia). Cells expressing the target molecule that bind to the pancreas homing peptide then can be recovered and the plasmids encoding the receptor can be isolated. The recovered plasmid preparations can be divided into pools and examined in COS cell transfections. The procedure can be repeated until single plasmids are obtained that enable the COS cells to bind the pancreas homing peptide.

The present invention also provides a method of identifying a MDP-binding homing molecule that selectively homes to lung endothelium. The method includes the steps of contacting membrane dipeptidase (MDP) with one or more molecules; and determining specific binding of a molecule to the MDP, where the presence of specific binding identifies the molecule as a MDP-binding homing molecule that selectively homes to lung endothelium. In a method of the invention, the membrane dipeptidase can be substantially purified and can be, for example, immobilized to a support. The membrane dipeptidase can be any mammalian MDP, for example, human MDP having SEQ ID NO: 448.

As disclosed herein, the CGFECVRQCPERC (SEQ ID NO: 1) peptide can selectively bind to mouse lung vasculature after intravenous injection (Example IIA). Furthermore, as disclosed in Example IVB, a 55 kDa lung cell surface protein that selectively binds GFE-1 (CGFECVRQCPERC; SEQ ID NO: 1) was isolated from rat lung extracts using affinity chromatography. Tryptic digestion and sequencing by mass spectrometry revealed that two peptides derived from the 55 kDa protein were completely identical to portions of rat membrane dipeptidase (EC 3.4.13.19). Further experimentation demonstrated that GFE-1 (SEQ ID NO: 1) affinity purified fractions of rat lung cell extracts have membrane dipeptidase activity, as indicated by the time-dependent conversion of the specific MDP substrate Gly-D-Phe to D-Phe (Example IVC and FIG. 5). Furthermore, binding of GFE-1 phage (CGFECVRQCPERC; SEQ ID NO: 1) and, to a lesser extent, GFE-2 phage (CGFELETC; SEQ ID NO: 2) to COS cells transfected with membrane dipeptidase was significantly higher than the binding of phage bearing an unrelated peptide sequence (Example IVD and FIG. 6B), indicating that membrane dipeptidase is the GFE-1 (SEQ ID NO: 1) receptor.

Thus, as disclosed herein, the lung metalloprotease, membrane dipeptidase, serves as the receptor for the selective homing of molecules to lung endothelium. An exemplary class of molecules that selectively home to lung endothelium by targeting membrane dipeptidase is the class of peptides bearing a GFE motif, for example, CGFECVRQCPERC (SEQ ID NO: 1).

Membrane dipeptidase, also known as renal dipeptidase, microsomal dipeptidase, dehydropeptidase-1, or MDP and currently classified as EC 3.4.13.19 (previously EC 3.4.13.11), is a plasma membrane glycosyl phosphatidylinositol-anchored glycoprotein (Keynan et al., in Hooper (Ed.) *Zinc Metalloproteases in Health and Disease* Taylor and Francis, London pages 285–309 (1996), which is incorporated herein by reference). This zinc metalloprotease, which is expressed mainly in lung and kidney brush border, is involved in vivo in renal metabolism of glutathione and in pulmonary metabolism of peptidyl leukotrienes. In addition, MDP is the only known example of a mammalian β-lactamase. MDP forms a disulfide-linked homodimer, with the molecular weight of the monomer ranging from about 48 to 59 kDa depending on the species of origin (Keynan et al., *Biochem.* 35:12511–12517 (1996), which is herein incorporated by reference; see, also, Example IVB).

Membrane dipeptidase expression has been detected in several tissues although it is expressed mainly in lung and kidney. There have been reports of low levels of MDP activity in total extracts from liver, spleen, small intestine and brain, while others have found no detectable activity in these organs. In the mouse, four distinct MDP mRNAs are present, and they are differentially expressed in several organs (Habib et al., *J. Biol. Chem.* 271:16273–16280 (1996)). Organ-specific differences in the nature and extent of pig MDP N-linked glycosylation also have been reported (Hooper et al., *Biochem. J.* 324:151–157 (1997)).

In the kidney, MDP expression is restricted to epithelial cells in the brush border region of the proximal tubules. In the lung, MDP expression has been detected in many cell types including endothelial cells as well as epithelial cells of the conducting airways, alveolar ducts, capillaries, and the basement membrane of alveoli and terminal bronchioles (Habib et al., supra, 1996); Inamura et al., *Prostaglandins Leukotrienes and Essential Fatty Acids* 50:85–92 (1994)). MDP expression also has been observed on endothelial cells of submucosal microvessels in the human trachea (Yamaya et al., *Resp. Physiol.* 111:101–109 (1998)). The level of MDP activity is highest in lung (Hirota et al., *Eur. J. Biochem.* 160:521–525 (1986); Habib et al., *Proc. Natl. Acad. Sci. USA* 95:4859–4863 (1998)). This expression pattern correlates with the strong lung homing of molecules such as GFE-1 (SEQ ID NO: 1).

As used herein, the term "membrane dipeptidase" is synonymous with "MDP" and refers to the enzyme currently classified as EC 3.4.13.19 (previously EC 3.4.13.11) and also known as renal or microsomal dipeptidase or dehydropeptidase-1. The term membrane dipeptidase encompasses any mammalian membrane dipeptidase, for example, the human, pig, mouse, rat and rabbit homologs having the amino acid sequences shown as SEQ ID NOS: 448 to 452 in FIG. 9 as well as related polypeptides having substantial amino acid sequence similarity to one of these polypeptides. Such related polypeptides will exhibit greater sequence similarity to SEQ ID NO: 448, 449, 450, 451 or 452 than to other zinc metalloproteases or peptidases such as dipeptidyl peptidase IV and include alternatively spliced forms of MDP and isotype variants of the amino acid sequences shown in FIG. 9. Thus, the term MDP encompasses homologous polypeptides obtained from different mammalian species as well as other variants and related polypeptides that generally have amino acid identities of greater than about 65%, preferably greater than about 70% and more preferably greater than about 80% or 90% with SEQ ID NO: 448, 449, 450, 451 or 452. A method of the invention preferably uses human membrane dipeptidase (SEQ ID NO: 448).

The term "substantially purified," as used herein in reference to a membrane dipeptidase polypeptide, means that the polypeptide is in a form that is relatively free from contaminating lipids, nucleic acids, unrelated polypeptides and other cellular material normally associated with membrane dipeptidase in a cell.

The methods of the invention for identifying a MDP-binding homing molecule can be practiced in vivo or in vitro, and membrane dipeptidase can be obtained from a number of sources. Sources of membrane dipeptidase include whole cells or cell extracts containing endogenous or exogenous MDP. Additional sources of MDP include partially purified cell extracts; biochemically purified enzyme, for example, affinity purified MDP; recombinant polypeptides; and transfected cell lines.

Affinity chromatography can be particularly useful for purifying or partially purifying membrane dipeptidase for use in a method of the invention. For example, membrane dipeptidase can be purified from lung cell extracts by affinity chromatography using immobilized GFE-1 peptide (SEQ ID NO: 1) as described for murine and rat membrane dipeptidase in Example IVC. Similarly, membrane dipeptidase can be obtained by affinity chromatography using other immobilized ligands such as cilastatin. For example, membrane dipeptidase can be efficiently purified in two steps, through selective release of MDP by bacterial phosphatidyl inositol-specific phospholipase C (PI-PLC) coupled with cilastatin-Sepharose affinity chromatography as described in Littlewood et al., *Biochem. J.* 257:361–367 (1989); and Campbell et al., *J. Biol. Chem.* 259:14586–14590 (1984), each of which is incorporated herein by reference.

Recombinant membrane dipeptidase also can be useful in a method of the invention. The amino acid and nucleic acid sequences of a variety of MDP homologs are known in the art. Nucleic acid sequences encoding the membrane dipeptidase polypeptides shown in FIG. 9 can be obtained, for example, from databases such as GenBank or from the literature (see, for example, GenBank Accession Numbers D13139 and 285150; Adachi et al., *J. Biol. Chem.* 265:3992–3995 (1990); Rached et al., 1990; Keynan et al., *FEBS Letts.* 349:50–54 (1994); Satoh et al., *Biochim. Biophys. Acta* 1163:234–242 (1993); Adachi et al., *Biochim. Biophys. Acta* 1132:311–314 (1992); An et al., *Biochim. Biophys. Acta* 1226:337–340 (1994); and Igarashi and Karniski, *Biochem. J.* 280:71–78 (1991), each of which is incorporated herein by reference). Novel membrane dipeptidase cDNAs can be isolated from additional mammalian species with a nucleotide sequence as a probe or primer using methods well known in the art of molecular biology (Innis et al. (Ed.), *PCR Protocols*, San Diego: Academic Press, Inc. (1990); Erlich, supra, 1989; Sambrook et al., supra, 1989, each of which is incorporated herein by reference). One skilled in the art knows a variety of methods for expression of MDP encoding nucleic acids and subsequent isolation of recombinant MDP polypeptide.

In the methods of the invention for identifying a MDP-binding homing molecule that selectively homes to lung endothelium, specific binding of a molecule to MDP identifies the molecule as a MDP-binding homing molecule that selectively homes to lung endothelium. The term "specific binding," as used herein in reference to a molecule and MDP, means that the molecule has an affinity for MDP that is measurably different from a non-specific interaction. Specific binding can be measured, for example, by determining binding of a molecule compared to binding of a control molecule, which generally is a molecule of similar structure that does not have binding activity, for example, a peptide of similar size that lacks a GFE motif. In this case, specific binding is indicated if the molecule has measurably higher affinity for membrane dipeptidase than the control molecule. Specificity of binding also can be determined, for example, by competition with a control molecule that is known to bind to MDP, for example, a peptide containing the GFE motif.

The term specific binding, as used herein, includes both low and high affinity specific binding. Specific binding can be exhibited, for example, by a low affinity MDP-binding homing molecule having a Kd for membrane dipeptidase of about $10^{-4}$ M to about $10^{-7}$ M. Specific binding also can be exhibited by a high affinity MDP-binding homing molecule, for example, a MDP-binding homing molecule having a Kd for membrane dipeptidase of at least about $10^{-7}$ M, at least about $10^{-8}$ M, at least about $10^{-9}$ M, at least about $10^{-10}$ M, or at least about $10^{-11}$ M or $10^{-12}$ M or greater. A MDP-binding homing peptide including the sequence $X_1$-G-F-E-$X_2$ (SEQ ID NO: 17), where $X_1$ and $X_2$ each is 1 to 10 independently selected amino acids, can have, for example, a Kd for membrane dipeptidase of about $2 \times 10^{-5}$ M to $10^{-7}$ M, for example, a Kd of about $10^{-6}$ to $10^{-7}$ M. Both low and high affinity MDP-binding homing molecules that selectively home to lung endothelium can be useful in selectively directing a moiety to lung endothelium in a subject as described further below.

A variety of art known techniques can be used to determine specific binding of a molecule to membrane dipeptidase according to a method of the invention. Conditions suitable for specific binding are described, for example, in Example IVB. Specific binding also can be determined by transfecting cells lacking MDP expression with MDP as described, for example, in Example IVD. In this case, specific binding is determined, in part, by significantly higher binding of a molecule to the MDP-transfected cells than to untransfected cells.

The present invention is directed to the surprising discovery that MDP-binding molecules home specifically to the lung vasculature in spite of MDP expression in other tissues such as kidney. As disclosed herein, injection of MDP-binding GFE-1 (SEQ ID NO: 1) bearing phage into the mouse circulation resulted in rapid binding of the phage to lung microvasculature with some diffuse staining on neighboring cells. The same results were obtained by injecting GFE-1 (SEQ ID NO: 1) bearing phage into rat circulation. In particular, the MDP-binding GFE-1 phage did not bind, for example, to the brush border of kidney proximal tubules, which expresses high levels of MDP. These results indicate that expression of MDP on the luminal surface of lung endothelial cells can mediate homing of MDP-binding phage from the circulation to lung endothelium, while MDP-binding phage cannot access and home to kidney MDP. Thus, MDP mediates selective homing of molecules to lung endothelium in preference to other endothelial cells.

Selective homing of GFE-1 (SEQ ID NO: 1) bearing phage to lung vasculature further demonstrates that a moiety such as a phage can be linked to a MDP-binding homing molecule and thereby selectively directed to lung endothelium. Thus, the present invention provides methods of selectively targeting moieties, such as phage, gene therapy vectors or antibiotics, to lung endothelium for treatment of lung disorders.

A method of the invention for selectively directing a moiety to lung endothelium in a subject involves administering to the subject a conjugate containing a moiety linked to a MDP-binding homing molecule that selectively homes to lung endothelium, whereby the moiety is selectively directed to lung endothelium in the subject. The MDP-binding homing molecule is identified by contacting membrane dipeptidase (MDP) with one or more molecules; and determining specific binding of a molecule to the MDP, where the presence of specific binding identifies the molecule as a MDP-binding homing molecule that selectively homes to lung endothelium. A method of the invention can be useful for targeting genes or medications to the lung in a subject suffering, for example, from pneumonia; asthma; emphysema; respiratory infection; chronic bronchitis; chronic interstitial lung disease; lung cancer; pleurisy or cystic fibrosis. If desired, a method of the invention can be used prophylactically, for example, to selectively direct a moiety to the lung endothelium of an individual with a family history of a lung disorder, for example, or an individual susceptible to lung infection.

A moiety to be selectively directed to lung endothelium can be a physical, chemical or biological material such as a virus, viral gene therapy vector, cell, liposome, microcapsule, micropump or other chambered microdevice, which can be used, for example, as a drug delivery system. Such microdevices generally are biologically inert and, if desired, can be biodegradable or excretable. Various moieties, including microcapsules, which can contain an agent, and methods for linking a moiety or chambered microdevice to an organic molecule are well known in the art and commercially available as described hereinabove. Exemplary moieties that can be linked to a MDP-binding homing molecule that selectively homes to lung endothelium to produce a therapeutic conjugate include therapeutic antimicrobial bacteriophage; antibiotics such as ampicillin; and antiviral agents such as ribavirin (see above).

A moiety to be selectively directed to lung endothelium according to a method of the invention can be, for example, a therapeutic bacteriophage ("phage"). Phage have been shown to be nontoxic (Ochs et al., *J. Clin. Invest.* 50:2559–2568 (1971), which is incorporated herein by reference), and the use of phage therapy is known in the art for treatment of bacterial infections such as antibiotic-resistant infections (Barrow and Soothill, *Trends in Microbiology* 5:268–271 (1997); Slopek et al., *Arch. Immunol. Ther. Exp.* 35:553–561 (1987); and Merrill et al., *Proc. Natl. Acad. Sci., USA* 93:3188–3192 (1996), each of which is incorporated herein by reference; see, also, *Practical Applications of Bacteriophages* CRC Press, Boca Raton, Fla.). For example, in a series of 550 patients, the majority of whom had been unsuccessfully treated with antibiotic therapy, phage therapy resulted in 75–100% success in ameliorating a variety of infections including respiratory tract suppurative infections and broncopneumonia (Slopek et al., supra, 1987). Phage therapy can be particularly useful in treating nosocomial and multi-drug-resistant infections.

Studies have shown that both prophylaxis and treatment are possible using fewer phage than inoculating bacteria, indicating that phage multiply in vivo. Thus, phage therapy can be more effective than conventional treatment with antibiotics, such as streptomycin, tetracycline, ampicillin and sulfafurazole, because of the ability of phage to replicate in vivo. If desired, treatment with a phage conjugate containing a MDP-binding homing molecule can be combined with antibiotic drug therapy.

Preferably, a phage moiety to be selectively directed to lung endothelium is a lytic phage. Such a phage can be readily modified by standard genetic techniques to encode a MDP-binding homing peptide such as GFE-1 (SEQ ID NO: 1) to produce a conjugate that is selectively directed to lung endothelium. Phage useful in the methods of the invention include, for example, T4-related phage, also known as members of the "T-Even family of phages." One skilled in the art understands that a phage moiety is selected with a receptor specificity for the bacteria characteristic of an infection to be treated, for example, phage with receptor specificity for Staphylococcus, Klebsiella, Proteus, Escherichia, Shigella, Pseudomonas or Salmonella. If desired, the pathogenic bacteria can be typed and monitored for phage sensitivity. For treatment of resistant bacteria, a phage conjugate can include, if desired, a mixture of phage with different receptor specificities against a variety of types of bacteria.

A phage/MDP-binding homing conjugate can be administered to a subject, for example, intravenously.

Such a conjugate also can be administered orally, for example, as 10 ml sterile phage lysate half an hour before each meal, with gastric juices neutralized by Vichy water, baking soda or gelatin. After oral administration, phage/MDP-binding homing conjugates access the blood and subsequently are selectively directed to lung endothelium. Administration can be repeated, if needed, daily over a period of several weeks or months. An appropriate dose of a phage conjugate can readily be determined by the skilled person and generally will be in the range of about 100 to about $10^{10}$ plaque forming units (pfu), usually from about 100 to $10^6$ pfu.

A moiety to be selectively directed to lung endothelium for gene therapy can be a gene therapy vector. As used herein, the term "gene therapy vector" means a vector containing a nucleic acid component, which, when delivered to host cells, transiently or permanently expresses an encoded gene product in the host cells in vivo.

A variety of gene therapy vectors that can be selectively directed to lung endothelium using an MDP-binding homing molecule also are known in the art, including viral and non-viral vectors, for example, retroviral vectors, adenoviral vectors, adeno-associated vectors (AAV), herpesvirus vectors and liposome plasmid vectors (Chang, *Somatic Gene Therapy* CRC Press, Boca Raton, Fla. (1995), each of which is incorporated herein by reference). Retroviral and AAV vectors can be useful, for example, for permanent expression, while adenovirus, herpesvirus and liposome-plasmid vectors generally give transient expression. Adenoviral vectors, for example, have been used to express the cystic fibrosis transmembrane receptor (CFTR) and recombinant α1-antitrypsin in lung (Rosenfeld et al., *Cell* 68:143 (1992); Rosenfeld et al., *Science* 252: 431 (1991), each of which is incorporated herein by reference). Liposome DNA complexes also have been used to effect gene transfer to the lung (see, for example, Zhu et al., *Science* 261:209 (1993), which is incorporated herein by reference). Phage vectors also can be useful for expressing a desired nucleic acid in vivo (see, for example, Ivanenkov et al., *Biochimica et Biophysica Acta* 1448:450–462 (1999); Ivanekov et al., Biochimica et Biophysica Acta 1448:463–472 (1999), each of which is incorporated by reference herein).

The methods of the invention for selectively directing a moiety to lung endothelium using a conjugate containing a MDP-binding homing molecule such as GFE-1 (SEQ ID NO: 1) can be useful in the therapeutic management of a variety of pulmonary disorders. For example, by selectively directing a gene therapy vector encoding a cytokine to lung endothelium, the methods of the invention can be useful for immunotherapy. A variety of cytokines or chemokines can be useful in stimulating an immune response, such as an anti-cancer or anti-viral immune response, when administered according to a method of the invention. Such cytokines and chemokines include GM-CSF, G-CSF, IFN-γ, IFN-α, TNF-α, TNF-β, IL-1, IL-2, IL-3, IL-4, IL-6, IL-7, IL-10, IL-12, lymphotactin or DC-CK1 (Pardoll, *Annu. Rev. Immunol.* 13:399–415 (1995; Hunt et al., *J. Immunotherapy* 14:314–321 (1993); Chang, supra, 1995, each of which is incorporated herein by reference). The methods of the invention can be more effective than administration of recombinant cytokines, due to the short half-life of cytokines in the circulation and the lack of their targeting to lung.

As discussed above, the methods of the invention can be useful for treating pulmonary infections by selectively directing a phage moiety or an antibiotic drug such as streptomycin, tetracycline, ampicillin or sulfafurazole to lung endothelium. For example, the methods of the invention can be useful for treating infections secondary to acquired immunodeficiency syndrome (AIDS) or cystic fibrosis.

The methods of the invention for selectively directing a moiety to lung endothelium also can be used for replacement gene therapy of lung disorders such as α1-antitrypsin deficiency and cystic fibrosis (Alton and Geddes, *Brit. J. Hosp. Medicine* 58:38–40 (1997); Wood, *Radiology* 204:1–10 (1997), each of which is incorporated herein by reference). Genes encoding wild type α1-antitrypsin (α1-AT) and the cystic fibrosis transmembrane receptor (CFTR) have been isolated (Riordan et al., *Science* 245:1066–1073 (1989); Rich et al., *Nature* 347:358–63 (1990; Rosenfeld et al., *Science* 252:431–434 (1991), each of which is incorporated herein by reference) and can be transferred selectively to the lung in a gene therapy vector linked to a MDP-binding homing molecule such as GFE-1 (SEQ ID NO: 1).

In one embodiment, the invention provides a method for selectively directing a moiety to lung endothelium where the MDP-binding homing molecule is a peptide including the sequence $X_1$-G-F-E-$X_2$ (SEQ ID NO: 17), where $X_1$ and $X_2$ each is 1 to 10 independently selected amino acids. Such a MDP-binding homing peptide can include, for example, the sequence CGFECVRQCPERC (SEQ ID NO: 1) or CGFELETC (SEQ ID NO: 2).

In another embodiment, the invention provides a method for selectively directing a moiety to lung endothelium where the MDP-binding homing molecule contains the following Structure 1:

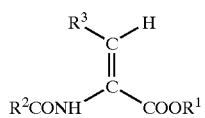

where $R^2$ and $R^3$ are hydrocarbon radicals in the range respectively of 3–10 and 1–15 carbon atoms; in either one of these $R^2$ or $R^3$ hydrocarbon chains 1–6 hydrogens may be replaced by halogens or a nonterminal methylene may be replaced by oxygen or sulfur, including oxidized forms of the latter; additionally, a terminal hydrogen in $R^3$ can also be replaced by hydroxyl or thiol, which may be acylated or carbamoylated; or the hydrogen can be replaced by amino, which may be derivatized as in an acylamino, ureido, amidino, quanidino, or alkyl or substituted amino group, including quaternary nitrogen grouping; or, there may be replacement by acid groups such as carboxylic, phosphonic or sulfonic acid groups or esters or amides thereof, or cyano; or combinations thereof, such as a terminal amino acid grouping; and $R^1$ is hydrogen or lower alkyl ($C_{1-6}$) or dialkylaminoalkyl, or a pharmaceutically acceptable cation. Such an MDP-binding homing molecule can be, for example, 7-(L-2-amino-2-carboxyethylthio)-2-(2,2-dimethylcyclopropanecarboxamido)-2-heptenoic acid, also known as cilastatin.

An MDP-binding homing molecule can be, for example, a compound having Structure 1 in which $R^2$ is branched alkyl or cycloalkyl with a limitation that the carbon adjacent to the carbonyl cannot be tertiary.

An MDP-binding homing molecule also can be, for example, a compound having Structure 1 in which $R^2$ is branched alkyl or cycloalkyl with a limitation that the carbon adjacent to the carbonyl cannot be tertiary, and in which $R^3$ is n-alkyl (1–9 carbons) or n-alkyl (1–9 carbons) having a terminal substituent which is a quaternary nitrogen, amine derivative or amino acid derived group. An MDP-binding homing molecule can be, for example, a compound having Structure 1 in which $R^2$ is 2,2-dimethylcyclopropyl or 2,2-dichlorocyclopropyl and in which $R^3$ is a hydrocarbon chain of 3 to 7 carbon atoms without a terminal substituent or having a terminal substituent which is trimethylammonium, amidino, guanidino or 2-amino-2-carboethylthio.

Exemplary MDP-binding homing molecules having Structure 1 useful in the invention include the following: Z-2-(2,2-dimethylcyclopropanecarboxamido)-8-trimethylammonium hydroxide-2-octenoic acid inner salt; Z-2-(2,2-dichlorocyclopropanecarboxamido)-8-trimethylammonium hydroxide-2-octenoic acid inner salt; Z-2-(2,2-dimethylcyclopropanecarboxamido)-8-guanidino-2-octenoic acid; Z-2-(2,2-dimethylcyclopropanecarboxamido)-8-guanidino-2-octenoic acid; Z-2-(2,2-dimethylcyclopropanecarboxamido)-8-ureido-2-octenoic acid; Z-8-(1-2-amino-2-carboxy ethylthio)-2-(2,2-dimethylcyclopropanecarboxamido)-2-octenoic acid; Z-2-(2,2-dimethylcyclopropanecarboxamido)-2-octenoic acid (racemic and dextrorotatory forms); Z-2-(2,2-dichlorocyclopropanecarboxamido)-2-octenoic acid; 7-(L-2-amino-2-carboxyethylthio)-2-(2,2-dimethylcyclopropanecarboxamido)-2-heptenoic acid; and 6-(L-2-amino-2-carboxyethylthio)-2-(2,2-dimethylcyclopropanecarboxamido)-2-hexenoic acid.

As set forth above, the methods of the invention for targeting treatment to the lungs can be practiced with an MDP-binding homing molecule, which is a Z-2-acylamino-3-monosubstituted propenoate having Structure 1,

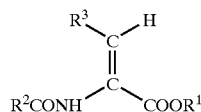

where $R^2$ and $R^3$ are hydrocarbon radicals in the range respectively of 3–10 and 1–15 carbon atoms. In either of these hydrocarbon radicals $R^2$ and $R^3$, up to 6 hydrogens may be replaced by halogens, or a nonterminal methylene may be replaced by oxygen or sulfur, including oxidized forms of the latter.

A terminal hydrogen in $R^3$ also can be replaced by a hydroxyl or thiol group, which may be acylated, such as with an alkanoyl acid of 1–8 carbon atoms, or carbamoylated, including alkyl and dialkyl carbamate derivatives; or the hydrogen can be replaced by an amino group, which may be derivatized as in an acylamino, ureido, amidino, guanidino, or alkyl or substituted alkyl amino group, including quaternary nitrogen groupings; or, alternatively, there may be replacement by acid groups such as carboxylic, phosphonic or sulfonic acid groups or esters or amides thereof, as well as cyano; or combinations thereof, such as a terminal amino acid grouping.

In an MDP-binding homing molecule having Structure 1, $R^2$ is preferably a branched alkyl or cycloalkyl radical ($C_{3-10}$), with a limitation that the carbon adjacent to the carbonyl cannot be tertiary. $R^2$ cannot be phenyl or straight chain lower alkyl of 1–4 carbon atoms, where $R^3$ is straight chain lower alkyl of 1–4 carbon atoms. $R^1$ is hydrogen, lower alkyl ($C_1$–$C_6$) or dialkylaminoalkyl (e.g., —$CH_2CH_2N(C_2H_5)_2$, —$CH_2CH(CH_3)N(CH_3)_2$.

An MDP-binding homing molecule having Structure 1 above can have an asymmetric form. Racemic Z-2-(2,2 dimethylcyclopropanecarboxamido)-2-octenoic acid has been resolved. Activity resides in the dextrorotatory isomer, which has the S-configuration.

Within the definition of $R^2$ of a compound having Structure 1, the following sub-groups are included:
wherein $R^4$ is a straight, branched, or cyclic hydrocarbon radical of 3–10 carbon atoms which may be substituted as specified above in the definition of $R^2$;

wherein $R^5$ is cycloalkyl of 3–6 carbon atoms and $R^6$ is either 1 or 2 alkyl substituents which may be joined to form another ring on the cycloalkyl group, or $R^5$ and $R^6$ may be substituted as specified above in the definition of $R^2$; and

wherein $R^7$ is an alkylene group of 1–3 carbon atoms and $R^8$ is cycloalkyl of 3–6 carbon atoms which may be substituted as specified above in the definitions of $R^2$ and $R^3$.

Particularly preferred substituents within the definition of $R^2$ in Structure 1 include the 2,2-dimethylcyclopropyl and the 2,2-dichlorocyclopropyl groups.

Within the definition of $R^3$ in Structure 1, particularly preferred groups of compounds include n-alkyl (1–9 carbons) and n-alkyl (1–9 carbons) having a terminal substituent which is a quaternary nitrogen, amine derivative, or amino acid derived group.

The term "quaternary nitrogen" is used herein in reference to Structure 1 to mean a tetrasubstituted or heteroaromatic nitrogen which is positively charged. An ammonium moiety, substituted with hydrocarbon groups having 1–7 carbon atoms, which can be the same or different, is signified.

As used herein in reference to Structure 1, the term "amino derivative" means a group such as amino, acylamino, ureido, amidino, guanidino and alkyl (1–7 carbon atoms) derivatives thereof.

As used herein in reference to Structure 1, the term "amino acid derived group" means a moiety such as cysteinyl (—$SCH_2CH(NH_2)COOH$) or sarcosyl (—N($CH_3CH_2COOH$) in which a hydrogen joined to O, N or S of known amino acids is replaced.

Particularly preferred MDP-binding homing molecules having Structure 1 are those in which $R^2$ is 2,2-dimethyl cyclopropyl or dichlorocyclopropyl, and $R^3$ is a hydrocarbon chain of 3 to 7 carbon atoms without a terminal substituent, or having a terminal substituent which is trimethylammonium, amidino, guanidino, or 2-amino-2-carboxyethylthio.

Exemplary MDP-binding homing molecules useful in the invention include Z-2-(2,2-dimethylcyclopropanecarboxamido)-8-trimethylammonium hydroxide-2-octenoic acid inner salt; Z-2-(2,2-dichlorocyclopropanecarboxamido)-8-trimethylammonium hydroxide-2-octenoic acid inner salt; Z-2-(2,2-dimethylcyclopropanecarboxamido)-8-formamidino-2-octenoic acid; Z-2-(2,2-dimethylcyclopropanecarboxamido)-8-guanidino-2-octenoic acid; Z-2-(2,2-dimethylcyclopropanecarboxamido)-8-ureido-2-octenoic acid; Z-8-(L-2-amino-2-carboxyethylthio)-2-(2,2-dimethylcyclopropanecarboxamido)-2-octenoic acid; Z-2-(2,2-dimethylcyclopropanecarboxamido)-2-octenoic acid (racemic and dextrorotatory forms); Z-2-(2,2-dichlorocyclopropanecarboxamido)-2-octenoic acid; 7-(L-2-amino-2-carboxyethylthio)-2-(2,2-dimethylcyclopropanecarboxamido)-2-heptenoic acid; and 6-(L-2-amino-2-carboxyethylthio)-2-(2,2-dimethylcyclopropanecarboxamido)-2-hexenoic acid.

Methods for preparing an MDP-binding homing molecule having Structure 1 are disclosed herein and known in the art. Several methods for preparing such an MDP-binding homing molecule are set forth in Example VI (see, also, U.S. Pat. No. 4,616,038 to Kahan et al., which is incorporated herein by reference).

Additional MDP-binding homing molecules known in the art also can be used to selectively target a gene or medication to lung endothelium according to a method of the invention. Such MDP-binding homing molecules include substituted 2-alkenoic acids including the following Structure 2:

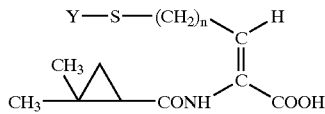

wherein n is an integer from 3 to 5 and Y is a heterocyclic or phenyl group that may be substituted or unsubstituted, and the lower alkyl ($C_1$–$_6$) esters and pharmaceutically acceptable salts thereof.

As used herein in reference to Structure 2, the term "heterocyclic" means pyridyl, pyrimidinyl, tetrazolyl, imidazolyl, thiazolinyl and the like. Such heterocyclic rings and phenyl rings can be unsubstituted or substituted with hydroxyl, oxo, carbonyl, or methyl. Y-groups in Structure 2 include, for example, 2-pyridinyl; 4-pyridinyl; 3-hydroxy-2-pyridinyl; 3-carboxy-2-pyridinyl; 5-carboxy-2-pyridinyl; 2-carboxyphenyl; 1-methyl-1,2,3,4-tetrazol-5-yl; and 4-carboxy-6-hydroxy-2-pyrimidinyl.

The configuration at the cyclopropyl center of a substituted 2-alkenoic acid MDP-binding homing molecule having Structure 2 preferably is S (+), although an R,S (+/−) racemic mixture of the compound also can be used in a method of the invention.

Particularly active MDP-binding homing molecules of this class are those in which n is 4 and Y is 3-carboxy-2-pyridyl or 3-hydroxy-2-pyridyl, each in the S-form. Exemplary MDP-binding homing molecules having Structure 2 include: Z-7-(3-hydroxy-2-pyridylthio)-2-(2,2-dimethylcyclopropanecarboxyamido)-2-heptenoic acid and Z-(5-carboxy-2-pyridylthio)-2-(2,2-dimethylcyclopropanecarboxyamido)-2-heptenoic acid.

An MDP-binding homing molecule having Structure 2, as well as various pharmaceutically acceptable derivatives such as alkali and alkaline earth metal, ammonium or amine salts, or the like, which are also useful in the invention, can be prepared by the skilled person using routine methods. An MDP-binding homing molecule having Structure 2 can be prepared, for example, by condensation of a bromoalkenoic acid with the appropriate mercaptan, YSH, in water in the presence of sodium bicarbonate at ambient temperature as described, for example, in U.S. Pat. No. 4,406,902 to Ashton et al., which is incorporated herein by reference.

An MDP-binding homing molecule useful in the invention also can be a phosphinic acid having the following Structure 3:

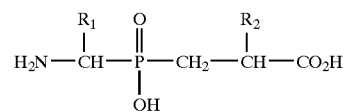

or the following Structure 4:

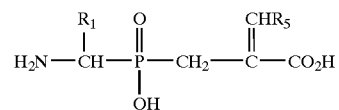

where:

$R_1$ is
(a) $C_2$–$C_{12}$ linear or branched unsubstituted alkyl;
(b) $C_2$–$C_{12}$ linear or branched substituted alkyl;
(c) $C_2$–$C_{12}$ linear or branched monoalkenyl;
(d) $C_2$–$C_{12}$ linear or branched alkynyl;
(e) $C_7$–$C_{20}$ aralkyl, wherein the alkyl chain is linear or branched $C_1$–$C_8$ and the aryl moiety is $C_6$–$C_{12}$;
(f) $C_3$–$C_7$ cycloalkyl;
(g) $C_4$–$C_{10}$ cycloalkylalkyl, for structure 4 only; where the above values for $R^1$, excluding (a), can be substituted by one or more: $C_1$–$C_4$ alkoxy, $C_6$–$C_{12}$ aryloxy, $C_1$–$C_4$ alkylthio, $C_6$–$C_{12}$ arylthio, $C_3$–$C_6$ cycloalkyloxy, $C_3$–$C_6$ cycloalkylthio, $C_{7-C10}$ aralkyloxy, $C_7$–$C_{16}$ aralkylthio;

$R_2$ is
(a) H or $C_1$–$C_{12}$ linear or branched alkyl;
(b) $C_2$–$C_{12}$ linear or branched monoalkenyl;
(c) $C_7$–$C_{20}$ aralkyl, wherein the alkyl chain is linear or branched $C_1$–$C_8$ and the aryl moiety is $C_6$–$C_{12}$;
(d) heterocyclic alkyl, wherein the alkyl chain is linear or branched $C_1$–$C_8$ and the heterocyclic ring is 5–6 membered, optionally fused with a benzene ring, fully aromatic, containing 1–2: O, N or S heteroatoms;
(e) $C_3$–$C_7$ cycloalkyl;
(f) $C_4$–$C_{10}$ cycloalkylalkyl;
where the above values for $R_2$ can be substituted by one or more: halo, hydroxy, carboxy, $C_1$–$C_4$ alkoxycarbonyl, $C_7$–$C_{16}$ arylalkoxycarbonyl, $C_3$–$C_7$ cycloalkyl, $C_1$–$C_4$ alkoxy, $C_6$–$C_{12}$ aryloxy, $C_3$–$C_6$ cycloalkyloxy, $C_3$–$C_6$ cycloalkylthio, amino, mono- or di-$C_1$–$C_8$ alkylamino, thio, $C_1$–$C_4$ alkylthio, $C_6$–$C_{12}$ arylthio, $C_7$–$C_{16}$ aralkylthio, or the radical —S—$(CH_2)_n$—CH($NH_2$)COOH;

$R^5$ is
(a) H or $C_1$–$C_{12}$ linear or branched alkyl;
(b) $C_2$–$C_{12}$ linear or branched monoalkenyl;

(c) $C_7$–$C_{20}$ aralkyl, wherein the alkyl chain is linear or branched $C_1$–$C_8$ and the aryl moiety is $C_6$–$C_{12}$;

(d) heterocyclic alkyl, wherein the alkyl chain is linear or branched $C_1$–$C_8$ and the heterocyclic ring is 5–6 membered, optionally fused with a benzene ring, fully aromatic, containing 1–2: O, N or S heteroatoms;

(e) $C_4$–$C_{10}$ cycloalkylalkyl;

(f) $C_3$–$C_7$ cycloalkyl;

where the above value for $R_5$ can be substituted by one or more: halo, hydroxy, carboxy, $C_1$–$C_4$ alkoxycarbonyl, $C_7$–$C_{16}$ arylalkoxycarbonyl, $C_3$–$C_7$ cycloalkyl, $C_1$–$C_4$ alkoxy, $C_6$–$C_{12}$ aryloxy, $C_3$–$C_6$ cycloalkyloxy, $C_3$–$C_6$ cycloalkylthio, amino, mono-or di-$C_1$–$C_8$ alkylamino, thio, $C_1$–$C_4$ alkylthio, $C_6$–$C_{12}$ arylthio, $C_7$–$C_{16}$ aralkylthio, or the radical —S—(CH$_2$)$_n$—CH(NH$_2$)COOH; and including MDP-binding stereoisomers and racemates thereof Structures 3 and 4.

In an MDP-binding homing molecule having Structure 3 or 4, the values for $R_1$ for (a) $C_2$–$C_{12}$ linear or branched unsubstituted alkyl include ethyl, propyl, isopropyl, n-butyl, isobutyl, sec-butyl, t-butyl, n-pentyl, isopentyl, n-hexyl, n-heptyl, n-octyl, iso-octyl, n-decyl, n-undecyl, n-dodecyl and the like. Preferred in this series is n-butyl, isobutyl, n-pentyl and n-hexyl.

In an MDP-binding homing molecule having Structure 3 or 4, values for $R_1$ for (b) $C_1$–$C_{12}$ linear or branched alkyl, where substituted, include the values above for $R_1$ (a), substituted by the above-defined substituents, including the following preferred substituents: methoxy, ethoxy, propoxy, butoxy, methylthio, ethylthio, propylthio, butylthio, cyclopentyloxy, cyclopentylthio, cyclopropylthio, benzylthio, 2-phenethylthio, 2-phenethylthio and the like.

In an MDP-binding homing molecule having Structure 3 or 4, values for $R^1$ for (e) $C_2$–$C_2$ linear or branched monoalkenyl include ethenyl, propenyl, 1-butenyl, 2-butenyl, 1-pentenyl, 2-pentenyl, 2-methyl-2-butenyl and the like.

In an MDP-binding homing molecule having Structure 3 or 4, values for $R_1$ for (d) $C_2$–$C_{12}$ linear or branched alkynyl include: ethynyl, propynyl, 1-butynyl, 2-butynyl, 2-methyl-3-pentynyl and the like.

Values for $R^1$ for (d) $C_2$–$C_{12}$ linear or branched alkynyl include: ethynyl, propynyl, 1-butynyl, 2-butynyl, 2-methyl-3-pentynyl and the like.

Values for $R_1$ for (e) $C_7$–$C_{20}$ aralkyl include benzyl, 2-phenylethyl, 1-phenylethyl, 4-methylphenylmethyl and the like. Preferred in this series is benzyl.

Values for $R_1$ for (f) $C_4$–$C_{10}$ cycloalkylalkyl include: cyclohexylmethyl, cyclopentylmethyl, 2-cyclohexylethyl, 2-cycloctylethyl, and the like. Preferred in this series is cyclopentylmethyl and cyclohexylmethyl.

Values for $R_1$ for (g) $C_3$–$C_7$ cycloalkyl include: cyclopropyl, cyclobutyl, cyclopentyl, cyclohexyl, and the like. Preferred in this series is cyclopentyl and cyclohexyl.

Preferred substituent values for $R_1$ include: methoxy, ethoxy, phenoxy, methylthio, ethylthio, phenylthio, benzyloxy, 2-phenylethyloxy, benxylthio, 2-phenylethylthio, and the like.

The values of the alkyl, alkenyl groups for $R_2$ and $R_5$, except where noted otherwise, represented by any of the variables include linear or branched, alkyl and monoalkenyl and chain hydrocarbon radicals from two to twelve carbon atoms, for example, ethyl, n-propyl, isopropyl, n-butyl, isobutyl, sec-butyl, t-butyl, n-pentyl, isopentyl, n-heptyl, n-nonyl, 4,4-dimethylpentyl, or vinyl, allyl, 1-butenyl, 2-butenyl, 5-hexenyl and the like. Preferred are isopropyl, n-butyl, n-pentyl, n-heptyl or 1-butenyl.

Values of $C_3$–$C_7$ cycloalkyl and $C_4$–$C_{10}$ cycloalkylalkyl include: cyclopentyl, cyclohexyl, cyclopentyl-methyl, cyclopentylethyl, cyclohexylmethyl, cyclohexylethyl, cyclopropyl, and the like.

The aralkyl group represented by the above variables has from one to eight carbon atoms in the alkyl portion and "aryl" where noted, represents phenyl, naphthyl, or biphenyl. Representative examples include benzyl, phenethyl, 4-phenyl-n-butyl, 1-phenyl-n-octyl, and the like.

In an MDP-binding homing molecule of the invention having Structure 3 or 4, the aromatic heterocyclic, i.e. "heteroaryl" substituent, are synonymous, and recited above represents a 5- or 6-membered aromatic ring containing from one to three O, N or S heteroatoms, preferably one O or S or 1–3N heteroatoms, such as for example, pyridyl, thienyl, furyl, imidazolyl, and thiazolyl as well as any bicyclic group derivable therefrom in which any of the above heterocyclic rings is fused to a benzene ring such as, for example, indolyl, quinolinyl, isoquinolinyl, benzimidazolyl, benzothiazolyl, benzofuryl, and benzothienyl.

The named substituents on the $R_2$ and $R_5$ alkyl and alkenyl chains can be present on the aromatic rings in the aralkyl, heterocyclic alkyl and heteroaryl groupings as well. The site of substitution can be any available sites and the substitution can involve one or more of the same or different groups.

The substituents are: halo, meaning fluoro, chloro, bromo or iodo; hydroxy; carboxy; $C_1$–$C_4$ linear or branched alkoxycarboxy, e.g. methoxycarbonyl and ethoxycabonyl; $C_7$–$C_{16}$ arylalkoxy carbonyl, e.g. benzyloxycarbonyl, n-butyloxyoarbonyl; $C_3$–$C_7$ cycloalkyl, e.g. cyclopentyl and cyclohexyl; $C_1$–$C_4$ alkoxy, e.g. t-butoxy and ethoxy; $C_6$–$C_{12}$ aryloxy, e.g. biphenyloxy, benzyloxy; amino; mono- or di-$C_1$–$C_8$ dialkylamino, e.g. methylamino, isopropylamino, n-butylamino, isohexylamino, N,N-diethylamino, methylethylamino, methyl-t-butylamino, di-n-octylamino; thio; $C_1$–$C_4$ alkylthio, e.g. methylthio, ethylthio $C_6$–$C_{12}$ arylthio, e.g. phenylthio; $C_7$–$C_{16}$ aralkylthio, e.g. benzylthio, naphthyl-methylthio; the radicals —S—CH$_2$—CH(NH$_2$)COOH and —S—(CH$_2$)$_2$—CH(NH$_2$)COOH, both preferably in the L-configuration; and, where a thio substituent is present, $R_2$ or $R_5$ must be at least a $C_2$ alkyl grouping. Where an aryl or heteroaryl group is present in the substituent, the ring carbons can additionally be substituted by one or more of linear or branched $C_1$–$C_4$ alkyl, e.g. methyl, ethyl, isopropyl, t-butyl; trihalomethyl, "halo" having the same meaning as described above, e.g. trichloromethyl, trifluoromethyl; nitro, cyano or sulfonamide.

Preferred are the compounds wherein: $R_1$ is cyclohexylmethyl, cyclopentyhnethyl, n-pentyl, n-butyl, n-hexyl, isobutyl, $R_2$ and $R_5$ are: $C_3$–$C_7$ cycloalkyl; $C_1$–$C_{10}$ linear or branched alkyl, substituted or unsubstituted; $C_7$–$C_{14}$ aralkyl, substituted or unsubstituted. Wherein these groups can be substituted with halo, amino, mono- or di-$C_1$–$C_4$ linear or branched alkylamino, carboxyl, $C_1$–$C_4$ alkoxycarbonyl, hydroxy, $C_1$–$C_4$ alkoxy, $C_5$–$C_6$ cycloalkyl, $C_6$–$C_{10}$ aryroxy, thio, $C_1$–$C_4$ linear or branched alkylthio, $C_6$–$C_{10}$ arylthio, $C_7$–$C_{14}$ aralkylthio, —S—(CH$_2$—)$_n$—CH(NH$_2$)CO$_2$H; wherein the aryl group ring carbons can further be substituted by linear or branched $C_1$–$C_4$ alkyl; $R_3$ and $R_4$ are hydrogen, $C_1$–$C_4$ linear or branched alkyl e.g. methyl, ethyl, or $C_7$–$C_{14}$ aralkyl e.g. benzyl.

In an MDP-binding homing molecule having Structure 3 or 4, the carbon preferably is attached to $R_1$ in the (R) or (RS) configuration, more preferably (R), and the carbon attached to $R_2$ is in the (R), (RS) or (S) configuration, preferably (RS) or (S) and if $R_5$ is present, the double bond preferably is in the Z configuration. One skilled in the art understands that an MDP-binding homing molecule based on Structure 3 can be used in the form of salts derived from inorganic or organic acids and bases.

Methods for preparing an MDP-binding homing molecule having Structure 3 or Structure 4 are well known in the art. See, for example, Parsons et al., *Biochemistry International* 23:1107–1115 (1991); and U.S. Pat. No. 5,145,990, each of which is incorporated herein by reference.

A variety of other MDP-binding homing molecules known in the art also can be useful for selectively directing a gene or medication to lung endothelium according to a method of the invention. Such MDP-binding homing molecules include those described in Kahan et al., U.S. Pat. No. 4,616,038; Ashton et al., U.S. Pat. No. 4,406,902; Parsons et al., U.S. Pat. No. 5,145,990; Parsons et al., *Biochem. International* 23:1107–1115 (1991); Uchida et al., U.S. Pat. No. 5,061,730; Hashimoto et al., *J. Antibiotics* XLIII:281–285 (1990); and Takase et al., *J. Antibiotics* XLIII:38–42 (1990), each of which is incorporated herein by reference.

Metastatic cells display an altered repertoire of cell adhesion molecules, allowing escape from the primary tumor, adhesion and penetration of the extracellular matrix and entry into the microvasculature. Most such cells are destroyed by geometric and hemodynamic forces in their first encounter with the narrow capillary net, usually in the lungs. Although the frequency of metastasis to the lungs has been attributed solely to mechanical entrapment of tumor cell emboli, it has long been observed that certain tumor cell types prefer to metastasize to specific target organs.

Several lines of evidence indicate that the selection of a target organ for metastasis is mediated by specific interactions between blood-born cancer cells and the endothelium of that target organ (Albelda, *Lab. Invest.* 68: 4–17 (1993); Auerbach et al., *Cancer Res.* 47:1492–1496 (1987); Johnson et al., Cancer Res. 51:394–399 (1991), each of which is incorporated herein by reference). In the lung, two vascular receptors have been found to mediate adhesion of metastatic cells. LuECAM-1, an endothelial surface protein with sequence homology to chloride channels, mediates adhesion of malignant melanoma cells to lung endothelium (Elble et al., *J. Biol. Chem.* 272:27853–27861 (1997), which is incorporated herein by reference). Furthermore, a protease, lung endothelial dipeptidylpeptidase IV (DPP IV/CD 26), promotes homing of metastatic breast and prostate carcinoma cells to lung (Johnson et al., *J. Cell Biol.* 121: 1423–1432 (1993), which is incorporated herein by reference). Fibronectin present on the surface of the metastatic cells was shown to be the ligand for DPP IV-dependent homing of the breast cancer cells to lung vasculature (Chen et al., *J. Biol. Chem.* 273:24207–24215 (1998), which is incorporated herein by reference). These results indicate that organ-selective homing can be mediated by classical cell adhesion molecules as well as other molecules.

As disclosed herein, selective homing of GFE-1 (SEQ ID NO: 1) to lung endothelium in vivo is mediated by the cell surface protease, MDP. As further disclosed herein, administration of GFE-1 (SEQ ID NO: 1) can inhibit experimental lung metastasis of two melanoma cell lines (human C8161 and mouse B16) in mice, demonstrating that GFE-1 (SEQ ID NO; 1) can compete with metastasizing tumor cells for binding to the same receptor (see FIG. 8). These results indicate that MDP serves as a receptor for metastasizing tumor cells on lung vasculature and that an MDP-binding homing molecule can reduce or prevent the anchoring of lung metastases.

Thus, the present invention provides a method of reducing or preventing lung metastasis in a subject having cancer by administering to the subject a membrane dipeptidase (MDP)-binding homing molecule. Primary tumors that commonly spread to the lungs include breast, colorectal, lung, testicular, pancreatic, esophageal, stomach, ovarian, renal cell and prostate carcinomas, osteogenic and soft tissue sarcomas and melanoma (Smith, *Seminars Oncology Nurs.* 14:178–186 (1998), which is incorporated herein by reference). The methods of the invention can be used, for example, to reduce or prevent lung metastasis of breast cancer, kidney cancer, melanoma, bladder cancer, cancer of the cervix, ovarian cancer, prostate cancer, colorectal cancer or lung cancer.

As used herein, the term "metastasis" means the transfer of malignant cells from one site to another site not directly connected with it, after which the cells form a proliferative focus. Thus, metastatic cells become detached from a primary tumor, move to a different part of the body and grow as a separate mass of tumor. One skilled in the art understands that a malignant cell can travel locally from a first site within an organ to a second site within the same organ or can travel distantly within the body to a different organ. Furthermore, malignant cells of a metastasis can themselves give rise to additional metastases.

The term "lung metastasis," as used herein, refers to the transfer of malignant cells to one or more sites within lung not directly connected with the first site, after which the cells form a proliferative focus within the lung. The resulting detached masses of cancer cells within the lung are termed lung "metastases" or secondary tumors. Lung metastases can originate from a variety of primary cancers, which they generally will resemble histologically. Breast cancer, kidney cancer and melanoma, for example, frequently metastasize to lung. In addition, cancers of the bladder, cervix, ovary and prostate metastasize to lung and, less frequently, colorectal cancers or primary lung cancers metastasize to one or more secondary sites in lung.

The term "reducing or preventing," as used herein in reference to lung metastasis, means that the rate or extent of lung metastasis is diminished. Thus, lung metastasis is reduced or prevented where the development of lung metastasis is completely precluded or is significantly delayed; or where the size or number of lung metastases is significantly diminished. One skilled in the art understands that a delay in development of lung metastases or a decrease in the size or number of lung metastases is measured relative to the rate or extent of lung metastases in one or more control subjects not treated with an MDP-binding homing molecule according to a method of the invention.

If addition, a subject not having detectable cancer can be treated prophylactically with an MDP-binding homing molecule to reduce or prevent the future occurrence of lung metastases. Such a subject can be, for example, suspected of having cancer or can have a family history of cancer.

As set forth above, an MDP-binding homing molecule exhibits selective homing to lung endothelium and is characterized, in part, by exhibiting specific binding to membrane dipeptidase. An MDP-binding homing molecule useful in reducing or preventing lung metastasis can readily be identified by specific binding to MDP as described hereinabove. If desired, additional MDP-binding homing molecule also can be identified by the ability to competitively inhibit binding of known MDP-binding peptides, for example, GFE-1 (SEQ ID NO: 1) or cells, for example, C8161 cells to membrane dipeptidase.

In one embodiment, an MDP-binding homing molecule useful in reducing or preventing lung metastasis is a lung homing peptide including the sequence $X_1$-G-F-E-$X_2$ (SEQ ID NO: 17), where $X_1$ and $X_2$ each is 1 to 10 independently selected amino acids, such as a peptide including the sequence CGFECVRQCPERC (SEQ ID NO: 1) or CGFELETC (SEQ ID NO: 2). Such an MDP-binding homing molecule can be, for example, the peptide CGFECVRQCPERC (SEQ ID NO: 1) or CGFELETC (SEQ ID NO: 2). Additional MDP-binding homing molecules containing the sequence $X_1$-G-F-E-$X_2$ (SEQ ID NO: 17), where $X_1$ and $X_2$ each is 1 to 10 independently selected amino acids, can be identified as described below, for example, by screening a combinatorial peptide library which includes the motif GFE as invariant residues.

In another embodiment, an MDP-binding homing molecule is a membrane dipeptidase inhibitor. As used herein, the term "membrane dipeptidase inhibitor" is synonymous with "MDP inhibitor" and means an organic molecule that selectively decreases the enzymatic activity of membrane dipeptidase. In general, an MDP inhibitor is a molecule that binds to the active site of MDP. An MDP inhibitor can be an organic molecule such as a drug; peptide; modified peptide or peptide mimetic; protein or protein fragment; nucleic acid molecule such as a ribonucleic or deoxyribonucleic acid; oligosaccharide; lipid; glycolipid; or lipoprotein. Exemplary MDP inhibitors disclosed herein are CGFECVRQCPERC (SEQ ID NO: 1) and cilastatin.

The term "selectively inhibits," as used herein in reference to an MDP inhibitor, means that the inhibitor decreases MDP activity in a manner that is selective for the MDP enzyme as compared to related but different enzymes such as other proteases. Thus, an MDP inhibitor is distinct from a non-specific inhibitor of, for example, zinc metalloproteases. Thus, an MDP inhibitor can selectively decrease MDP activity while having little or no effect on the activity of, for example, dipeptidyl peptidase IV.

Assays for measuring MDP enzymatic activity are known in the art. MDP cleaves dipeptide substrates in which the N-terminal amino acid is in the L-configuration and is unblocked. The C-terminal amino acid is either in the L- or D-configuration, with the enzyme hydrolyzing substrates with a D-configuration C-terminal residue more rapidly. MDP activity can be assayed, for example, using glycyl-D-phenylalanine (Gly-D-Phe) as a substrate (Keynan et al., supra, 1996; Parsons et al., supra, 1991). A convenient specific fluorimetric assay for MDP enzymatic activity uses Gly-D-Phe as a substrate and subsequent reaction of D-amino acid oxidase with the released D-Phe (see Example IVE; see, also, Heywood and Hooper, *Analyt. Biochem.* 226:10–14 (1995), which is incorporated herein by reference).

Figure 7:
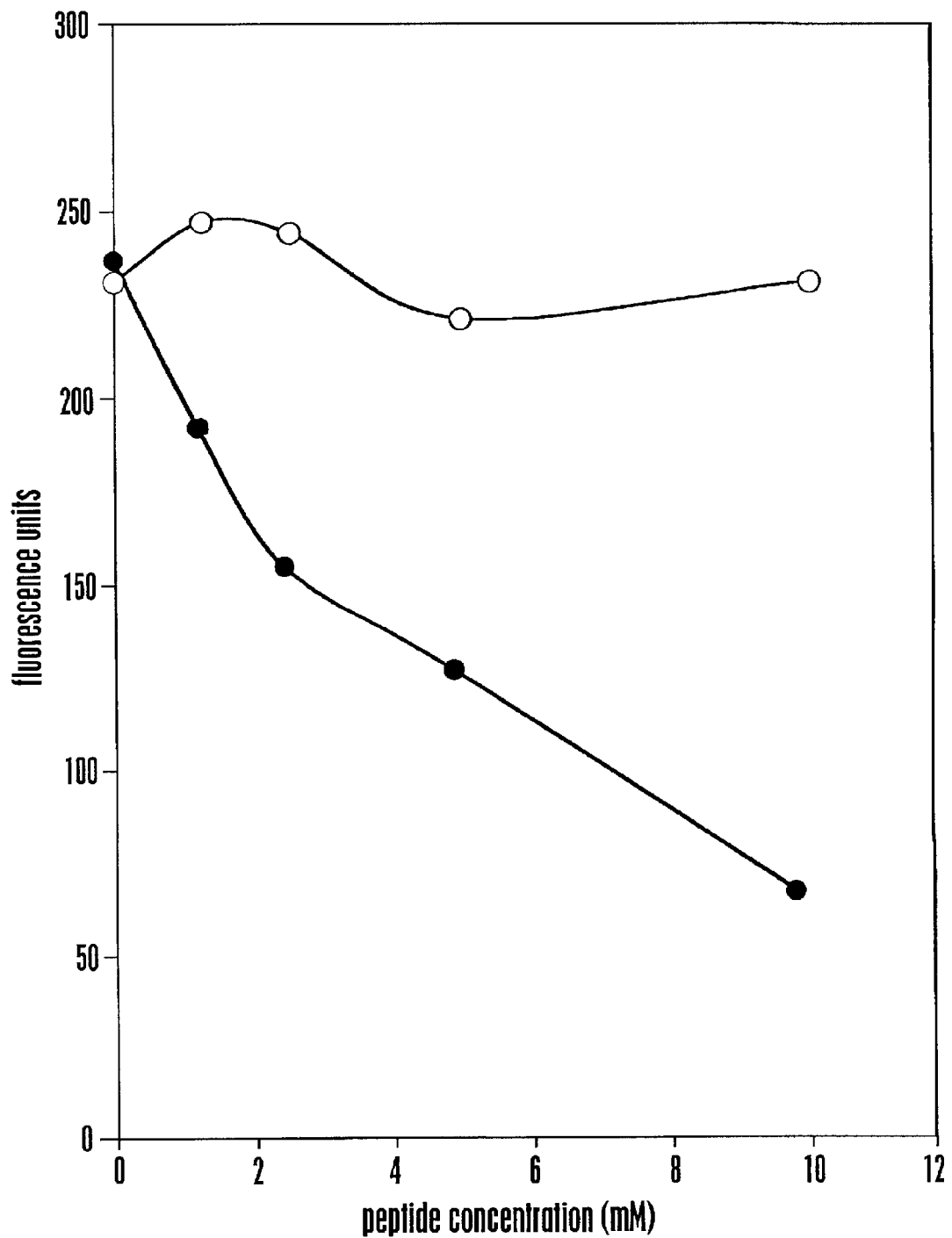
FIG. 7 shows inhibition of MDP activity by the GFE-1 peptide CGFECVRQCPERC (SEQ ID NO: 1). Extracts from MDP-expressing COS-1 cells were assayed for MDP activity in the presence of increasing concentrations of CGFECVRQCPERC (SEQ ID NO: 1; GFE-1) (●) or CARAC control peptide (SEQ ID NO: 443), shown as (○).

A membrane dipeptidase inhibitor can be a molecule that exhibits structural homology to a natural MDP substrate. For example, following cleavage of the tripeptide glutathione by γ-glutamyl transpeptidase to form glutamate and cysteinylglycine (Cys-Gly), the dipeptide Cys-Gly is recognized and cleaved by MDP, which cleaves only dipeptides. The amino acid sequence of glutathione is similar to the N-terminal portion of GFE-1 (SEQ ID NO: 1), in which the first two amino acids are Cys-Gly. As shown in FIG. 7, GFE-1 (SEQ ID NO: 1) inhibits hydrolysis of the Gly-D-Phe substrate in a dose-dependent manner, indicating that GFE containing peptides such as GFE-1 (SEQ ID NO: 1) can be MDP inhibitors. These results further indicate that an MDP inhibitor can be structurally similar to a naturally occurring MDP substrate.

A variety of MDP inhibitors are known in the art. For example, an MDP inhibitor can be an MDP-binding homing molecule such as an MDP-binding molecule having Structure 1, Structure 2, Structure 3 or Structure 4, described hereinabove.

An MDP inhibitor useful in the invention can have, for example, a Ki for membrane dipeptidase of about $10^{-4}$ M to about $10^{-12}$ M. For example, a MDP inhibitor including the sequence $X_1$-G-F-E-$X_2$ (SEQ ID NO: 17), where $X_1$ and $X_2$ each is 1 to 10 independently selected amino acids, can have, for example, a Ki for membrane dipeptidase of about $2 \times 10^{-5}$ M to $10^{-7}$ M, for example, a Ki of about $10^{-6}$ to $10^{-7}$ M.

An MDP inhibitor useful in the invention can exhibit, for example, a Ki against MDP of 1000 nM or less. An MDP inhibitor useful in reducing or preventing lung metastasis also can exhibit, for example, a Ki against MDP of 100 nM or less or a Ki of 1 nM or less. For example, an MDP inhibitor having Structure 3 or Structure 4 can be a tight binding inhibitor with a Ki from, for example, about 0.5 nM to 10 nM. MDP inhibitors having Structure 3 or Structure 4 therefore can be particularly useful in the methods of the invention for reducing or preventing lung metastasis by administering an MDP inhibitor to a subject having cancer.

In another preferred embodiment, an MDP inhibitor comprises Structure 1, where $R^2$ and $R^3$ are hydrocarbon radicals in the range respectively of 3–10 and 1–15 carbon atoms; in either one of these $R^2$ or $R^3$ hydrocarbon chains 1–6 hydrogens may be replaced by halogens or a nonterminal methylene may be replaced by oxygen or sulfur, including oxidized forms of the latter; additionally, a terminal hydrogen in $R^3$ can also be replaced by hydroxyl or thiol, which may be acylated or carbamoylated; or the hydrogen can be replaced by amino, which may be derivatized as in an acylamino, ureido, amidino, quanidino, or alkyl or substituted amino group, including quaternary nitrogen grouping; or, there may be replacement by acid groups such as carboxylic, phosphonic or sulfonic acid groups or esters or amides thereof, or cyano; or combinations thereof, such as a terminal amino acid grouping; and $R^1$ is hydrogen or lower alkyl ($C_{1-6}$) or dialkylaminoalkyl, or a pharmaceutically acceptable cation. Such an MDP inhibitor for reducing or preventing lung metastasis can be, for example, 7-(L-2-amino-2-carboxyethylthio)-2-(2,2-dimethylcyclopropanecarboxamido)-2-heptenoic acid, also known as cilastatin.

An MDP inhibitor can be, for example, a compound having Structure 1 in which $R^2$ is branched alkyl or cycloalkyl with a limitation that the carbon adjacent to the carbonyl cannot be tertiary.

An MDP inhibitor also can be, for example, a compound having Structure 1 in which $R^2$ is branched alkyl or cycloalkyl with a limitation that the carbon adjacent to the carbonyl cannot be tertiary, and in which $R^3$ is n-alkyl (1–9 carbons) or n-alkyl (1–9 carbons) having a terminal substituent which is a quaternary nitrogen, amine derivative or amino acid derived group. An MDP inhibitor can be, for example, a compound having Structure 1 in which $R^2$ is 2,2-dimethylcyclopropyl or 2,2-dichlorocyclopropyl and in which $R^3$ is a hydrocarbon chain of 3 to 7 carbon atoms without a terminal substituent or having a terminal substituent which is trimethylammonium, amidino, guanidino or 2-amino-2-carboethylthio.

Exemplary MDP inhibitors having Structure 1 useful in the invention include the following: Z-2-(2,2- dimethylcyclopropanecarboxamido)-8-trimethylammonium hydroxide-2-octenoic acid inner salt; Z-2-(2,2-dichlorocyclopropanecarboxamido)-8-trimethylammonium hydroxide-2-octenoic acid inner salt; Z-2-(2,2-dimethylcyclopropanecarboxamido)-8-guanidino-2-octenoic acid; Z-2-(2,2-dimethylcyclopropanecarboxamido)-8-guanidino-2-octenoic acid; Z-2-(2,2-dimethylcyclopropanecarboxamido)-8-ureido-2-octenoic acid; Z-8-(1-2-amino-2-carboxy ethylthio)-2-(2,2-dimethylcyclopropanecarboxamido)-2-octenoic acid; Z-2-(2,2-dimethylcyclopropanecarboxamido)-2-octenoic acid (racemic and dextrorotatory forms); Z-2-(2,2-dichlorocyclopropanecarboxamido)-2-octenoic acid; 7-(L-2-amino-2-carboxyethylthio)-2-(2,2-dimethylcyclopropanecarboxamido)-2-heptenoic acid; and 6-(L-2-amino-2-carboxyethylthio)-2-(2,2-dimethylcyclopropanecarboxamido)-2-hexenoic acid.

The present invention also provides a method of reducing or preventing lung metastasis in a subject having cancer by administering to the subject a MDP negative regulatory agent. A MDP negative regulatory agent useful in the invention can be, for example, a soluble MDP polypeptide or an antibody that selectively reacts with MDP.

Further provided herein are methods of reducing or preventing cell homing to lung endothelium in a subject by administering to the subject a MDP negative regulatory agent. A MDP negative regulatory agent useful for reducing or preventing cell homing to lung endothelium can be, for example, a soluble MDP polypeptide or an antibody that selectively reacts with MDP.

As used herein, the term "MDP negative regulatory agent" means an organic molecule that, directly or indirectly, selectively reduces MDP expression or activity. Such MDP negative regulatory agents can be, for example, drugs; nucleic acid molecules, including ribonucleic acid molecules and deoxyribonucleic acid molecules; peptides; variants or modified peptides or peptide mimetics; proteins or fragments thereof; antibodies or fragments thereof; oligosaccharides; lipids; glycolipids; or lipoproteins.

One skilled in the art understands that a MDP negative regulatory agent can act by a variety of mechanisms to selectively reduce MDP expression or activity. An MDP negative regulatory agent can be, for example, an organic molecule that acts to reduce the amount of functional MDP expressed in lung endothelium. Such an agent can selectively reduce MDP transcription or translation and can be, for example, an antisense oligonucleotide, a transcription factor that negatively regulates MDP expression, or a nucleic acid molecule encoding such a transcription factor.

An MDP negative regulatory agent also can be, for example, a fragment of MDP that effectively competes with wild type membrane dipeptidase to reduce or prevent metastatic or other cells from selectively homing to MDP in lung endothelium. A soluble, extracellularly expressed form of MDP or other dominant negative fragment of MDP can be a MDP negative regulatory agent useful in the invention. A MDP regulatory agent also can be an MDP mimic, which is a protein or other organic molecule that shares tertiary structural homology with MDP or a subpart thereof, and which, when expressed, competes with endogenous MDP for binding to metastatic or other homing cells such as lymphocytes. An MDP mimic can structurally resemble the region of MDP that contacts a metastatic cell; an MDP mimic can structurally resemble, for example, the active site of MDP.

In one embodiment, a MDP negative regulatory agent is an antibody that selectively reacts with MDP. As used herein, an antibody that "selectively reacts with MDP" binds with substantially higher affinity to membrane dipeptidase than to an unrelated polypeptide such as another zinc metalloprotease. The term "antibody" is used herein in its broadest sense to include polyclonal and monoclonal antibodies, as well as polypeptide fragments of antibodies that retain a selective affinity for membrane dipeptidase of at least about $1 \times 10^5$ $M^{-1}$. Antibody fragments such as Fab, $F(ab')_2$ and Fv fragments can selectively react with membrane dipeptidase and, therefore, are included within the meaning of the term antibody as defined herein. The term antibody as used herein includes naturally occurring antibodies, as well as non-naturally occurring antibodies and fragments such as chimeric antibodies and humanized antibodies that are selectively reactive with membrane dipeptidase.

Methods for producing antibodies are routine in the art. Membrane dipeptidase, which can be prepared from natural sources or produced recombinantly as described above, or a fragment thereof, such as a synthetic peptide, can be used as an immunogen. Non-immunogenic fragments or synthetic peptides can be made immunogenic by coupling the hapten to a carrier molecule such as bovine serum albumin (BSA) or keyhole limpet hemocyanin (KLH). In addition, various other carrier molecules and methods for coupling a hapten to a carrier molecule are well known in the art as described, for example, by Harlow and Lane, *Antibodies: A Laboratory Manual* (Cold Spring Harbor Laboratory Press, 1988), which is incorporated herein by reference. Antibodies, including non-naturally occurring antibodies such as, chimeric and humanized antibodies, also can be constructed using solid phase peptide synthesis, produced recombinantly or obtained, for example, by screening combinatorial libraries consisting of variable heavy chains and variable light chains as described by Borrebaeck (Ed.), *Antibody Engineering* (Second edition) New York: Oxford University Press (1995), which is incorporated herein by reference.

In another embodiment, a MDP negative regulatory agent is a soluble MDP polypeptide. As used herein, the term "soluble polypeptide" means a polypeptide that is not membrane bound. A soluble MDP polypeptide useful in the invention is secreted and, thus, expressed extracellularly.

A soluble MDP polypeptide useful in the invention can be, for example, a truncated or mutated MDP polypeptide lacking one or more C-terminal residues required for GPI anchor addition (see FIG. 9). To determine whether a particular truncated or mutated MDP derivative is soluble, the derivative can be expressed, for example, in COS cells, and the transfected cells and supernatant subsequently assayed for MDP activity to determine whether the MDP is membrane bound or soluble.

The present invention also provides a method of identifying a molecule that reduces or prevents lung metastasis by contacting membrane dipeptidase (MDP) with one or more molecules; and determining MDP activity in the presence of the molecule as compared to a control value, where diminished MDP activity in the presence of the molecule identifies the molecule as a molecule that reduces or prevents lung metastasis. The membrane dipeptidase can be, for example, substantially purified. MDP activity can be determined, for example, by release of D-Phe from Gly-D-Phe.

In one embodiment of the invention, a molecule that reduces or prevents lung metastasis can be identified by contacting membrane dipeptidase (MDP) with one or more molecules; determining MDP activity in the presence of the molecule as compared to a control value; administering the molecule to a subject having cancer; and assaying lung metastasis in the subject as compared to a control level of metastasis, where diminished MDP activity in the presence of the molecule identifies the molecule as a molecule that reduces or prevents lung metastasis.

The following examples are intended to illustrate but not limit the present invention.

EXAMPLE I

In Vivo Panning

This example demonstrates methods for preparing a phage display library and screening the library using in vivo panning to identify phage expressing peptides that home to a selected organ or tissue.

A. Preparation of Phage Libraries:

Phage display libraries were constructed using the fuse 5 vector as described by Koivunen et al., supra, 1995; see, also, Koivunen et al., supra, 1994b). Libraries encoding peptides designated $CX_6C$ (SEQ ID NO: 26), $CX_7C$ (SEQ ID NO: 24), $CX_{10}C$ (SEQ ID NO: 30)) $CX_3CX_3CX_3C$ (SEQ ID NO: 25), $X_2CX_4CX$ (SEQ ID NO: 23), and $X_7$ (SEQ ID NO: 29), were prepared, where "C" indicates cysteine and "$X_N$" indicates the given number of individually selected amino acids. These libraries can display cyclic peptides when at least-two cysteine residues are present in the peptide.

The libraries containing the defined cysteine residues were generated using oligonucleotides constructed such that "C" was encoded by the codon TGT and "$X_N$" was encoded by NNK, where "N" is equal molar mixtures of A, C, G and T, and where "K" is equal molar mixtures of G and T. Thus, the peptide represented by $CX_6C$ (SEQ ID NO: 26) can be represented by an oligonucleotide having the sequence TGT $(NNK)_6$TGT (SEQ ID NO: 31). Oligonucleotides were made double stranded by 3 cycles of PCR amplification, purified and ligated to the nucleic acid encoding the gene III protein in the fuse 5 vector such that, upon expression, the peptide is present as a fusion protein at the N-terminus of the gene III protein.

The vectors were transfected by electroporation into MC1061 cells. Bacteria were cultured for 24 hr in the presence of 20 μg/ml tetracycline, then phage were collected from the supernatant by precipitation twice using polyethylene glycol. Each library contained about $10^{12}$ transducing units/ml (TU; individual recombinant phage).

B. In Vivo Panning of Phage:

For lung and pancreas, a mixture of phage libraries containing $10^{10}$ TU was diluted in 200 μl DMEM and injected into the tail vein of anesthetized BALB/c mice (2 month old; Harlan Sprague Dawley; San Diego Calif.); AVERTIN (0.017 ml/g) was used as anesthetic (Pasqualini and Ruoslahti, supra, 1996). After 1–4 minutes, mice were snap frozen in liquid nitrogen or, after about 5 minutes of phage circulation, the mice were perfused through the heart with 5–10 ml of DMEM (SIGMA; St. Louis Mo.). To recover the phage, the organs from the perfused mice or partially thawed organs from snap frozen mice were collected and weighed, then were homogenized in 1 ml DMEM-PI (DMEM containing protease inhibitors (PI); phenylmethyl sulfonyl fluoride (PMSF; 1 mM), aprotinin (20 μg/ml), leupeptin (1 μg/ml)).

Organ samples were washed 3 times with ice cold DMEM-PI containing 1% bovine serum albumin (BSA), then directly incubated with 1 ml K91-kan bacteria for 1 hr. Ten ml NZY medium containing 0.2 μg/ml tetracycline (NZY/tet) was added to the bacterial culture, the mixture was incubated in a 37° C. shaker for 1 hr, then 200 μl aliquots were plated in agar plates containing 40 μg/ml tetracycline (tet/agar).

For in vivo panning of skin, two month old BALB/c nude mice were used to avoid contamination by hair. The mice were injected intravenously with phage as described above and, after perfusion through the heart, the skin was removed in large sections and placed on an ice cold plate with the hypodermis facing up. The skin was scraped with a scalpel to remove mostly hypodermis, which was then processed for phage recovery as described below.

For in vivo panning of retina, two month old female Simonson Albino rats were used to provide larger tissue samples than mice. The rats were anesthetized with phenobarbital (50 mg/kg body weight), and, while under deep anesthesia, the abdominal cavity of the rats was opened and $10^{10}$ TU of a phage library was injected into the left ventricle of the heart through the diaphragm. After 2–5 minutes of phage circulation, the eyes were removed, then washed once in 70% EtOH and once in PBS. The anterior chamber, with cornea and lens, was removed and the retina was peeled from the remaining posterior chamber. The tissue was weighed, homogenized with a syringe bulb in 1 ml of ice cold DMEM containing protease inhibitors (1 mM PMSF, 20 μg/ml aprotinin and 1 μg/ml of leupeptin; all from SIGMA; St. Louis Mo.). The tissue was washed 3 times with 1 ml of DMEM and the phage were rescued as described below.

Approximately 250 to 300 individual bacterial colonies containing phage recovered from the various organs or tissues were grown for 16 hr in 5 ml NZY/tet. In some experiments, approximately 1000 individual bacteria containing phage were picked and the phage were amplified in 2 ml of NZY/tet or the entire plate containing phage was scraped, pooled and grown in bulk and processed for injection. Where phage were cultured separately, the cultures were pooled and the phage were injected into mice or rats as described above for a second round of in vivo panning. In some experiments, a third or fourth round of panning was performed. Phage DNA was purified from individual bacterial colonies obtained and the DNA sequences encoding the peptides expressed by selected phage were determined (see Koivunen et al., supra, 1994b).

EXAMPLE II

Characterization of Peptides that Home to a Selected Organ

This example demonstrates that an organ or tissue homing peptide of the invention selectively homes to a selected organ or tissue including an organ containing a component of the RES.

A. Lung is the Selected Organ

After two or three rounds of in vivo panning of mice injected with a cyclic $CX_3CX_3CX_3C$ (SEQ ID NO: 25) or a cyclic $CX_6C$ (SEQ ID NO: 26) phage display library, four peptides that homed to lung were identified. The peptide sequences CGFECVRQCPERC (SEQ ID NO: 1; GFE-1) and CGFELETC (SEQ ID NO: 2; GFE-2) appeared repeatedly in the lung and two peptide sequences from the $CX_6C$ (SEQ ID NO: 26) library CTLRDRNC (SEQ ID NO: 15) and CIGEVEVC (SEQ ID NO: 16) also were found to home to lung (see Table 2, below).

To determine the specificity of lung homing of the individual peptides identified, phage displaying the peptides were amplified individually, diluted to the same input titer and administered to mice. Following administration, control kidney and brain organ was removed and the number of TU of phage in lung, kidney and brain was determined. The results shown in FIG. 2 reveal that 10× and 35× more phage having the peptide sequence CGFECVRQCPERC (SEQ ID NO: 1; GFE-1) bound to lung than to kidney and brain, respectively. FIG. 2 also reveals that CGFELETC (SEQ ID NO: 2; GFE-2) was found in lung at a 12× and 20× greater level than in kidney and brain, respectively. The lung homing peptides CGFECVRQCPERC (SEQ ID NO: 1; GFE-1), CGFELETC (SEQ ID NO: 2; GFE-2), CTLRDRNC (SEQ ID NO: 15) and CIGEVEVC (SEQ ID NO: 16) are enriched in lung at 35×, 9×, 6× and 5×, respectively, over unselected phage (see FIG. 2). Thus, substantial enrichment of phage binding to the lung was observed in comparison to control brain and kidney and in comparison to unselected phage.

Figure 3A:
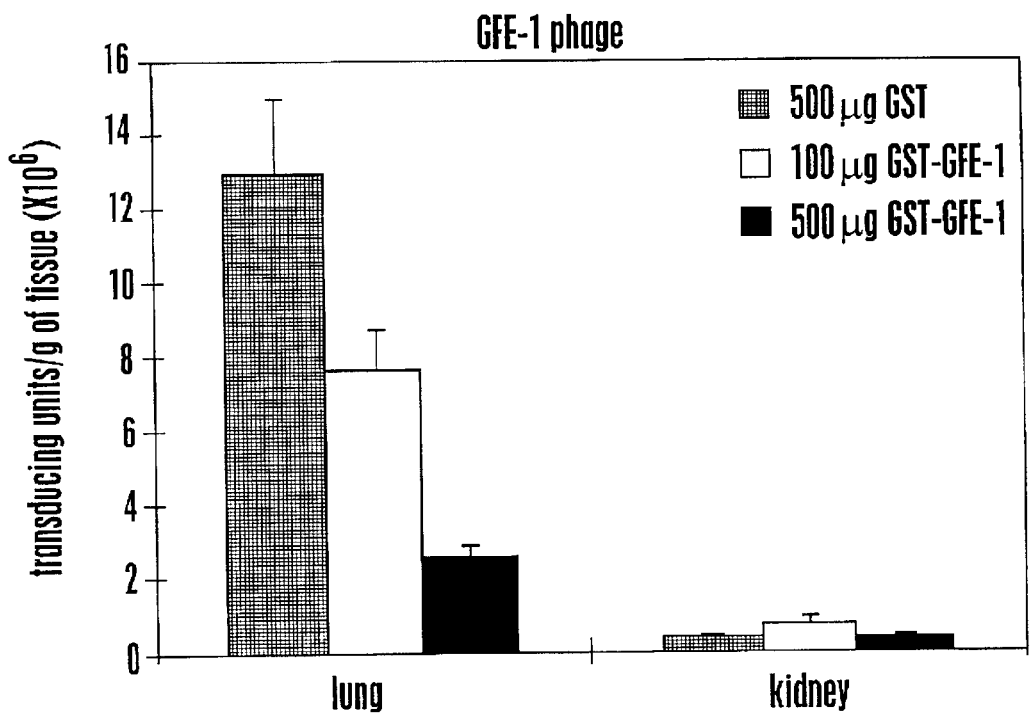
FIGS. 3A and 3B show the effect of coadministration of glutathione S-transferase—(GST)—fusion proteins on the homing of phage displaying lung or skin homing peptides.

Specificity for the lung homing peptides was also determined by competition experiments with GST-fusion peptides. A GST-GFE-1 (SEQ ID NO: 1) fusion peptide coadministered with GFE-1 (SEQ ID NO: 1) inhibited GFE-1 (SEQ ID NO: 1) homing to the lung, whereas GST had no effect on homing (FIG. 3A). In addition, the inhibitory effect of the GST-GFE-1 (SEQ ID NO: 1) on homing was dose dependent; 70% inhibition of homing occurred when injecting 500 μg of the GST-GFE-1 (SEQ ID NO: 1) fusion protein (FIG. 3B).

Figure 3B:
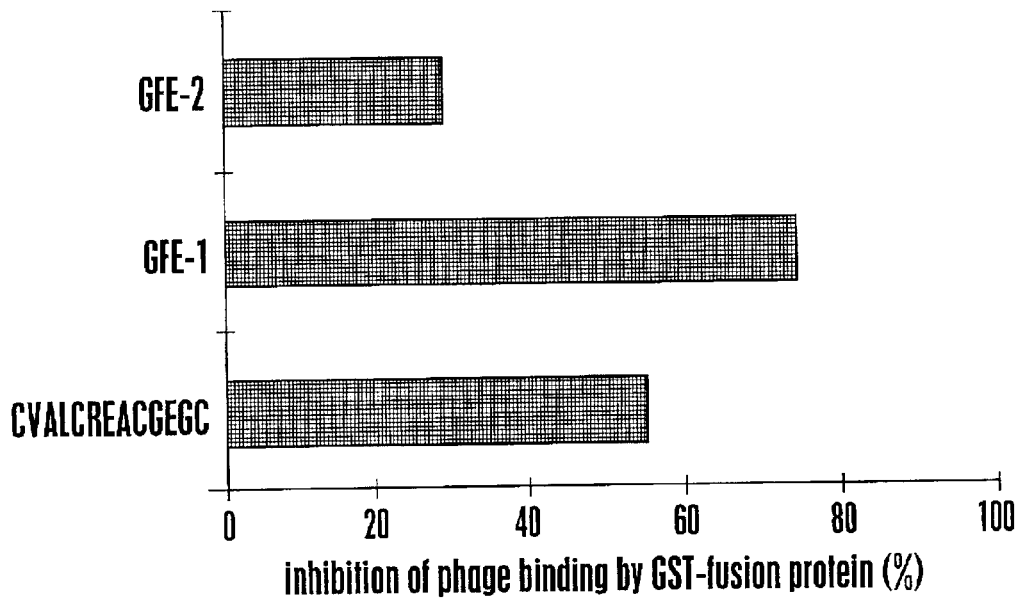

Coinjection of GST-GFE-2 (SEQ ID NO: 2) with GFE-2 (SEQ ID NO: 2) inhibited homing to a lesser extent; 30% inhibition of homing occurred when injecting 500 μg of the GST-GFE-2 (SEQ ID NO: 2) fusion protein (FIG. 3B). Interestingly, the GST-GFE-1 (SEQ ID NO: 1) fusion was more efficient at inhibiting GFE-2 (SEQ ID NO: 2) homing to the lung; 60% inhibition of GFE-2 (SEQ ID NO: 2) homing occurred when injecting 500 μg of the GST-GFE-1 (SEQ ID NO: 1) fusion protein (FIG. 3B). However, no inhibitory effect of GFE-1 (SEQ ID NO: 1) homing was observed when coinjecting GST-GFE-2 (SEQ ID NO: 2). This can be explained by GFE-1 (SEQ ID NO: 1) having a higher affinity for a shared target molecule than GFE-2 (SEQ ID NO: 2).

Additional lung homing peptides were obtained and the amino acid sequences were determined for the inserts (see Table 2). Peptides containing a GFE motif predominated (see Table 1; SEQ ID NOS: 1 and 2). Other peptides that were present more than once in lung are indicated by an asterisk in Table 2 (below), and the remaining peptides were identified one time each.

These results indicate that the selection of the peptides containing the GFE motif represents the selective binding of several independent phage displaying peptides having the GFE sequence and is not an artifact due, for example, to phage amplification. In addition, in some cases, phage that expressed peptides having the same amino acid sequence were encoded by oligonucleotides having different sequences, therefore confirming that homing of a particular phage to a lung is due to the specific peptide expressed on the phage.

These results demonstrate that in vivo panning can be used to screen phage display libraries in order to identify phage expressing peptides that home to lung, which contain a component of the RES.

B. Skin is the Selected Tissue:

in After two or three rounds of in vivo panning of mice injected with a cyclic $CX_3CX_3CX_3C$ (SEQ ID NO: 25) phage display library, the peptide sequence CVALCREACGEGC (SEQ ID NO: 3), which appeared repeatedly in skin, was identified (Table 1). To determine the specificity of skin homing of the sequence CVALCREACGEGC (SEQ ID NO: 3), phage displaying the peptide was amplified individually, diluted to the same input titer and administered to mice. Following administration, control kidney and brain organ were removed and the number of TU of phage in skin, kidney and brain was determined.

The results revealed that 7× more phage displaying the peptide sequence CVALCREACGEGC (SEQ ID NO: 3) bound to skin than to kidney or brain (see FIG. 2; Table 1). The peptide CVALCREACGEGC (SEQ ID NO: 3) was enriched in skin 7× over unselected phage (FIG. 2). Thus, substantial enrichment of phage binding to the skin was observed in comparison to control brain and kidney and in comparison to unselected phage.

Additional skin homing peptides were obtained by screening the cyclic $CX_3CX_3CX_3C$ (SEQ ID NO: 25) or $CX_{10}C$ (SEQ ID NO: 30) phage display libraries; amino acid sequences were determined for the inserts as shown in Table 5, below. Peptides that were identified more than one time during screening are indicated by an asterisk. For example, 14% of recovered $CX_3CX_3CX_3C$ (SEQ ID NO: 25) phage that homed to head skin had the sequence CVDVCCDGCPVCC (SEQ ID NO: 437). Phage having the sequence RVPLSGDVEH (SEQ ID NO: 438), LRVMSFTSGQ (SEQ ID NO: 439), or RFSVGSLFGS (SEQ ID NO: 440) each constituted 14% of recovered $CX_{10}C$ (SEQ ID NO: 30) phage that homed to head skin. Screening against homing to tail skin revealed that 12% of recovered $CX_3CX_3CX_3C$ (SEQ ID NO: 25) phage had the sequence CGATCEMQCPSGC (SEQ ID NO: 441).

Specificity for the skin homing peptides was also determined by competition experiments with GST-fusion peptides. FIG. 3B shows that a GST-CVALCREACGEGC (SEQ ID NO: 3) fusion peptide coadministered with CVALCREACGEGC (SEQ ID NO: 3) inhibited homing to the skin, whereas GST had no effect on homing. The inhibitory effect of the GST-GFE-1 on homing was about 55% when injecting 500 μg of the GST-CVALCREACGEGC (SEQ ID NO: 3) fusion protein (FIG. 3B).

These results demonstrate that in vivo panning can be used to screen phage display libraries in order to identify phage expressing peptides that home to skin and that such homing is specific.

C. Pancreas is the Selected Organ:

After two or three rounds of in vivo panning of mice injected with a cyclic $CX_7C$ (SEQ ID NO: 24) phage display library, various pancreas homing peptides were identified (Table 3). In particular, the peptide sequence SWCEPGWCR (SEQ ID NO: 4) appeared repeatedly in the pancreas. To determine the specificity of SWCEPGWCR (SEQ ID NO: 4), a phage displaying the sequence was amplified individually, diluted to the same input titer and administered to mice. Following administration, control brain organ was removed and the number of TU of phage in each pancreas and was determined. The results shown in FIG. 2, reveal that 10× more phage displaying the peptide sequence SWCEPGWCR (SEQ ID NO: 4) bound to pancreas than to brain and additional experiments revealed up to 20× enrichment in pancreas as compared to brain (Table 1). In addition, SWCEPGWCR (SEQ ID NO: 4) exhibited a 22× enrichment of phage to the pancreas as compared to unselected phage (see FIG. 2). Thus, substantial enrichment of phage binding to the pancreas was observed in comparison to control tissue (brain) and to unselected phage.

These results demonstrate that in vivo panning can be used to identify molecules that selectively home to pancreas. In addition, the results indicate that in vivo panning identifies independent phage encoding the same peptide.

D. Retina is the Selected Tissue

Rats injected with a cyclic $CX_7C$ (SEQ ID NO: 24) phage display library were subjected to in vivo panning and, after three rounds, the peptide sequences CSCFRDVCC (SEQ ID NO: 5) and CRDVVSVIC (SEQ ID NO: 6) were identified in retina. Because of small tissue sample size, the phage isolated could not be accurately quantitated. Thus, the selectivity of phage displaying the peptides was determined by individually amplifying the phage displaying the sequence and administering the phage to rats with a control phage fdAMPLAY88. This fd-ampicillin phage is similar to fd-tetracycline (fuse 5-based) in that it has the same infectivity.

Rats were injected with an equal amount of the CSCFRDVCC (SEQ ID NO: 5) or CRDVVSVIC (SEQ ID NO: 6) and the fdAMPLAY88 phage. Following administration, homing to retina was evaluated by comparing the number of TU of the selected phage on tetracycline plates and fdAMPLAY88 on ampicillin plates recovered from retina.

The results revealed that CSCFRDVCC (SEQ ID NO: 5) showed a 3× enrichment and CRDVVSVIC (SEQ ID NO: 6) showed a 2× enrichment in retina compared to control fdAMPLAY88 phage. Thus, substantial enrichment of phage binding to the retina was observed in comparison to control phage.

Additional retina homing peptides were obtained and the amino acid sequences were determined for the inserts (Table 6, below). Peptides that appeared more than one time are indicated. In particular, the RDV tripeptide motif was present in several different sequence contexts, indicating that the nucleic acids encoding the peptides were derived from a number of independent phage.

These results indicate that the selection of the peptides containing the RDV motif represents the selective binding of several independent phage displaying peptides having the RDV sequence and is not an artifact due, for example, to phage amplification. In addition, in some cases, phage that expressed peptides having the same amino acid sequence were encoded by oligonucleotides having different sequences, therefore confirming that homing of a particular phage to retina is due to the specific peptide expressed on the phage.

These results further demonstrate that the in vivo panning method is a generally applicable method for screening a library to identify, for example, phage expressing peptides that home to a selected organ or tissue, including organs and tissues containing a component of the RES. Database searches did not reveal any significant homology of the pancreas, lung, skin or retina homing peptides to known ligands for endothelial cell receptors.

EXAMPLE III

Immunohistologic Analysis of Lung, Pancreas and Skin Homing Peptides

This example demonstrates the localization of lung, pancreas and skin homing molecules using immunohistologic examination.

Phage displaying homing peptides were detected in lung, pancreas and skin by immunostaining histologic sections obtained 5 min after administration of phage expressing a lung, pancreas or skin homing peptide ("peptide-phage") to a mouse. Following administration of the peptide-phage, mice were handled as described above and various organs, including lung, pancreas and skin, were removed and fixed in Bouin's solution (SIGMA). Histologic sections were prepared and reacted with anti-M13 (phage) antibodies (Pharmacia Biotech; see U.S. Pat. No. 5,622,699, supra, 1997; Pasqualini and Ruoslahti, supra, 1996). Visualization of the bound anti-M13 antibody was performed using a second antibody conjugated to peroxidase (SIGMA) according to the manufacturer's instructions.

Phage displaying the lung homing peptide, GFE-1 (SEQ ID NO: 1), were administered intravenously to mice and, after 5 minutes of circulation, the lung was isolated and processed as described above. Immunohistochemical staining of the alveolar capillaries was observed and no preference for any anatomical portion was detected. However, staining of bronchiolar walls and some larger blood vessels was absent. Mice injected with unselected phage did not exhibit lung staining, and no staining was observed in pancreas and skin after injection of GFE-1 (SEQ ID NO: 1).

Similar experiments were performed in pancreas using phage displaying the pancreas homing peptide, SWCEPGWCR (SEQ ID NO: 4). In these experiments, histological samples of the pancreas as well as control organs and tissues including lung and skin were prepared and examined by immunostaining as described above. The results revealed staining in the capillaries and larger blood vessels of the exocrine pancreas whereas little if any staining of the endocrine pancreas was detected. Again, unselected phage did not stain pancreas, nor was any staining observed in lung and skin of mice injected with phage displaying SWCEPGWCR (SEQ ID NO: 4). Interestingly, some staining of blood vessels within the uterus was observed for the SWCEPGWCR (SEQ ID NO: 4) peptide. Moreover, after intravenous injection of phage displaying SWCEPGWCR (SEQ ID NO: 4), the phage was recovered from uterus at a 6× higher level in comparison to unselected phage. Thus, SWCEPGWCR (SEQ ID NO: 4) homes to both pancreas and uterus.

Experiments were performed in skin using phage displaying the skin homing peptide CVALCREACGEGC (SEQ ID NO: 3). In these experiments, histological samples from the skin as well as control organs and tissues including lung and pancreas were prepared and examined by immunostaining as described above. The results revealed staining in blood vessels of the hypodermis whereas little if any staining of the dermis was detected. Again, unselected phage did not stain these blood vessels, and no staining was observed in control the lung and pancreas of mice injected with phage displaying CVALCREACGEGC (SEQ ID NO: 3).

All phage, including unselected phage, caused staining of the liver and spleen. This result is consistent with the capture of phage by a component of the RES which was previously described.

These results demonstrate that lung, pancreas and skin homing peptides selectively home to lung, pancreas and skin, particularly to the vasculature. In addition, these results reveal that organs and tissues can exhibit differences of the staining patterns within particular regions, presumably reflecting the differential expression of a target molecule within the organ or tissue. Immunohistochemical analysis provides a convenient assay for identifying the localization and distribution of phage expressing lung, pancreas and skin homing peptides.

EXAMPLE IV

The Receptor for the GTE-1 Lung Homing Peptide is Membrane Dipeptidase

This example demonstrates that the receptor for "GFE" containing peptides such as GFE-1 (SEQ ID NO: 1) is membrane dipeptidase. This example further demonstrates that GFE-1 (SEQ ID NO: 1) binds and inhibits membrane dipeptidase activity.

A. GFE-1 Phage Bind Selectively top Lung Primary Cells

As described above, CGFECVRQCPERC (SEQ ID NO: 1; GFE-1) phage bind to mouse lung vasculature when injected in vivo. A phage binding assay on lung primary cells was performed to determine if the specificity of CGFECVRQCPERC (SEQ ID NO: 1; GFE-1) phage binding to lung tissue in vivo could be reconstituted in vitro.

Phage binding to primary cells was performed as follows. Briefly, Balb/c mice (Harlan Sprague Dawley) were anesthetized with 0.017 ml/g of Avertin as described in Gardner et al., Lab. Animal Sci. 45:199–204 (1995), which is incorporated herein by reference. Under deep anesthesia, mice were perfused through the heart with 10 ml Dulbecco's modified Eagle's medium (DMEM; Irvine Scientific; Santa Ana, Calif.). The lungs, kidneys and brain were then collected, minced, placed in 2 ml of DMEM containing 0.5% BSA (Intergen; Purchase, N.Y.) and 0.5 µg/ml collagenase V (SIGMA) and incubated at 37° C. for 25 minutes. Following collagenase treatment, the tissue was forced through a 70 µM pore cell strainer (Becton Dickinson; Franklin Lake, N.J.). The filtered cells were washed once with 10 ml DMEM supplemented with 10% serum. The phage particles used in the binding assay were amplified and purified, and the phage-displayed inserts were sequenced as described in Smith and Scott, supra, 1993. To ensure an equal input of the different phage to be tested, phage were titered several times using K91Kan bacteria (Smith and Scott, supra, 1993).

For the binding reaction, $10^9$ transducing units (TU) of phage were incubated with $5 \times 10^6$ cells in 1 ml DMEM supplemented with 10% serum. The binding was performed at 4° C. for 2 hours with gentle agitation. After the binding reaction, the cells were washed four times with 1 ml of DMEM supplemented with 10% serum at room temperature for 5 to 10 minutes each time. The cells were centrifuged, and the cell pellet resuspended in 100 µl of DMEM and transferred to a new tube. The phage bound to the cells were rescued by adding 1 ml of K91Kan bacterial culture (Smith and Scott, supra, 1993) followed by incubation at room temperature for 30 minutes. The bacteria were then diluted in 10 ml of LB culture media supplemented with 0.2 µg/ml tetracycline, and incubated for another 30 minutes at room temperature. Serial dilutions of the bacterial culture were plated on LB plates containing 40 µg/ml tetracycline. Plates were incubated at 37° C. overnight before the colonies were counted (transducing units, TU).

The results of the phage binding assay on primary lung cells in vitro showed that primary lung cells bound about 60-fold more CGFECVRQCPERC (SEQ ID NO: 1; GFE-1) phage than insertless fd-tet phage. Binding of CGFECVRQCPERC (SEQ ID NO: 1; GFE-1) phage to kidney cells was also higher than fd-tet binding (t test, p<0.02) although this binding was much lower than the GFE-1 (SEQ ID NO: 1) binding on lung cells. In in vivo studies, no specific phage homing to kidney was detected when the GFE-1 (SEQ ID NO: 1) phage was injected intravenously. The GFE-1 (SEQ ID NO: 1) phage showed no specific binding to primary brain cells in vitro.

GFE-1 (SEQ ID NO: 1) phage binding to lung cells was inhibited by almost 70% in the presence of 150 µM GFE-1 (SEQ ID NO: 1) peptide, whereas the same concentration of a control peptide, GRGESP (SEQ ID NO: 442), had no effect. The non-specific binding of the insertless fd-tet phage was not affected by the presence of GFE-1 (SEQ ID NO: 1) or control peptides. These results demonstrate that the selective in vivo binding of the GFE-1 (SEQ ID NO: 1) peptide sequence to lung endothelium can be reconstituted in an in vitro assay on total lung primary cells and that whole lung cell extracts contain sufficient amounts of GFE-1 receptor for isolation.

B. The GFE-1 (SEQ ID NO: 1) Peptide Binds a 55 kDa Surface Protein

To detect only the cell surface molecules that bind to GFE-1 (SEQ ID NO: 1), mouse lung endothelial surface proteins were biotinylated in vivo, and a total lung extract prepared. The labeled extract was first fractionated on a GFE-1 (SEQ ID NO: 1) peptide affinity column; subsequently, the column was washed, and bound proteins were eluted with a GFE-1 (SEQ ID NO: 1) peptide solution.

In vivo biotinylation of endothelial cell surface proteins was performed as previously described in De La Fuente et al., Am. J. Physiol. 272: L461–L470-(1997), which is incorporated herein by reference, with several modifications. Briefly, Balb/c mice were anesthetized with Avertin and perfused slowly through the heart for 10 to 15 minutes with approximately 15 ml of PBS containing 0.5 mg/ml of sulfo-NHS-LC-biotin (Pierce; Rockford, Ill.). Well perfused lungs or control tissues such as brain were then collected and incubated on ice for 20 minutes. The tissues were then homogenized for preparation of extracts as described further below.

For preparation of extracts, mouse or rat lungs were first minced and then homogenized with a Brinkman homogenizer (Brinkman; Wesbury, N.Y.) in a minimal volume (2.5 ml/g of tissue) of cold PBS containing 100 mM N-octyl-β-D-glucopyranoside (Calbiochem; La Jolla, Calif.) with 1 mM phenylmethylsulfonyl fluoride (PMSF), 20 µg/ml aprotinin and 1 µg/ml leupeptin (PBS/octylglucoside). The homogenized tissue was incubated on ice for 2 hours, and then centrifuged at 12,000×g for 30 minutes to remove cell debris. The pooled supernatants were cleared of any debris prior to affinity chromatogaphy.

GFE-1 (SEQ ID NO: 1) affinity chromatography was performed according to the general principles established by Pytela et al. for the isolation of integrins by RGD peptide chromatography (Pytela et al., Cell 40:191–198 (1985); Pytela et al., Methods Enzym. 144:475–489 (1987), each of which is incorporated herein by reference). All steps were performed at 4° C. Briefly, GFE-1 (SEQ ID NO: 1) or control peptides (AnaSpec; San Jose, Calif.) were coupled to CNBr-activated Sepharose 4B according to the manufacturer's instructions (Pharmacia Biotech; Uppsala, Sweden). The matrix contained approximately 2 mg/ml of peptide. The biotin-labeled extract from 2 mouse lungs was applied to 500 µl of the affinity matrix equilibrated in column buffer (PBS containing 50 mM octylglucoside and 1 mM PMSF). The extract was applied to the column, and the flow-through re-applied over a period of 90 minutes. The column was then washed with 20 volumes of column buffer. Elution with the synthetic GFE-1 (SEQ ID NO: 1) peptide was carried out by slowly washing the column over a period of 1 hour with 2 volumes of column buffer supplemented with 1 mg/ml of GFE-1 peptide (SEQ ID NO: 1). The remaining proteins bound to the column were eluted with 8 M urea.

Eluates were concentrated 5-fold using a Centricon 10,000 MWCO column (Amicon; Beverly, Mass.). Aliquots of each elution were then separated by SDS-PAGE using pre-cast polyacrylamide 4–12% gels (Novex; San Diego, Calif.). For the experiments done with biotin-labeled extracts, the proteins were transferred to a PVDF membrane (Millipore; Bedford, Mass.), blotted with streptavidin-HRP (Pierce; Rockford, Ill.) and developed with the ECL chemiluminescence system (NEN; Boston, Mass.).

Figure 4B:
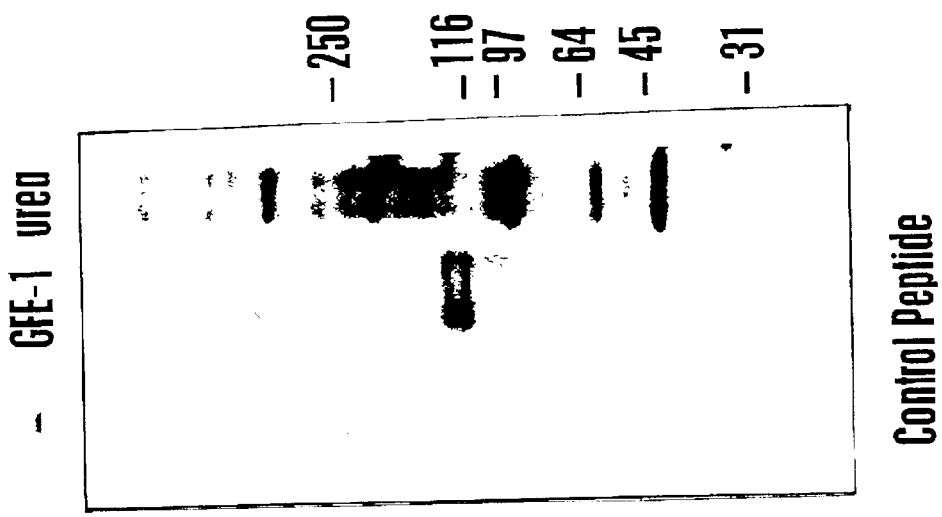
FIG. 4 shows that a 55 kDa cell surface protein from lung extracts specifically binds to a GFE-1 peptide affinity column. An in vivo biotinylated lung extract was fractionated on a CGFECVRQCPERC (SEQ ID NO: 1; GFE-1) peptide column or on a control peptide column (GRGESP; SEQ ID NO: 442), washed, and eluted with GFE-1 peptide. Aliquots (30 µl) from the wash fraction ("–"), GFE-1 peptide elution, and 8M urea elution were resolved by SDS-PAGE under reducing conditions. Molecular weight markers (in kDa) are indicated on the right side of each panel.
Figure 4A:
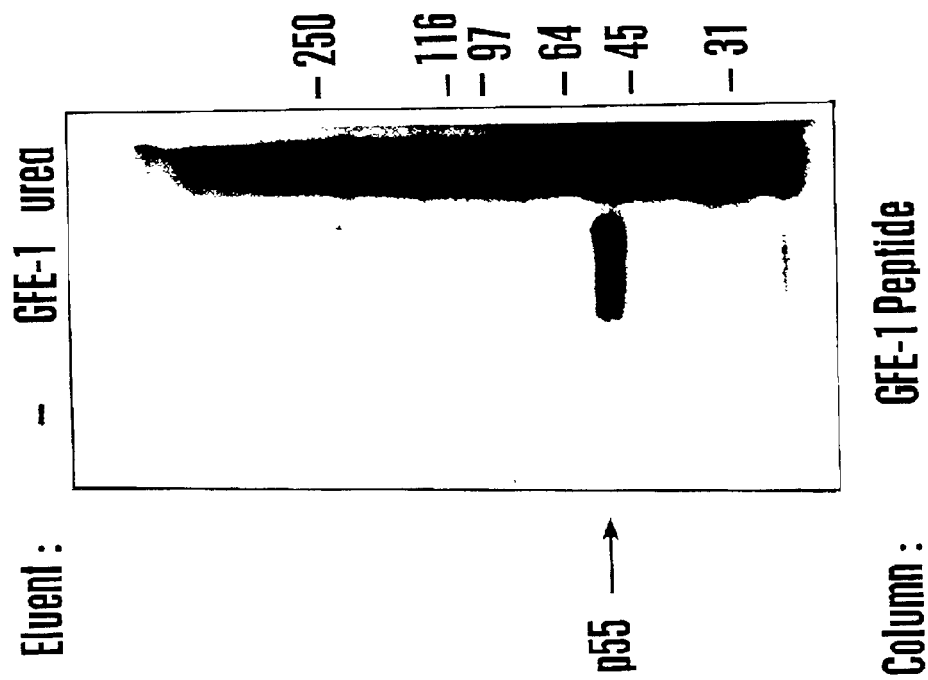

As shown in FIG. 4 (left panel), a 55 kDa biotinylated protein was selectively eluted by GFE-1 (SEQ ID NO: 1). Prior to elution, the washes from the column showed no detectable biotinylated proteins; subsequent addition of 8 M urea eluted many biotinylated proteins that were retained non-specifically in the column. No proteins in the 55 kDa range were detected after performing the same procedure on a control peptide (GRGESP; SEQ ID NO: 442) column (FIG. 4; right panel). As an additional control, an in vivo biotinylated brain cell extract was fractionated through a GFE-1 (SEQ ID NO: 1) peptide column under the same conditions; no biotinylated proteins from the brain extract specifically bound to the GFE-1 (SEQ ID NO: 1) peptide column (data not shown).

These results indicate that GFE-1 peptide (SEQ ID NO: 1) specifically binds to a 55 kDa lung vascular surface protein. Under non-reducing conditions, the 55 kDa protein migrated as a 110 kDa band (data not shown). Thus, these results further indicate that the GFE receptor is a disulfide-linked homodimer.

C. The 55 kDa GFE-1 (SEQ ID NO: 1) Receptor is Membrane Dipeptidase

GFE-1 (SEQ ID NO: 1) phage can selectively target rat lung blood vessels when injected in the circulation. To purify a larger amount of the 55 kDa protein than could be obtained from mouse tissues, a non-biotinylated extract was prepared from 100 frozen rat lungs (Pel-Freez Biologicals; Rogers, Ariz.). The large scale extract was prepared essentially as described above with the addition of a second extraction of the pellet with a minimal volume of PBS/octylglucoside.

The large scale extract was fractionated on a GFE-1 (SEQ ID NO: 1) peptide affinity column as described above using 3 ml of affinity matrix. A 55 kDa protein that was detectable by Coomassie blue staining was eluted from the column by GFE-1 peptide SEQ ID NO: 1 (data not shown). This protein, which co-migrated with the 55 kDa surface protein isolated from mouse lung, was subjected to tryptic digestion and sequenced by mass spectrometry at the Harvard University Microchemistry Facility (Boston, Mass.) by microcapillary reverse phase HPLC tandem mass spectrometry ($\mu$LC/MS/MS) on a Finnigan LCQ quadrupole ion trap mass spectrometer.

Two tryptic peptides derived from the 55 kDa protein, YPDLIAELLR (SEQ ID NO: 444) and TTPVIDGHNDLP-WQMLTLFNNQLR (SEQ ID NO: 445), showed complete identity with rat membrane dipeptidase (EC 3.4.13.19), also known as microsomal dipeptidase, dehydropeptidase-1 or MDP. Several other peptides sequences indicated the presence of rat IgG in the sample. Contamination of the sample with IgG is expected in this molecular weight range, given the abundance of IgG in an extract from unperfused lungs.

To confirm that membrane dipeptidase (MDP) is the GFE-1 (SEQ ID NO: 1) peptide binding protein, the 55 kDa protein was assayed for membrane dipeptidase activity. Samples from the affinity chromatography wash fraction and the GFE-1 (SEQ ID NO: 1) peptide eluate (FIG. 4) were incubated in the presence of the specific MDP substrate Gly-D-Phe, and D-Phe detected fluorimetrically exactly as described in Heywood and Hooper, supra, 1995 (see, also, Keynan et al., supra, 1996). Briefly, the samples were first incubated at 37° C. for 3 hours with the MDP substrate Gly-D-Phe (1 mM; SIGMA). The released D-Phe was then converted to 6,6'-dihydroxy-[1,1'-biphenyl]-3,3'-diacetic acid in the presence of D-amino acid oxydase (Type I; SIGMA) and peroxidase (Type VI; SIGMA; Heywood and Hooper, supra, 1995). Fluorescence was measured using an fmax fluorescence microplate reader from Molecular Devices (Sunnyvale, Calif.).

Figure 5:
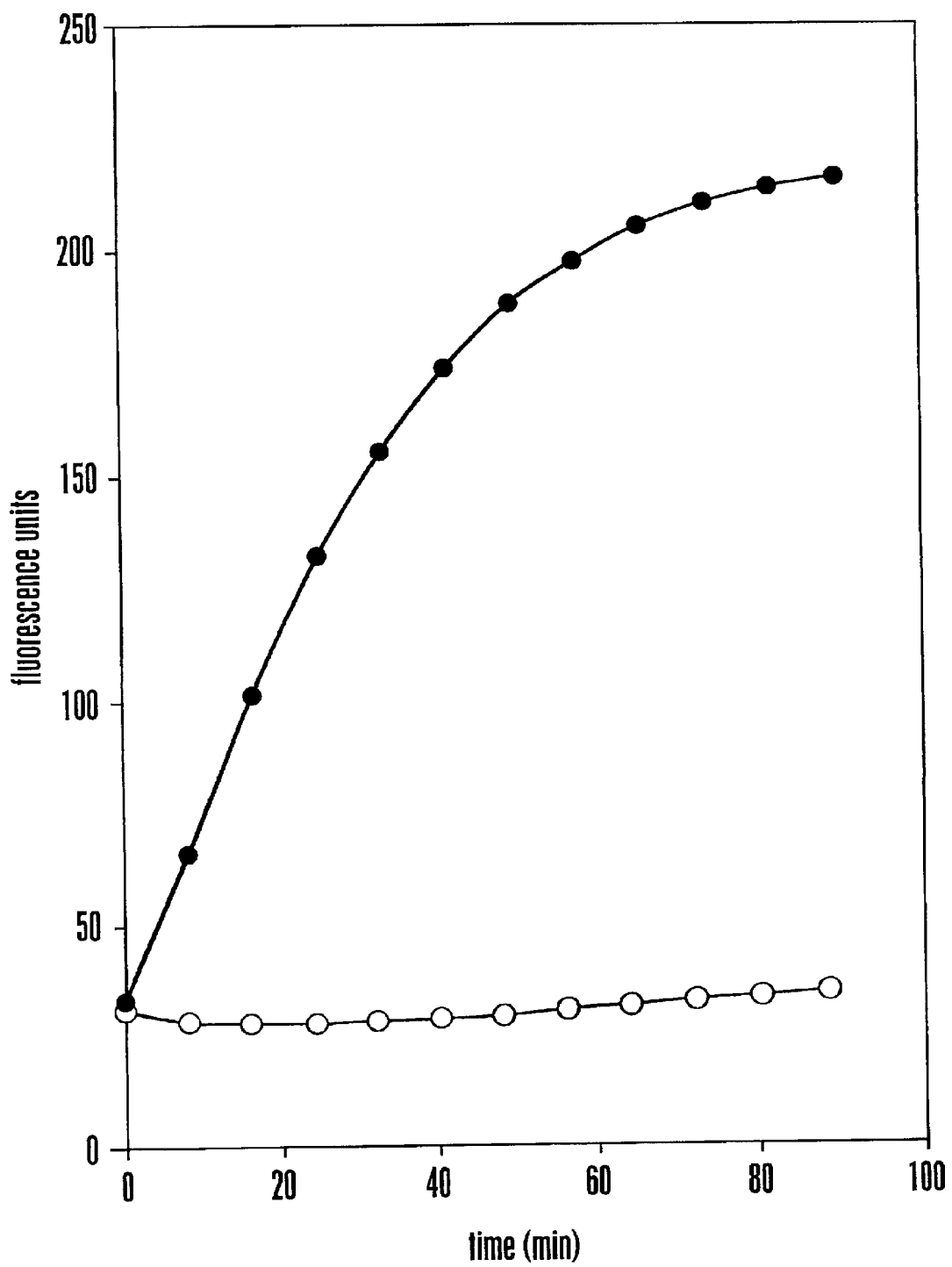
FIG. 5 shows a time course of the fluorimetric detection of D-phenylalanine (D-Phe) produced by hydrolysis of Gly-D-Phe. Samples from the wash fraction (○) and the CGFECVRQCPERC (SEQ ID NO: 1; GFE-1) peptide eluate (●) from a GEE-1 peptide affinity column were assayed for MDP activity with a Gly-D-Phe substrate. The time-dependent conversion of D-Phe into a fluorescent compound is shown.

FIG. 5 shows a time course of the conversion of D-Phe into a fluorescent compound in samples from the affinity chromatography wash fraction and GFE-1 peptide eluate described above (FIG. 4). While the wash fraction showed only a baseline level of fluorescence, the GFE-1 (SEQ ID NO: 1) peptide eluate contained high membrane dipeptidase activity as illustrated by the time-dependent conversion of D-Phe (see FIG. 5). In addition, GFE-1 (SEQ ID NO: 1) peptide eluate isolated from the rat lung extract also showed strong MDP activity (data not shown). MDP activity also was detected in the total lung extract, although the specific activity was about 600-fold higher for the GFE-1 peptide (SEQ ID NO: 1) eluate (200 nmol D-Phe/min/mg) than for the total rat lung extract (0.34 nmol D-Phe/min/mg).

D. GFE-1 (SEQ ID NO: 1) and GFE-2 (SEQ ID NO: 2) Phage Bind to Cells Transfected with MDP The COS-1 cell line, which is known to have low or no detectable level of MDP activity, has been used extensively to study MDP structure and function (Keynan et al., supra, 1996; Keynan et al., *Biochem, J.* 326:47–51 (1997)). COS-1 cells were trasfected with murine MDP and used to assay binding to SEQ ID NOS: 1 and 2 as described below.

For transfection into COS-1 cells, a murine MDP expression vector was prepared as follows. Total mouse lung RNA was isolated using Qiagen RNA purification columns (Qiagen; Santa Clarita, Calif.) and used as a template for first strand cDNA synthesis with reverse transcriptase and a mixture of random hexamers and poly-dT oligonucleotides (GIBCO/BRL; Grand Island, N.Y.). Mouse MDP cDNA (Pasqualini et al., J. Cell Biol. 130:1189–1196 (1995)) was amplified from the cDNA pool by PCR using the oligonucleotide pair: CCGCTGGTACCGCAGATCCCTGGG-GACCTTG (SEQ ID NO: 446), which contains a KpnI adaptor, and TCTTTCTAGAGCTCAGAGAGCACTG-GAGGAG (SEQ ID NO: 447), which contains an XbaI adaptor, using Taq polymerase from GIBCO/BRL. The amplified 1.3 kb murine MDP cDNA was digested with KpnI and XbaI, and inserted into the same sites of the pcDNA3 expression vector (Invitrogen; Carlsbad, Calif.) using DNA restriction enzymes and T4 DNA ligase from New England Biolabs (Beverly, Mass.). Successful cloning of the murine MDP cDNA was confirmed by DNA sequencing. Transfection of the COS-1 cells was performed with the Superfect Reagent from Qiagen as recommended by the manufacturer.

Phage binding to COS-1 cells transfected with MDP was determined as follows. Briefly, $10^7$ COS-1 cells were transfected with 10 $\mu$g of either the MDP expression vector or the vector alone. After 48 hours, cells were scraped gently from the dish, washed once, and subjected to the phage binding assay or membrane dipeptidase activity assay described above. For the phage binding assay, $5 \times 10^6$ cells and $10^{10}$ transducing units (TU) of phage input were used. For measurement of membrane dipeptidase activity, $10^6$ cells were lysed in 100 $\mu$l of PBS/octylglycoside without protease inhibitors. A 10 $\mu$l aliquot of the extract was used to measure MDP activity.

Figure 6A:
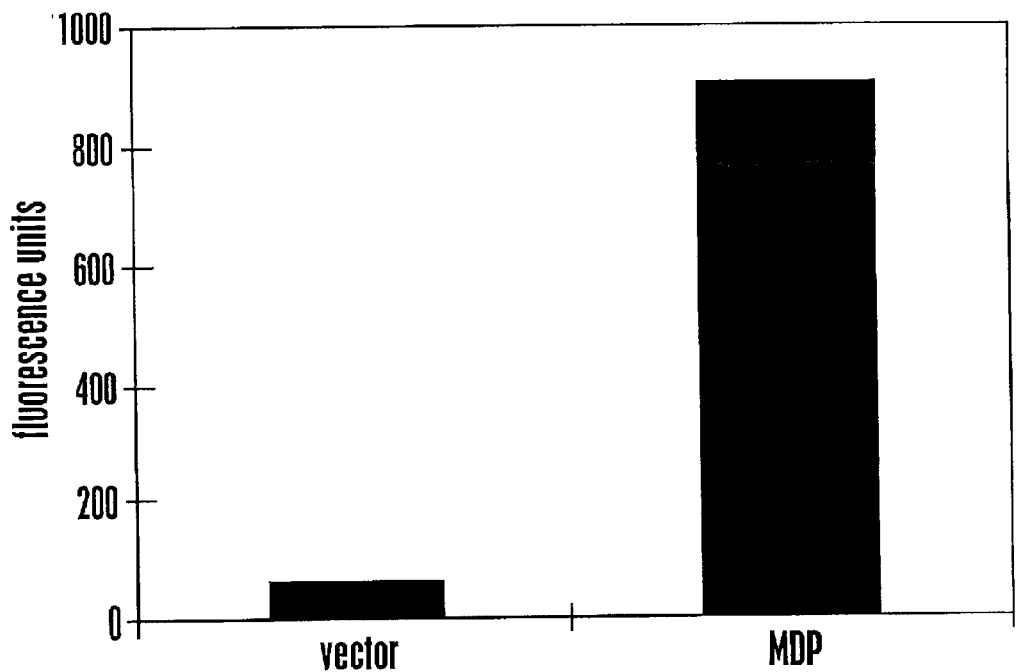
In FIG. 6A, COS-1 cells were transfected with the MDP expression vector or vector alone. Two days after the transfection, cell extracts were prepared and analyzed for MDP activity.
Figure 6B:
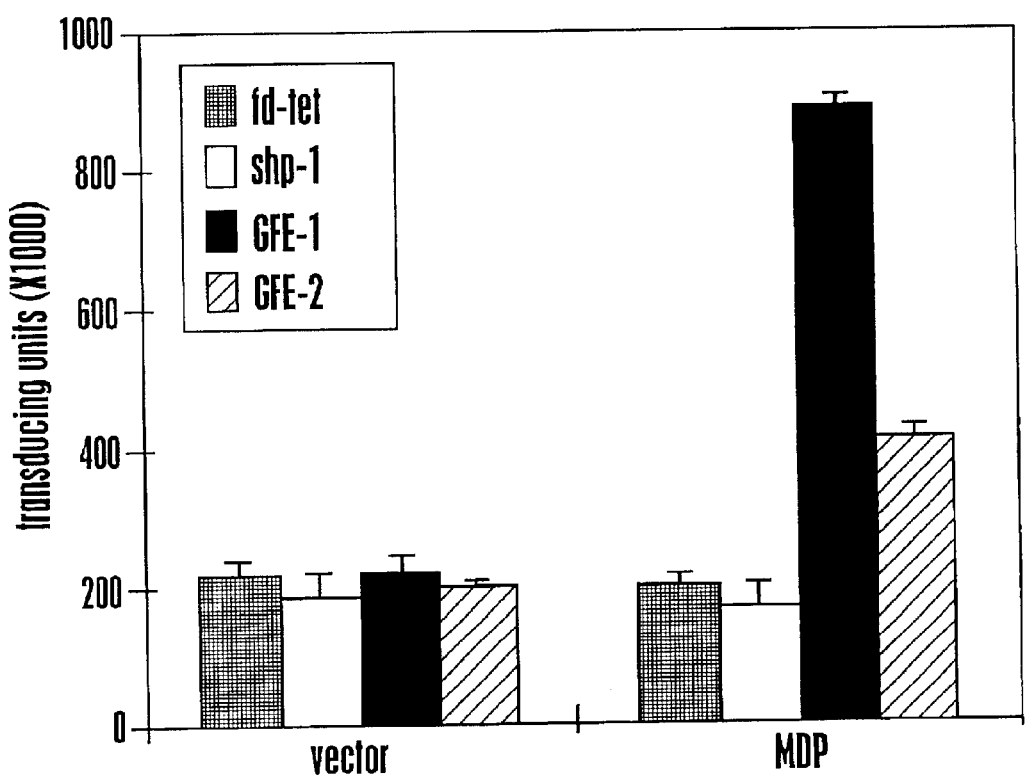
In FIG. 6B, COS-1 cells transfected with either the MDP expression vector or control empty vector were subjected to a binding assay in the presence of equal amounts of either control phage (fd-tet) or phage bearing the skin-homing peptide CVALCREACGEGC (SEQ ID NO: 3; "shp-1"), CGFECVRQCPERC (SEQ ID NO: 1; GFE-1) peptide, or CGFELETC (SEQ ID NO: 2; GFE-2) peptide. In each case, the total number of phage transducing units rescued from these cells is shown. Error bars indicate standard deviation of the mean from triplicate platings.

As shown in FIG. 6A, COS-1 cells transfected with murine MDP showed at least 15-fold higher MDP activity than mock transfected cells. Furthermore, GFE-1 (SEQ ID NO: 1) phage bound COS-1 cells transfected with MDP. As shown in FIG. 6B, the GFE-1 (SEQ ID NO: 1) phage bound 4-fold more to MDP transfected cells than to mock transfected cells. Negative control phage, the fd-tet phage and a skin-homing phage (CVALCREACGEGC; SEQ ID NO: 3)

displaying a peptide with structural features similar to those of the GFE-1 (SEQ ID NO: 1) peptide, showed no specific binding to cells expressing MDP as compared to mock transfected cells. In addition, FIG. 6B shows that GFE-2 (SEQ ID NO: 2) phage also bound MDP transfected cells; the binding was weaker than the GFE-1 (SEQ ID NO: 1) binding in agreement with the in vivo lung homing data described above. The binding of both GFE-1 (SEQ ID NO: 1) and GFE-2 (SEQ ID NO: 2) phage to MDP-transfected cells was completely inhibited by GFE-1 peptide (SEQ ID NO: 1; data not shown). These results indicate that the GFE-1 (SEQ ID NO: 1) and GFE-2 (SEQ ID NO: 2) peptides bind the same receptor.

E. GFE-1 (SEQ ID NO: 1) can Inhibit MDP Activity

The metabolism of the tripeptide glutathione involves cleavage of the tripeptide by γ-glutamyl transpeptidase to form glutamate and cysteinylglycine (Cys-Gly). The dipeptide Cys-Gly is subsequently recognized and cleaved by MDP, which cleaves only dipeptides. The amino acid sequence of glutathione is similar to the N-terminal portion of the GFE-1 peptide CGFECVRQCPERC (SEQ ID NO: 1), with the first two first amino acids of GFE-1 being Cys-Gly.

GFE-1 (SEQ ID NO: 1) was assayed for the ability to inhibit hydrolysis of Gly-D-Phe by MDP. Fluorimetric detection of D-Phe was performed as described above. FIG. 7 shows that GFE-1 (SEQ ID NO: 1) inhibited hydrolysis of the Gly-D-Phe substrate (0.5 mM) in a dose-dependent manner. A control cyclic peptide (CARAC; SEQ ID NO: 443) did not inhibit the enzyme.

These results indicate that GFE-1 (SEQ ID NO: 1) can act as a competitive inhibitor of MDP activity.

EXAMPLE V

GFE-1 (SEQ ID NO: 1) Inhibits Lung Metastasis

This example demonstrates that the GFE-1 peptide SEQ ID NO: 1 can inhibit experimental lung metastasis in mice.

Experimental lung metastasis was induced in mice using C8161 human melanoma cells essentially as described in Arap et al., Science 279:377–380 (1998) and Pasqualini et al., Nature Med. 11:1197–1203, each of which is incorporated herein by reference. Briefly, C8161 cells were cultured to 75% confluence and then collected with 2.5 mM EDTA/PBS. The C8161 cancer cells were injected into the tail vein of female nude BALB/c mice (two months old) at a concentration of $10^5$ cells per animal. Two sets of five mice were injected with the cells alone; cells with 250 μg control CARAC peptide (SEQ ID NO: 443) or cells with 250 μg GFE-1 peptide (SEQ ID NO: 1). Each injection was in a total volume of 200 μl.

Aliquots of the melanoma cells and peptide mixture were cultured overnight to confirm that the peptides do not affect viability of the tumor cells. Neither the GFE-1 (SEQ ID NO: 1) or CARAC (SEQ ID NO: 443) peptides exhibited toxicity to the melanoma cells (data not shown).

Figure 8:
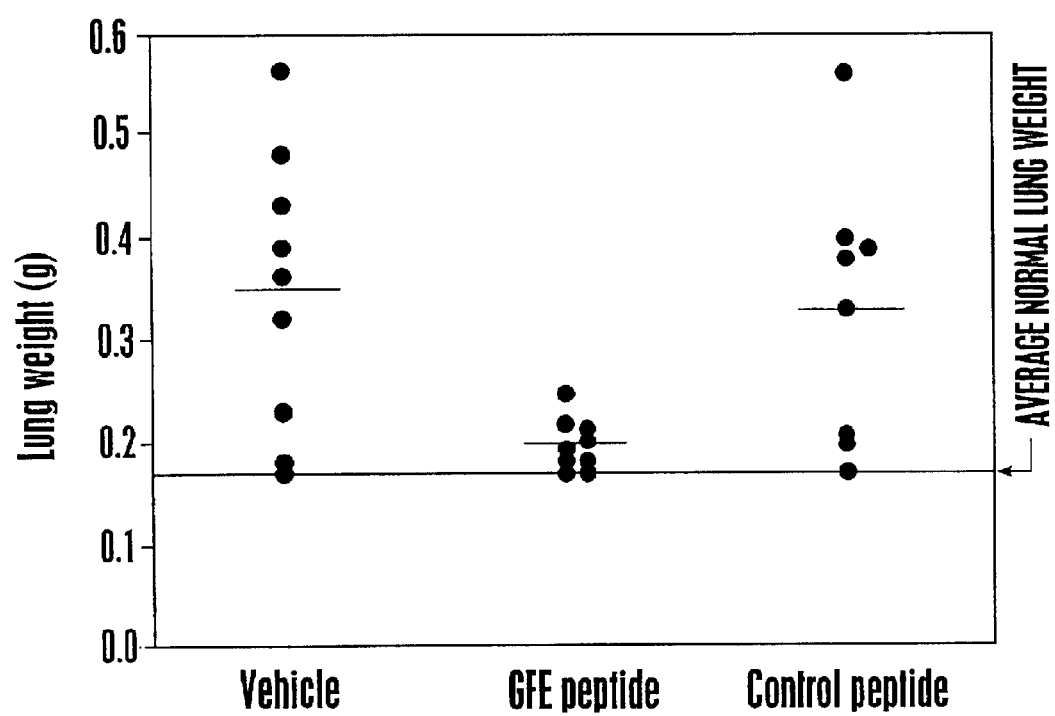
FIG. 8 shows that GFE-1 (SEQ ID NO: 1) inhibits lung metastasis of human melanoma cells. Lung weight is shown for mice five weeks after injection with $10^5$ C8161 human melanoma cells alone ("vehicle"); $10^5$ C8161 cells coadministered with 250 µg GFE-1 peptide SEQ ID NO: 1 ("GFE-1 peptide"); or $10^5$ C8161 cells coadministered with 250 µg CARAC peptide SEQ ID NO: 443 ("control peptide").

Mice were sacrificed five weeks after injection, and the lungs collected and weighed. As shown in FIG. 8, the lung weight of mice administered GFE-1 (SEQ ID NO: 1) peptide was significantly less than the lung weight seen in mice administered melanoma cells alone ("vehicle") or melanoma cells with control peptide CARAC SEQ ID NO: 443 ("control peptide"). These results indicate that GFE-1 can inhibit lung metastasis of human cancer cells.

A similar lung metastasis experiment was performed using a GFE-1 (SEQ ID NO: 1) glutathione S-transferase fusion protein prepared as described in Rajotte et al., J. Clinical Invest. 102:430–437 (1998), which is incorporated herein by reference. The GFE-1 (SEQ ID NO: 1) glutathione S-transferase fusion protein inhibited the increase in lung weight resulting from injection of C8161 human melanoma cells in a manner similar to the results observed with peptide SEQ ID NO: 1 as shown in FIG. 8.

These results indicate that GFE-1 (SEQ ID NO: 1) can inhibit lung metastasis and that MDP serves as a receptor for metastasizing tumor cells on lung vasculature.

EXAMPLE VI

Preparation of Z-2-Acylamino-3-monosubstituted Propenoate MDP-binding Homing Molecules This example demonstrates several methods for preparation of MDP-binding molecules having Structure 1.

A. Method for Preparation of an MDP-binding Homing Molecule Having Structure 1

An MDP-binding homing molecule having Structure 1 is made by condensing directly the appropriate 2-keto acid and amide as follows:

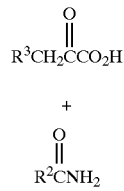

wherein $R^2$ and $R^3$ are as defined. The general reaction conditions involve mixing approximately 14:1 parts of the acid to the amide in an inert solvent such as toluene or methyl isovalerate and heating at reflux with azeotropic removal of water for 3–48 hours, preferably 5–24 hours. The solution when cooled normally yields the product in crystalline form. If desired, the product is isolated using a base extraction process. The product is recrystallized using generally known techniques.

An optional modification of this procedure requires an additional small amount of p-toluenesulfonic acid as catalyst during the reaction.

B. Method for Preparation of an MDP-binding Homing Molecule Having Structure 1

An MDP-binding homing molecule having Structure I is prepared using an α-amino acid, t-butyl ester in reaction with an acid chloride as follows:

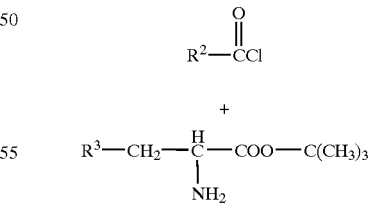

The reaction takes place in the presence of base, such as triethylamine, in a solvent such as methylene chloride. The resulting N-acylated product is then oxidized by treatment with t-butyl hypochlorite followed by addition of sodium methoxide. This yields the 2-methoxy derivative or its elimination product, the α,β-unsaturated ester. Further treatment with anhydrous hydrochloric acid converts either the 2-methoxy derivative or the unsaturated ester (or the mixture of both) to the desired α,β-unsaturated free acid.

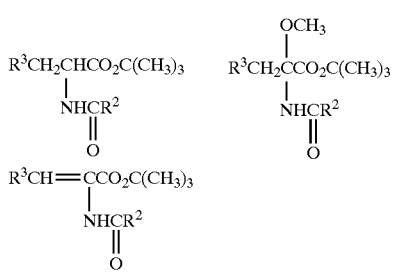

Some compounds in which $R^3$ has a terminal substituent which is an amino, quaternary nitrogen, thiol or carboxyl, derivative can be made most conveniently from an intermediate having a terminal bromine. In this case the intermediate has the structure

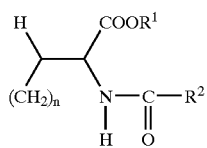

where n is the number of carbons in the desired hydrocarbon chain (e.g., from 3–7).

In order to prepare $R^3$ having a terminal trimethylammonium substituent, the bromo intermediate is reacted with trimethylamine; to yield the amino, the bromo intermediate is reacted with ammonia; the guanidino reaction is with guanidine; to prepare the thio derivatives, including 2-amino-2-carboxyethylthio, the bromo compound is reacted with cysteine HCl, or the appropriate mercaptan. Derivatized amino, such as formamidino, ureido, and acylamide (acetamido) are made from the compounds having an amino group by reacting with o-benzyl formimidate HCl, potassium cyanate and the appropriate acyl anhydride (acetic anhydride) respectively.

C. Method for Preparation of an MDP-binding Homing Molecule Having Structure 1

Another route for preparing compounds when $R^3$ is a terminally substituted thio derivative utilizes a chloroketo ester intermediate as follows:

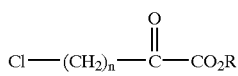

in reaction with the desired amide,

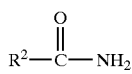

in toluene at reflux in the presence of a catalytic amount of p-toluenesulfonic acid. The resulting intermediate is hydrolyzed to the acid; the chloro group is then displaced in reaction with the appropriate mercaptan. This reaction is valuable since it permits use of the chiral amide, thereby preparing a functionalized side chain. Alternatively, the mixture of Z+E isomers prepared after the mercaptan condensation is directly isomerized into the Z form by adding acid to a pH of about 3, and heating to about 90° C. for 30 minutes. Only the Z form remains, and recovery is simple and straight-forward.

D. Preparation of Sodium Z-7-(L-amino-2-carboxyethylthio)-2-(2,2-dimethylcyclopropanecarboxamido)-2-heptenoic acid 1. Grignard Preparation of ethyl-7-chloro-2-oxoheptanoate Equimolar amounts (8 moles each) of I-bromo-5-chloropentane and magnesium are reacted in tetrahydroturan (THF) (960 ml) at 25° C. The flask is charged with the magnesium in the THF, and the bromochloropentane added over 1 hour, then aged 2 hours. After the reaction is judged complete, the reaction solution is added (cooled –15° C., to 16 moles of diethyloxalate in 1856 ml THF, while maintaining the temperature at 10 degrees C. 3N HCl is added to quench, keeping the temperature below 25° C. After stripping solvents, the calculated yield is 48.8% of the ethyl-1-chloro-6-oxoheptenoate.

2. Condensation and Hydrolysis

S-2,2-dimethylcyopropylcarboxamide (1017 g), 2143.6 g of ethyl-7-chloro-2-ketoheptanoate, 9 liters of toluene and 12 g of p-toluene sulfonic acid are charged to a 22 L flask, and heated to reflux with stirring. After 23 hours, liquid chromatography shows the expected product ratio, and 4 L of toluene are removed under slightly reduced pressure. The pot is charged with water, neutralized to pH 7 with 2 N NaOH, and vacuum distilled leaving a final pot volume of about 5 liters. This is hydrolyzed by adding 1760 g of 50% aqueous NaOH (4 liters water) and stirring overnight. The flask is charged with 4 L methylene chloride, and pH adjusted to 8.8 using HCl. Unreacted amide crystallizes out. The organic layers are separated from water, and then evaporated. The gummy residue is dissolved in 8 L water containing 720 q, 50% NaOH, and to this solution is charged 1818 g L-cysteine Hcl, $H_2O$, 2 kg ice, 2484 g 50% NaOH and 1 L water. The pH of this solution, after aging overnight at room temperature, is adjusted to 3.0 with concentrated HCl, and the resulting gummy suspension is heated to 95° C. to afford a clear solution. After 30 minutes, no E isomer is detected by 1c. After work-up and purification, the overall yield is 2060 g, 87% yield. This material is recrystallized from acetonitrile. 1500 g of the recrystallized material is dissolved in 6 L water and 910 ml 3.88 N NaOH, then neutralized to pH 7, and lyophilized to afford 1569 9 (98.6%) of the title compound. Analysis; Calcd,: C, 50.52; H, 6.62; N, 7.36; S, 8.43; Na, 6.04. Found: C, 50.71; H, 6.78; N, 7.49; S, 8.52; Na, 5.92.

All journal article, reference, and patent citations provided above, in parentheses or otherwise, whether previously stated or not, are incorporated herein by reference.

Although the invention has been described with reference to the examples provided above, it should be understood that various modifications can be made without departing from the spirit of the invention. Accordingly, the invention is limited only by the claims.

TABLE 2

| PEPTIDES FROM PHAGE RECOVERED FROM LUNG | |
|---|---|
| CIKGNVNC (32) | CRHESSSC (33) |
| CLYIDRRC (34) | CYSLGADC (35) |
| CSKLMMTC (349) | CGFELETC* (2) |
| CNSDVDLC (36) | CVGNLSMC* (37) |
| CEKKLLYC (38) | CKGQRDFC* (39) |
| CTFRNASC (40) | CNMGLTRC* (41) |
| CHEGYLTC* (42) | CGTFGARC (43) |
| CIGEVEVC* (16) | CRISAHPC (44) |
| CLRPYLNC* (45) | CSYPKILC (46) |
| CMELSKQC* (47) | CSEPSGTC (48) |

TABLE 2-continued
PEPTIDES FROM PHAGE RECOVERED FROM LUNG

| | |
|---|---|
| CGNETLRC (49) | CTLSNRFC (50) |
| CMGSEYWC (51) | CLFSDENC* (52) |
| CAHQHIQC (53) | CKGQGDWC (54) |
| CAQNMLCC (55) | CWRGDRKIC* (56) |
| CLAKENVVC* (13) | CIFREANVC (57) |
| CRTHGYQGC (58) | CERVVGSSC (59) |
| CKTNHMESC (60) | CYEEKSQSC (61) |
| CKDSAMTIC (62) | CTRSTNTGC (63) |
| CMSWDAVSC* (64) | CKWSRLHSC* (65) |
| CMSPQRSDC (66) | CLHSPRSKC (67) |
| CPQDIRRNC (68) | CLYTKEQRC (69) |
| CQTRNFAQC (70) | CTGHLSTDC (71) |
| CQDLNIMQC (72) | TRRTNNPLT (73) |
| CGYIDPNRISQC (74) | CTVNEAYKTRMC* (75) |
| CRLRSYGTLSLC* (76) | CAGTCATGCNGVC (77) |
| CADYDLALGLMC (78) | CPKARPAPQYKC (79) |
| CSSHQGGFQHGC (80) | CQETRTEGRKKC (81) |
| CRPWHNQAHTEC* (82) | CSFGTHDTEPHC (83) |
| CSEAASRMIGVC* (84) | CWEEHPSIKWWC* (85) |
| CWDADQIFGIKC (86) | CVDSQSMKGLVC (87) |
| CRLQTMGQGQSC (88) | CRPAQRDAGTSC (89) |
| CGGRDRGTYGPC (90) | CGEVASNERIQC (91) |
| CNSKSSAELEKC (92) | CVLNFKNQARDC (93) |
| CRGKPLANFEDC (94) | CEGHSMRGYGLC (95) |
| CRDRGDRMKSLC (96) | CDNTCTYGVDDC (97) |
| CSAHSQEMNVNC (98) | CGAACGVGCRGRC (99) |
| CGFECVRQCPERC* (1) | CLVGCRLSCGGEC (100) |
| CRSGCVEGCGGRC (101) | CIARCGGACGRHC (102) |
| CGGECGWECEVSC (103) | CGVGCPGLCGGAC* (104) |
| CKWLCLLLCAVAC (105) | CSEGCGPVCWPEC (106) |
| CGAACGVGCGGRC (107) | CSGSCRRGCGIDC (108) |
| CGASCALGCRAYC (109) | CDTSCENNCQGPC (110) |
| CSRQCRGACGQPC (111) | CYWWCDGVCALQC (112) |
| CAGGCAVRCGGTC (113) | CGGACGGVCTGGC* (114) |
| CGRPCVGECRMGC (115) | CLVGCEVGCSPAC (116) |
| CPRTCGAACASPC (117) | CRGDCGIGCRRLC (118) |
| CCFTNFDCYLGC (435) | |

Parentheses contain SEQ ID NO:.
*indicates sequences isolated more than once.

TABLE 3
PEPTIDES FROM PHAGE RECOVERED FROM PANCREAS

| | |
|---|---|
| EICQLGSCT (119) | WRCEGFNCQ (120) |
| RKCLRPDCG (121) | SWCEPGWCR* (4) |
| LACFVTGCL (122) | GLCNGATCM* (123) |
| DMCWLIGCG (124) | SGCRTMVCV (125) |
| QRCPRSFCL (126) | LSCAPVICG (127) |
| RECTNEICY (128) | NECLMISCR (129) |
| SCVFCDWLS (130) | WACEELSCF (131) |
| QNCPVTRCV (132) | CATLTNDEC (133) |
| CDNREMSC (134) | CFMDHSNC (135) |
| CGEYGREC (136) | CHMKRDRTC (137) |
| CKKRLLNVC (138) | CLDYHPKC (139) |
| CMTGRVTC (140) | CNKIVRRC (141) |
| CPDLLVAC (142) | CSDTQSIGC (143) |
| CSKAYDLAC (144) | CSKKGPSYC (145) |
| CTLKHTAMC (146) | CTQHIANC (147) |
| CTTEIDYC (148) | CVGRSGELC (149) |

Parentheses contain SEQ ID NO:.
*indicates sequences isolated more than once.

TABLE 4
PEPTIDES FROM PHAGE RECOVERED FROM GUT

| | |
|---|---|
| YAGFFLV* (150) | RSGARSS (151) |
| CVESTVA (152) | SRRQPLS* (153) |
| SKVWLLL (154) | QVRRVPE (155) |

TABLE 4-continued
PEPTIDES FROM PHAGE RECOVERED FROM GUT

| | |
|---|---|
| YSGKWGW* (156) | MVQSVG (157) |
| LRAVGRA (158) | MSPQLAT* (159) |
| GAVLPGE (160) | WIEEAER* (161) |
| LVSEQLR (162) | RGDRPPY (163) |
| VRRGSPQ (164) | RVRGPER (165) |
| GISAVLS* (166) | GGRGSWE (167) |
| GVSASDW (168) | FRVRGSP (169) |
| SRLSGGT (170) | WELVARS (171) |
| MRRDEQR (172) | GCRCWA (173) |
| LSPPYMW (7) | LCTAMTE (18) |

Parentheses contain SEQ ID NO:.
*indicates sequences isolated more than once.

TABLE 5
PEPTIDES FROM PHAGE RECOVERED FROM SKIN

| | |
|---|---|
| CYADCEGTCGMVC (174) | CWNICPGGCRALC* (175) |
| GPGCEEECQPAC (176) | CKGTCVLGCSEEC* (177) |
| CSTLCGLRCMGTC (178) | CMPRCGVNCKWAC (179) |
| CVGACDLKCTGGC (180) | CVALCREACGEGC* (3) |
| CSSGCSKNCLEMC* (181) | CGRPCRGGCAASC (182) |
| CQGGCGVSCPIFC (183) | CAVRCDGSCVPEC* (184) |
| CGFGCSGSCQMQC (185) | CRVVCADGCRFIC (186) |
| CTMGCTAGCAFAC (187) | CEGKCGLTCECTC (188) |
| CNQGCSGSCDVMC (189) | CASGCSESCYVGC (190) |
| CGGGCQWGCAGEC* (191) | CSVRCKSVCIGLC (192) |
| CPSNCVALCTSGC (193) | CVEGCSSGCGPGC (194) |
| CRVVCADGCRLIC (195) | CSTLCGLRCMGTC (196) |
| CFTFCEYHCQLTC (197) | CVDVCCDGCPVCC (437) |
| RVPLSGDVEH (438) | LRVMSFTSGQ (439) |
| RFSVGSLFGS (440) | CGATCEMQCPSGC (441) |

Parentheses contain SEQ ID NO:.
*indicates sequences isolated more than once.

TABLE 6
PEPTIDES FROM PHAGE RECOVERED FROM RETINA

| | |
|---|---|
| CRRIWYAVC (198) | CSAYTTSPC (199) |
| CSCFRDVCC* (5) | CTDKSWPC (200) |
| CTDNRVGS (201) | CTIADFPC (202) |
| CTSDISWWDYKC (203) | CTVDNELC (204) |
| CVGDCIGSCWMFC (205) | CVKFTYDC[2] (206) |
| CVSGHLNC (207) | CYGESQQMC (208) |
| CYTGETWTC (209) | CAVSIPRC (210) |
| CDCRGDCFC (211) | CDSLCGGACAARC (212) |
| CERSQSKGVHHC (213) | CFKSTLLC (214) |
| CFWHNRAC (215) | CGDVCPSECPGWC (216) |
| CGEFKVGC* (14) | CGLDCLGDCSGAC (217) |
| CGPGYQAQCSLRC (218) | CGSHCGQLCKSLC (219) |
| CHMGCVSPCAYVC (220) | CILSYDNPC (221) |
| CISRPYFC (222) | CKERLEYTRGVC (223) |
| CKERPSNGLSAC (224) | CKPFRTEC (225) |
| CKSGCGVACRHMC (226) | CLKPGGQEC (227) |
| CMDSQSSC* (228) | CMNILSGC (229) |
| CNIPVTTPIFGC (230) | CNQRTNRESGNC* (231) |
| CNRKNSNEQRAC (232) | CNRMEMPC (233) |
| CQIRPIDKC (234) | CAIDIGGAC (235) |
| CGRFDTAPQRGC (236) | CKRANRLSC (237) |
| CLLNYTYC* (238) | CLNGLVSMC (239) |
| CMSLGNNC (240) | CNRNRMTPC (241) |
| CQASASDHC* (242) | CQLINSSPC (243) |
| CQRVNSVENASC (244) | CRKEHYPC (245) |
| CRRHMERC (246) | CSGRPFKYC (247) |
| CTHLVTLC (248) | CTSSPAYNC (249) |
| CVTSNLRVC* (250) | CWDSGSHIC (251) |
| CERSHGRLC[1] (252) | CGNLLTRRC (253) |
| CINCLSQC (254) | CLRHDFYVC (255) |
| CNSRSENC (256) | CRYKGPSC (257) |

TABLE 6-continued
PEPTIDES FROM PHAGE RECOVERED FROM RETINA

| | |
|---|---|
| CSHHDTNC (258) | CSRWYTTC (259) |
| CYAGSPLC (260) | CQTTSWNC* (261) |
| CQWSMNVC (262) | CRARIRAEDISC* (263) |
| CRDVVSVIC (6) | CRREYSAC (264) |

Blast-Search:
[1] rat retinal guanylcyclase precursor EC4.6.1.2
[2] rat glutamate receptor subunit epsilon 1 precursor
No stainings for any motif tested, only evidence for preferential homing are the RDV-containig phages in comparison to an ampicillin-phage.
Parentheses contain SEQ ID NO:.
*indicates sequences isolated more than once.

TABLE 7
PEPTIDES FROM PHAGE RECOVERED FROM PROSTATE

| | |
|---|---|
| EVQSAKW (265) | KRVYVLG (266) |
| GRLSVQV (267) | WKPASLS (268) |
| FAVRVVG (269) | LVRPLEG (270) |
| GFYRMLG (271) | EGRPMVY (272) |
| GSRSLGA (273) | RVWQGDV (274) |
| GDELLA (275) | FVWLVGS (276) |
| GSEPMFR (277) | VSFLEYR (22) |
| WHQPL (278) | SMSIARL* (21) |
| RGRWLAL* (279) | QVEEFPC (280) |
| LWLSGNW (281) | GPMLSVM (282) |
| WTFLERL (283) | VLPGGQW (284) |
| REVKES (285) | RTPAAVM (286) |
| GEWLGEC (287) | PNPLMPL (288) |
| SLWYLGA (289) | YVGGWEL (290) |

Parentheses contain SEQ ID NO:.
*indicates sequences isolated more than once.

TABLE 8
PEPTIDES FROM PHAGE RECOVERED FROM OVARY

| | |
|---|---|
| EVRSRLS* (10) | RVGLVAR* (11) |
| AVKDYFR (291) | GVRTSIW (292) |
| RPVGMRK (293) | RVRLVNL (294) |
| FFAAVRS (295) | KLVNSSW (296) |
| LCERVWR (297) | FGSQAFV (298) |
| WLERPEY (299) | GGDVMWR (300) |
| VRARLMS (301) | TLRESGP (302) |

Parentheses contain SEQ ID NO:.
*indicates sequences isolated more than once.

TABLE 9
PEPTIDES FROM PHAGE RECOVERED FROM LYMPH NODE

| | |
|---|---|
| WGCKLRFCS (303) | MECIKYSCL (304) |
| GICATVKCS (305) | PRCQLWACT (306) |
| TTCMSQLCL (307) | SHCPMASLC (308) |
| GCVRRLLCN (309) | TSCRLFSCA (310) |
| KYCTPVECL (311) | RGCNGSRCS (312) |
| MCPQRNCL (313) | PECEGVSCI (314) |
| AGCSVTVCG* (315) | IPCYWESCR (316) |
| GSCSMFPCS* (317) | QDCVKRPCV (318) |
| SECAYRACS* (319) | WSCARPLCG* (320) |
| SLCGSDGCR (321) | RLCPSSPCT (322) |
| MRCGFSGCT (323) | RYCYPDGCL (324) |
| STCGNWTCR (325) | LPCTGASCP (326) |
| CSCTGQLCR (327) | LECRRWRCD (328) |
| GLCQIDECR* (329) | TACKVAACH (330) |
| DRCLDIWCL* (331) | XXXQGSPCL (332) |
| PLCMATRCA* (333) | RDCSHRSCE* (334) |
| NPCLRAACI* (335) | PTCAYGWCA* (336) |

TABLE 9-continued
PEPTIDES FROM PHAGE RECOVERED FROM LYMPH NODE

| | |
|---|---|
| LECVANLCT* (337) | RKCGEEVCT* (338) |
| EPCTWNACL* (339) | LVCPGTACV (340) |
| LYCLDASCL (341) | ERCPMAKCY (342) |
| LVCQGSPCL (343) | QQCQDPYCL* (344) |
| DXCXDIWCL (345) | QPCRSMVCA (346) |
| KTCVGVRV (347) | WSCHEFMCR (348) |
| LTCWDWSCR (350) | SLCRLSTCS (351) |
| KTCAGSSCI (352) | VICTGRQCG (353) |
| NPCFGLLV (354) | SLCTAFNCH (355) |
| RTCTPSRCM (356) | QSCLWRICI (357) |
| QYCWSKGCR (358) | LGCFPSWCG (359) |
| VTCSSEWCL (360) | RLCSWGGCA (361) |
| STCISVHCS (362) | EVCLVLSCQ (363) |
| IACDGYLCG (364) | RDCVKNLCR (365) |
| XGCYQKRCT (366) | LGCFXSWCG (367) |
| IRCWGGRCS (368) | IPCSLLGCA (369) |
| AGCVQSQCY (370) | PRCWERVCS (371) |
| KACFGADCX (372) | TLCPLVACE (373) |
| SACWLSNCA (374) | SECYTGSCP (375) |
| GLCQEHRCW (376) | VECGFSAVF (377) |
| EDCREWGCR (378) | HWCRLLACR (379) |

Parentheses contain SEQ ID NO:.
*indicates sequences isolated more than once.
X = Not known.

TABLE 10
PEPTIDES FROM PHAGE RECOVERED FROM ADRENAL GLAND

| | |
|---|---|
| HKGQVYS (380) | FSDVHFW* (381) |
| RGIFVSS (382) | PKVKLSE (383) |
| LRFWQES (384) | IWTVVGQ (385) |
| DKVGLSV (386) | SETWRQF (387) |
| LDGMIVK (388) | RYPLAGG (389) |
| FTDGEDK (390) | RSTEHMS (391) |
| SGRRHEL (392) | LMLPRAD* (27) |
| SSSRVRS (393) | YHRSVGR (394) |
| PLLRPPH (395) | SDKLGFV* (396) |
| LPRYLLS (28) | AGSRTNR (397) |
| ITQLHKT (398) | ARCLVYR (399) |
| GYVAVMT* (400) | GLQVKWV (401) |
| IFTPGWL (402) | KQTSRFL (403) |
| R(Y/F)LLAGG (404) | |

Parentheses contain SEQ ID NO:.
*indicates sequences isolated more than once.

TABLE 11
PEPTIDES FROM PHAGE RECOVERED FROM LIVER

| | |
|---|---|
| ARRGWTL (405) | SRRFVGG* (406) |
| QLTGGCL (407) | ALERRSL (408) |
| KAYFRWR (409) | RWLAWTV (410) |
| VGSFIYS* (411) | LSLLGIA (412) |
| LSTVLWF (413) | SLAMRDS (414) |
| GRSSLAC (415) | SELLGDA (416) |
| CGGAGAR (417) | WRQNMPL* (418) |
| DFLRCRV (419) | QAGLRCH (420) |
| RALYDAL (421) | WVSVLGF (422) |
| GMAVSSW (423) | SWFFLVA (424) |
| WQSVVRV (425) | VKSVCRT* (12) |
| CGNGHSC (426) | AEMEGRD (427) |
| SLRPDNG (428) | PAMGLIR (429) |

Parentheses contain SEQ ID NO:.
*indicates sequences isolated more than once.

We claim:

1. A method of selectively directing a moiety to lung endothelium in a subject, comprising administering to said subject a conjugate comprising a moiety linked to a MDP-binding homing molecule, wherein said MDP-binding homing molecule is identified by a method comprising contacting membrane dipeptidase (MDP) with one or more molecules and determining specific binding of a molecule to said MDP, wherein said moiety is selectively directed to lung endothelium in said subject, and wherein said homing molecule has the ability to specifically bind the MDP classified as EC 3.4.13.19.

2. The method of claim 1, wherein said MDP-binding homing molecule is a peptide comprising the sequence:

$X_1$-G-F-E-$X_2$ (SEQ ID NO: 17)

wherein $X_1$ and $X_2$ each is 1 to 10 independently selected amino acids.

3. The method of claim 2, wherein said MDP-binding homing peptide comprises a sequence selected from the group consisting of CGFECVRQCPERC (SEQ ID NO: 1) and CGFELETC (SEQ ID NO: 2).

4. The method of claim 1, wherein said MDP-binding homing molecule comprises the following Structure 1:

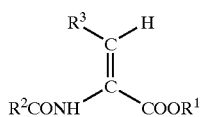

wherein R² and R³ are hydrocarbon radicals in the range respectively of 3–10 and 1–15 carbon atoms; in either one of these R² or R³ hydrocarbon chains 1–6 hydrogens may be replaced by halogens or a nonterminal methylene may be replaced by oxygen or sulfur, including oxidized forms of the latter; additionally, a terminal hydrogen in R³ can also be replaced by hydroxyl or thiol, which may be acylated or carbamoylated; or the hydrogen can be replaced by amino, which may be derivatized as in an acylamino, ureido, amidino, quanidino, or alkyl or substituted amino group, including quaternary nitrogen grouping; or, there may be replacement by acid groups such as carboxylic, phosphonic or sulfonic acid groups or esters or amides thereof, or cyano; or combinations thereof, such as a terminal amino acid grouping; and R¹ is hydrogen or lower alkyl ($C_{1-6}$) or dialkylaminoalkyl, or a pharmaceutically acceptable cation.

5. The method of claim 4, wherein said MDP-binding homing molecule is 7-(L-2-amino-2-carboxyethylthio)-2-(2,2-dimethylcyclopropanecarboxamido)-2-heptenoic acid.

6. The method of claim 4, wherein R² is branched alkyl or cycloalkyl with a limitation that the carbon adjacent to the carbonyl cannot be tertiary.

7. The method of claim 6, wherein R³ is n-alkyl (1–9 carbons) or n-alkyl (1–9 carbons) having a terminal substituent which is a quaternary nitrogen, amine derivative or amino acid derived group.

8. The method of claim 7, wherein R² is 2,2-dimethylcyclopropyl or 2,2-dichlorocyclopropyl and R³ is a hydrocarbon chain of 3 to 7 carbon atoms without a terminal substituent or having a terminal substituent which is trimethylammonium, amidino, guanidino or 2-amino-2-carboethylthio.

9. The method of claim 8, wherein said MDP-binding homing molecule is selected from the group consisting of:

Z-2-(2,2-dimethylcyclopropanecarboxamido)-8-trimethylammonium hydroxide-2-octenoic acid inner salt;

Z-2-(2,2-dichlorocyclopropanecarboxamido)-8-trimethylammonium hydroxide-2-octenoic acid inner salt;

Z-2-(2,2-dimethylcyclopropanecarboxamido)-8-guanidino-2-octenoic acid;

Z-2-(2,2-dimethylcyclopropanecarboxamido)-8-guanidino-2-octenoic acid;

Z-2-(2,2-dimethylcyclopropanecarboxamido)-8-ureido-2-octenoic acid;

Z-8-(1-2-amino-2-carboxyethylthio)-2-(2,2-dimethylcyclopropanecarboxamido)-2-octenoic acid;

Z-2-(2,2-dimethylcyclopropanecarboxamido)-2-octenoic acid (racemic and dextrorotatory forms);

Z-2-(2,2-dichlorocyclopropanecarboxamido)-2-octenoic acid;

7-(L-2-amino-2-carboxyethylthio)-2-(2,2-dimethylcyclopropanecarboxamido)-2-heptenoic acid; and 6-(L-2-amino-2-carboxyethylthio)-2-(2,2-dimethylcyclopropanecarboxamido)-2-hexenoic acid.

10. The method of claim 1, wherein said moiety is a therapeutic agent.

11. The method of claim 10, wherein said therapeutic agent is a drug.

* * * * *